(12) United States Patent
Craig et al.

(10) Patent No.: US 6,242,494 B1
(45) Date of Patent: Jun. 5, 2001

(54) SUBSTITUTED β-AMINO ACID INHIBITORS OF METHIONINE AMINOPEPTIDASE-2

(75) Inventors: Richard A. Craig, Racine, WI (US); Jack Henkin, Highland Park; Megumi Kawai, Libertyville, both of IL (US); Linda M. Lynch, Pleasant Prairie, WI (US); Jyoti Patel, Libertyville, IL (US); George S. Sheppard, Willmette, IL (US); Jieyi Wang, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/303,807

(22) Filed: Apr. 30, 1999

Related U.S. Application Data
(60) Provisional application No. 60/085,877, filed on May 1, 1998.

(51) Int. Cl.$^7$ ........................ A61K 31/165; C07C 233/01
(52) U.S. Cl. ........................ 514/613; 564/123; 564/165; 564/191; 564/194; 564/196; 514/615; 514/619; 514/626
(58) Field of Search ..................... 514/613, 615, 514/619, 626; 564/123, 165, 191, 194, 196

(56) References Cited

U.S. PATENT DOCUMENTS
5,442,044   8/1995   Hoover et al. .
5,455,271 * 10/1995   Yuan et al. ........................... 514/538

FOREIGN PATENT DOCUMENTS
1510477   10/1978   (GB) .

OTHER PUBLICATIONS

J. Folkman and Y. Shing, "Angiogenesis", The Journal of Biological Chemistry, vol. 267, No. 16, (Jun. 5, 1992), pp. 10931–10934.

J. Folkman and M. Klagsbrun, "Angiogenic Factors", Science, vol. 235 (Jan. 23, 1987), pp. 442–447.

J. Folkman, "How is Blood Vessel Growth Regulated in Normal and Neoplastic Tissue?—G.H.A. Clowes Memorial Award Lecture", Cancer Research, vol. 46 (Feb. 1986), pp. 467–473.

J. Folkman, "What Is The Evidence That Tumors Are Angiogenesis Dependent?", Journal of the National Cancer Institute, vol. 82, No. 1 (Jan. 3, 1990), pp. 4–6.

N. Weidner, M.D., et al., "Tumor Angiogenesis and Metastasis—Correlation in Invasive Breast Carcinoma", The New England Journal of Medicine, vol. 324 (Jan. 3, 1991), pp. 1–8.

D. Ingber, et al., "Synthetic Analogues of Fumagillin Covalently Binds and Inhibits The Tumour Growth", Letters to Nature, vol. 348, (Jun. 12, 1990), pp. 555–557.

N. Sin, et al., "The Anti–Angiogenic Agent Fumagillin Covalently Binds and Inhibits The Methionine Aminopeptidase, MetAP–2", Proc. Natl. Acad. Sci. USA, vol. 94 (Jun. 1997), pp. 6099–6103.

E.C. Griffith, et al., "Methionine Aminopeptidase (type 2) Is the Common Target For Angiogenesis Inhibitors AGM–140 And Ovalicin", Chemistry and Biology, vol. 4 (Jun. 1997), pp. 461–471.

J. Abe, et al., "A Fumagillin Derivative Angiogenesis Inhibitor, AGM–1470, Inhibits Activation of Cyclin–dependent Kinases and Phosphorylation of Retinoblastoma Gene Product but not Protein Tyrosyl Phosphorylation of Protooncogene Expression in Vascular Endothelial Cells", Cancer Research, vol. 54 (Jul. 1, 1994), pp. 3407–3412.

Nishizawa, R., "Synthesis and Structure–Activity Relationships of Bestatin Analogues, Inhibitors of Aminopeptidase B", Journal of Medicinal Chemistry, US, American Chemical Society, vol. 20, No. 4, (1977), pp. 510–515.

\* cited by examiner

Primary Examiner—C. S. Aulakh
(74) Attorney, Agent, or Firm—B. Gregory Donner; Gregory W. Steele

(57) ABSTRACT

A class of substituted b-amino acids are potent inhibitor of methionine aminopeptidase type 2 (MetAP2) and are thus useful in inhibiting angiogenesis and disease conditions which depend upon angiogenesis for their development such as diabetic retinopathy, tumor growth, and conditions of inflammation. Pharmaceutical compounds containing the compounds and methods of inhibiting methionine aminopeptidase-2, and angiogenesis are also disclosed.

15 Claims, No Drawings

SUBSTITUTED β-AMINO ACID INHIBITORS OF METHIONINE AMINOPEPTIDASE-2

This application is a continuation-in-part of pending U.S. Provisional Application Ser. No. 60/083,877, filed May 1, 1998, incorporated herein by reference.

FIELD OF THE INVENTION

The present invention relates to organic compounds having biological activity, to compositions containing the compounds, and to medical methods of treatment. More particularly, the present invention concerns a class of substituted beta-amino acids and their pharmaceutically acceptable salts, pharmaceutical compositions containing the compounds, and methods of treating pathological conditions arising from or dependent upon angiogenesis.

BACKGROUND OF THE INVENTION

Angiogenesis is the fundamental process by which new blood vessels are formed and is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions, these molecules appear to maintain the microvasculature in a quiescent state (i.e. one of no capillary growth) for prolonged periods which may last for a s long as weeks or in some cases, decades. When necessary, however, (such as during wound repair), these same cells can undergo rapid proliferation and turnover with a 5 day period. (Folkman, J. and Shing, Y., *The Journal of Biological Chemistry*, 267: 10931–10934 (1987), and Folkman, J. and Klagsbrun, M., *Science*, 235: 442–447 (1987)).

Although angiogenesis is a highly regulated process under normal conditions, many disease (characterized s "angiogenic diseases") are driven by persistent unregulated angiogenesis. Otherwise stated, unregulated angiogenesis may either cause a particular disease directly or exascerbate an existing pathological condition. For example, ocular neovacularization has been implicated as the most common cause of blindness and dominates approximately 20 eye diseases. In certain existing conditions such as arthritis, newly formed capillary blood vessels invade the joints and destroy cartilage. In diabetes, new capillaries formed in the retina invade the vitreous bleed, and cause blindness. Growth and metastasis of solid tumors are also angiogenesis-dependent (Folkman J., *Cancer Research*46 467–473 (1986). Folkman, J., *Journal of the National Cancer Institute*, 82: 4–6 (1989)0. It has been shown for example that tumors which enlarge to greater than 2 mm, must obtain their own blood supply and do so by inducing the growth of new capillary blood vessels. Once these new blood vessels become embedded in the tumor, they provide a means for tumor cells to enter the circulation and metastasize to distant sites, such as liver, lung or bone (Weidner, N., et al., *The New England Journal of Medicine*, 324: 1–8 (1991)).

Because of this pivotal role played by neovacularization in tumor formation and metastasis and in such other disease conditions as arthritis, inflammation, maccular degeneration of age, and diabetic retinopathy, agents which inhibit angiogenesis have been the subject of active current research for their clinical potential.

D. Ingber, et al., in *Nature*, 348: 555–557 report that fumagillin, a natural product of fungal origin, and its synthetic analog, O-(chloroacetylcarbamoyl)fumagillol, also known as AGM-1470 or TNP-470, act as potent inhibitors of angiogenesis, with TNP-470 being 50-fold more potent than its natural precursor.

Ny Sin et al., *Proc. Natl. Acad. Sci. USA*94: 6099–6103 (1997) and Eric C. Griffith, et al., *Chemistry and Biology*, 4(6): 461–471 (1997) report that both AGM-1470 and ovalicin, a sequiterpene isolated from the fungus *Pseudorotium ocalis* bind to a common bifunctional protein, type 2 methionine aminopeptidase, MetAP2, and conclude that MetAP2 plays a critical role in the proliferation of endothelial cells and may serve as a promising target for the development of new anti-angiogenic drugs.

J. Abe, et al., *Cancer Research*, 54: 3407–3412 (1994) report that fumagillin, and its derivative TNP-470, are effective in inhibiting neovacularization by arresting the endothelial cell cycle in the late $G_1$ phase.

The literature has thus established a casual line between inhibition of MetAP2 and the resultant inhibition of endothelial cell proliferation and neovacularization. There is a need for discovery of new agents which inhibit MetAP2 for their potential as new drugs in combating angiogenesis or neovacularization and disease conditions such as arthritis, inflammation, maccular degeneration of the eye, diabetic retinopathy, and tumor growth which depend upon neovasculaturization for their development. Compounds of the current invention are structurally novel, reversible inhibitors of MetAP2 which may display improved pharmaceutical properties and diminished side effects relative to the currently known irreversible inhibitors such as fumagillin and TNP470.

SUMMARY OF THE INVENTION

In its principle embodiment, the present invention provides a compound having activity for inhibiting methionine aminopeptidase type 2 (MetAP2 or MetAP2—2) having the structural, formula I

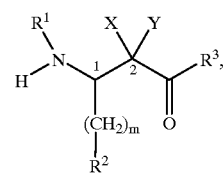

or a pharmaceutically acceptable salt, ester or prodrug thereof, wherein the small numerals denote chiral centers in the compound;
m is 1–3;
$R^1$ is selected form the group consisting of
  (1) hydrogen,
  (2) alkyl,
  (3) carboxaldehyde,
  (4) alkanoyl, where the alkanoyl can be optionally substituted with hydroxyl, and
  (5) $—(CH_2)_nCO_2R^4$, where n is 0–6, and $R^4$ is selected from the group consisting of
    (a) hydrogen,
    (b) alkyl,
    (c) cycloalkyl,
    (d) (cycloalkyl)alkyl,
    (e) aryl, and
    (f) arylalkyl, where (c) and (d) can be optionally substituted with 1, 2, or 3 substituents independently selected form the group consisting of
  (i) alkyl,
  (ii) alkoxy, and
  (iii) aryl, and
where (e) and (f) can be optionally substituted with 1, 2, or 3 substituents independently selected form the group consisting of
  (i) alkyl,
  (ii) alkanoyl,
  (iii) alkoxy,
  (iv) —$CO_2R^{4'}$, where $R^4$, is selected form the group of consisting of,
    (a) hydrogen,
    (b) alkyl,
    (c) cycloalkyl,
    (d) (cycloalkyl)alkyl,
    (e) aryl, and
    (f) arylalkyl,
  (v) alkanoyloxy,
  (vi) carboxaldehyde,
  (viii) cycloalkenyl,
  (ix) halo,
  (x) nitro,
  (xi) perfluoroalkyl,
  (xii) perfluoroalkoxy,
  (xiv) aryloylalkyloxycarbonylalkyl,
  (xv) —$NR^6R^{6'}$, where $R^6$ and $R^{6'}$ are independently selected from the group consisting of
    (1') hydrogen,
    (2') alkyl optionally substituted with alkoxy,
    (3') aryl,
    (4') arylalkyl, and
    (5') a nitrogen-protecting group,
  (xvi) —$SO_2NR^6R^{6'}$, where $R^6$ and $R^{6'}$ are defined above, and
  (xvii) —$C(O)NR^6R^{6'}$, where $R^6$ and $R^{6'}$ are defined above;
$R^2$ is selected from the group consisting of
  (1) alkyl,
  (2) cycloalkyl,
  (3) (cycloalkyl)alkyl,
  (4) —$C(H)(SR^{15})(SR^{15'})$, where $R^{15}$ and $R^{15'}$ are alkyl, or $R^{15}$ and $R^{15'}$, together with the sulfurs to which they are attached, are a 1,3-dithiolane ring or a 1,3-dithiane ring,
  (5) aryl,
  (6) arylalkyl, and
  (7) —$SR^5$, where $R^5$ is selected from the group consisting of
    (a) alkyl,
    (b) cycloalkyl,
    (c) (cycloalkyl)alkyl, and
    (d) benzyl, where the benzyl can be optionally substituted with 1,2, or 3 substituents independently selected from the group consisting of
      (i) alkyl,
      (ii) alkanoyl,
      (iii) alkoxy,
      (iv) —$CO_2R^4$, where $R^4$ is defined above,
      (v) alkanoyloxy,
      (vi) carboxaldehyde,
      (vii) cycloalkyl,
      (viii) cycloalkenyl,
      (ix) halo,
      (x) nitro,
      (xi) perfluoroalkyl,
      (xii) perfluoroalkoxy,
      (xiii) —$NR^6R^{6'}$, where $R^6$ and $R^{6'}$ are defined above,
      (xiv) —$SO_2NR^6R^{6'}$, where $R^6$ and $R^{6'}$ are defined above, and
      (xv) —$C(O)NR^6R^{6'}$, where $R^6$ and $R^{6'}$ are defined above;
$R^3$ is selected form the group consisting of
  (1) an aminoacyl group optionally capped with a carboxyl protecting group,
  (2) —$N(R^6)(CH_2)_pR$, where p is 0–6, $R^6$ is defined above, and $R^7$ is selected from the group consisting of
    (a) hydrogen,
    (b) alkyl, where the alkyl can be optionally substituted with 1, 2, 3, or 4 substituents independently selected form the group consisting of
      (i) oxo,
      (ii) thioxo,
      (iii) alkoxy,
      (iv) —$CO_2R^4$, wherein $R^4$ is defined above,
      (v) alkanoyloxy,
      (vi) carboxaldehyde,
      (vii) cycloalkyl,
      (viii) cycloalkenyl,
      (ix) halo,
      (x) nitro,
      (xi) perfluoroalkyl,
      (xii) perfluoroalkoxy,
      (xiii) —$NR^6R^{6'}$, where $R^6$ and $R^{6'}$ are defined above,
      (xiv) —$SO_2NR^6R^{6'}$, where $R^6$ and $R^{6'}$ are defined above,
      (xv) —$C(O)NR^6R^{6'}$, where $R^6$ and $R^{6'}$ are defined above;
      (xvi) aryl,
      (xvii) hydroxy, and
      (xviii) heterocycle,
    (c) cycloalkyl, where the aryl can be optionally substituted wit 1, 2, or 3 substituents independently selected from the group consisting of
      (i) alkyl,
      (ii) halo,
      (iii) oxo, and
      (iv) aryl,
    (d) aryl, where the aryl can be optionally substituted with 1, 2, or 3 substituents independently selected from the group consisting of
      (i) alkyl,
      (ii) alkanoyl,
      (iii) alkoxy,
      (iv) —$CO_2R^4$, where $R^4$ is defined above,
      (v) alkanoyloxy,
      (vi) carboxaldehyde,
      (vii) cycloalkyl,
      (viii) cycloalkenyl,
      (ix) halo,
      (x) nitro,
      (xi) perfluoroalkyl,
      (xii) perfluoroalkoxy,
      (xiii) —$NR^6R^{6'}$, where $R^6$ and $R^{6'}$ are defined above,
      (xiv) —$SO_2NR^6R^{6'}$, where $R^6$ and $R^{6'}$ are defined above,
      (xv) —$C(O)NR^6R^{6'}$, where $R^6$ and $R^{6'}$ are defined above;
      (xvi) aryloxy,
      (xvii) arylalkoxy,
      (xvi) aryl,
      (xvii) hydroxy, and (xviii) heterocycle,
(e) —CO$_2$R$^4$, where R$^4$ is defined above,
(f) —CONR$^6$R$^8$, where R$^6$ is defined above, and R$^8$ is selected from the group consisting of
  (i) hydrogen
  (ii) alkyl,
  (iii) aryl, and
  (iv) heterocycle,
  where (ii)–(iv) can be optionally substituted with one, two, or three groups independently selected from the group consisting of
    (1') alkyl,
    (2') alkanoyl,
    (3') alkoxy,
    (4') —CO$_2$R$^4$, where R$^4$ is defined above,
    (5') alkanoyloxy,
    (6') carboxaldehyde,
    (7') cycloalkyl,
    (8') cycloalkenyl,
    (9') halo,
    (10') nitro,
    (11') perfluoroalkyl,
    (12') perfluoroalkoxy,
    (13') —NR$^6$R$^{6'}$, where R$^6$ and R$^{6'}$ are defined above,
    (14') —SO$_2$NR$^6$R$^{6'}$, where R$^6$ and R$^{6'}$ are defined above,
    (15') —C(O)NR$^6$R$^{6'}$, where R$^6$ and R$^{6'}$ are defined above;
    (16') aryloxy,
    (17') arylalkoxy,
    (18') aryl,
    (19') hydroxy, and
    (20') heterocycle,
(g) heterocycle, where the heterocycle can be optionally substituted with one, two, or three groups independently selected form the group consisting of
  (i) alkyl,
  (ii) alkanoyl,
  (iii) alkoxy,
  (iv) —CO$_2$R$^4$, where R$^4$ is defined above,
  (v) alkanoyloxy,
  (vi) carboxaldehyde,
  (vii) cycloalkyl,
  (viii) cycloalkenyl,
  (ix) halo,
  (x) nitro,
  (xi) perfluoroalkyl,
  (xii) perfluoroalkoxy,
  (xiii) —NR$^6$R$^{6'}$, where R$^6$ and R$^{6'}$ are defined above,
  (xiv) —SO$_2$NR$^6$R$^{6'}$, where R$^6$ and R$^{6'}$ are defined above,
  (xv) —C(O)NR$^6$R$^{6'}$, where R$^6$ and R$^{6'}$ are defined above,
  (xvi) aryloxy,
  (xvii) arylalkoxy,
  (xviii) aryl,
  (xix) hydroxy, and
  (xix) heterocycle,
(h) —NR$^6$R$^8$, where R$^6$ and R$^8$ are defined above, and
—N(R$^6$)SO$_2$R$^{12}$, where R$^6$ is defined previously, and R$^{12}$ is selected from the group consisting of
  (i) alkyl,
  (ii) aryl,
  (iii) arylalkyl,
  (iv) heterocycle, and
  (v) (heterocycle)alkyl,
  where (ii)–(v) can be optionally substituted with 1, 2, or 3 groups independently selected form the group consisting of
    (1') alkyl,
    (2') alkanoyl,
    (3') alkoxy,
    (4') —CO$_2$R$^4$, where R$^4$ is defined above,
    (5') alkanoyloxy,
    (6') carboxaldehyde,
    (7') cycloalkyl,
    (8') cycloalkenyl,
    (9') halo,
    (10') nitro,
    (11') perfluoroalkyl,
    (12') perfluoroalkoxy,
    (13') —NR$^6$R$^{6'}$, where R$^6$ and R$^{6'}$ are defined above,
    (14') —SO$_2$NR$^6$R$^{6'}$, where R$^6$ and R$^{6'}$ are defined above,
    (15') —C(O)NR$^6$R$^{6'}$, where R$^6$ and R$^{6'}$ are defined above;
    (16') aryloxy,
    (17') arylalkoxy,
    (18') aryl,
    (19') hydroxy, and
    (20') heterocycle,
(3) —O(CH$_2$)$_p$R$^7$ where p and R$^7$ are defined above, and
(4) —NR$^{20}$R$^{21}$, where R$^{20}$ and R$^{21}$, together with the nitrogen atom to which they are attached, are a 3- to 7-membered ring optionally containing therein 1 to 2 double bonds and optionally containing therein a moiety selected from the group consisting of
  (a) oxygen,
  (b) nitrogen and
  (c) —S(O)$_x$-, wherein x is 0–2,
  where the ring formed by R$^{20}$ and R$^{21}$ can be optionally substituted with 1, 2, or 3 groups independently selected from the group consisting of
    (1') alkyl,
    (2') alkanoyl,
    (3') alkoxy,
    (4') —CO$_2$R$^4$, where R$^4$ is defined above,
    (5') alkanoyloxy,
    (6') carboxaldehyde,
    (7') cycloalkyl,
    (8') cycloalkenyl,
    (9') halo,
    (10') nitro,
    (11') perfluoroalkyl,
    (12') perfluoroalkoxy,
    (13') —NR$^6$R$^{6'}$, where R$^6$ and R$^{6'}$ are defined above,
    (14') —SO$_2$NR$^6$R$^{6'}$, where R$^6$ and R$^{6'}$ are defined above,
    (15') —C(O)NR$^6$R$^{6'}$, where R$^6$ and R$^{6'}$ are defined above;
    (16') aryloxy,
    (17') arylalkoxy,
    (18') aryl,
    (19') hydroxy, and
    (20') heterocycle;
X is hydroxyl or sulfhydryl; and
Y is hydrogen; or
X and Y, taken together with the carbon atom to which they are attached, form a carbonyl or thiocarbonyl.

In another embodiment, the present invention provides a pharmaceutical composition comprising a compound of formula I or a pharmaceutically acceptable salt, ester, or prodrug thereof, in combination with a pharmaceutically acceptable carrier.

In another embodiment, the present invention provides a method of inhibiting angiogenesis in a mammal comprising adminstering to the mammal a pharmaceutically acceptable amount of a compound of formula I.

DETAILED DESCRIPTION

DEFINITION OF TERMS

When used throughout this specification and the appended claims, the following terms have the ascribed meanings.

The term "alkanoyl," as used herein, denotes an alkyl group attached to the parent molecular group through a carbonyl group. The alkanoyl groups of this invention can be optionally substituted.

The term "alkanoyloxy," as used herein, denotes an alkanoyl group attached to the parent molecular group through an oxygen atom. The alkanoyloxy groups of this invention can be optionally substituted.

The term "alkyl," as used herein, denotes a radical formed by the removal of one hydrogen atom from a straight or branched saturated hydrocarbon of one to twelve carbon atoms. Representative hydrocarbon groups include methyl, ethyl, n-propyl, iso-propyl, n-butyl, sec-butyl, iso-butyl tert-butyl, and the like The alkyl groups of this invention can be optionally substituted.

The term "alkoxy," as used herein, denotes a lower alkyl group, as defined herein attached to the parent molecular moiety through an oxygen atom and includes such groups as methoxy, ethoxy, n-propoxy, n-butoxy, tert-butoxy, and the like. The alkoxy groups of this invention can be optionally substituted.

The term "aminoacyl group," as used herein, donates a radical derived form naturally or unnaturally occurring amino acids. Representative aminoacyl groups include glycyl, alanyl, valyl, leucyl, iso-leucyl, methionyl, seryl, threonyl, cysteinyl, phenylalanyl, homophenylalanyl, and O-methyltyrosinyl in the racemic, δ or L configurations.

The term "aryl," as used herein, denotes a mono- or bicyclic-carbocyclic ring system having one or two aromatic rings. Aryl groups are exemplified by phenyl, naphthyl, 1,2dihydronaphthyl, 1,2,3,4-tetrahydronaphthyl, fluorenyl, indanyl, and indenyl. Bicyclic aryl groups of this invention can be attached to the parent molecular group through a saturated or unsaturated part of the group. The aryl groups of this invention can be optionally substituted.

The term "arylalkoxy," as used herein, denotes an aryl group, as defined herein, attached to the parent molecular group through an alkoxy group. The arylalkoxy groups of this invention can be optionally substituted.

the term "arylalkyl," as used herein denotes an aryl group, as defined herein, attached to the parent molecular group through an alkyl group. The arylalkyl groups of this invention can be optionally substituted.

The term "aryloxy," as used herein, denotes an aryl group, as defined herein, attached to the parent molecular group through an oxygen atom. The aryloxy groups of this invention can be optionally substituted.

The term "aryloyl," as used herein, denotes an aryl group, as defined herein, attached to the parent molecular group through a carbonyl group. The aryloyl groups of this invention can be optionally substituted.

The term "aryloyloxy," as used herein, denotes an aryloyl group, as defined herein, attached to the parent molecular group through an oxygen atom. The aryloyloxy groups of this invention can be optionally substituted.

The term "aryloyloxyalkyl," as used herein, denotes an aryloyloxy group, as defined herein, attached to the parent molecular group through an alkyl group. The aryloyloxyalkyl groups of this invention can be optionally substituted.

The term "aryloyloxyalkylcarbonyl," as used herein, denotes an aryloyloxy group, as defined herein, attached to the parent molecular group through a carbonyl group. The aryloyloxyalkylcarbonyl groups of this invention can be optionally substituted.

The term "aryloyloxyalkylcarbonylalkyl," as used herein, denotes an aryloyloxyalkylcarbonyl group, as defined herein, attached to the parent molecular group through an alkyl group. The aryloyloxyalkylcarbonylalkyl groups of this invention can be optionally substituted.

The term "arylsulfonyl," as used herein, denotes an aryl group, as defined herein, attached to the parent molecular group through an —$SO_2$-group. The arylsulfonyl groups of this invention can be optionally substituted.

The term "arylsulfonylalkyl," as used herein, denotes an arylsulfonyl group, as defined herein, attached to the parent molecular group through an alkyl group. The arylsulfonylalkyl groups of this invention can be optionally substituted.

The term "benzyl," as used herein, denotes a phenyl group, as defined herein, attached to the parent molecular group through a methyl group. The benzyl groups of this invention can be optionally substituted.

The term "carboxaldehyde," as used herein, denotes —CHO.

The term "carbonyl," as used herein, denotes —C(O)—.

The term "carboxyl," as used herein, denotes —$CO_2H$.

The term "cycloalkyl," as used herein, denotes a radical derived by the removal of a single hydrogen atom from a saturated cyclic or bicyclic hydrocarbon and includes such groups as cyclopropyl, cyclobutyl, cyclopentyl, cyclohexyl, adamantyl, norbornyl, and the like. The cycloalkyl groups of this invention can be optionally substituted.

The term "(cycloalkyl)alkyl" denotes a cycloalkyl group as just defined, attached to the parent molecular moiety through an alkyl group as defined above and includes such representative groups as cyclopropylmethyl, cyclopentylethyl, 2-methyl-3-cyclopentylbutyl, cyclohexylmethyl, and the like. The (cycloalkyl)alkyl groups of this invention can be optionally substituted.

The term "cycloalkenyl," as used herein, denotes a monovalent cyclic or bicyclic hydrocarbon of four to twelve carbon atoms having at least one carbon-carbon double bond. The cycloalkenyl groups of this invention can be optionally substituted.

The term "halo," as used herein, denotes —F, —Cl, —Br or —I.

The term "heterocycle" as used herein denotes any 5-, 6- or 7-membered saturated ring containing from one to three heteroatoms independently selected from the group consisting of 1, 2, or 3 nitrogens, one oxygen and one nitrogen, and one sulfur and one nitrogen; wherein the nitrogen and sulfur heteroatoms can be optionally oxidized, and the nitrogen; wherein the nitrogen and sulfur heteroatoms can be optionally oxidized, and the nitrogen heteroatom can be optionally quaternized. The term "heterocycle," as used herein, also includes and to 5-, 6-, or 7-membered aromatic rings having in the ring one, two, or three heteroatoms selected from N, O, and S, and also including benzo fused analogs of these 5-, 6-, or 7-membered heterocyclic aromatic rings, Representative heterocycles of this invention include, pyrrolidinyl, piperidinyl, pyrazinyl, pyrazolyl, pyridazinyl morpholinyl, piperazinyl, thiomorpholinyl, pyridyl, pyrimidinyl, quinolyl, furyl, benzofuryl, thienyl, thiazolyl, pyrimidyl, indolyl, imidazolyl, isothiazolyl, isoxazolyl, oxadiazolyl, oxazolyl, 1,2,3-oxadiazolyl, thienyl, triazolyl 1,3,4-thiadiazolyl, and tetrazolyl, and the like.

The term "heterocycle," as used herein, also includes compounds of formula

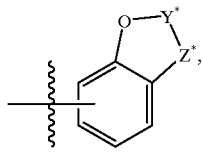

wherein Y* is selected from the group consisting of —C(O)— and —(C($R^{30}$)($R^{31}$))$_v$—, wherein $R^{30}$ and $R^{31}$ are independently selected from the group consisting of hydrogen and alkyl, and v is 1, 2, or 3, and Z* is selected from the group consisting of —CH$_2$—, —O—, —CH$_2$S(O)$_t$—, —CH$_2$O—, —CH$_2$NR$^{35}$—, and —N$^{35}$—, wherein, at each occurence, $R^{35}$ is selected from the group consisting of hydrogen and alkyl.

The term "heterocycle," as used herein, also includes bicyclic or tricyclic rings, wherein any of the aformentioned heteroaryl rings is fused to one or two rings independently selected from the group consisting of an aryl ring, a cycloalkyl ring, a cycloalkenyl ring, and another monocyclic heteroaryl ring. These heteroaryls include benzo[b]furanyl, benzo[b]thienyl, benzimidazolyl, cinnolinyl, imidazo[4,5-c]pyridinyl, quinazolinyl, thieno[2,3-c]pyridinyl, thieno[3,2-b]pyridinyl, thieno[2,3-b]pyridinyl, indolizinyl, and imidazo[1,2-a]pyridine and can be attached to the parent molecular group through either the heretoaryl group or the aryl, cycloalkyl, or cycloalkenyl group to which it is fused. The heterocycle groups of this invention can be optionally substituted.

The term "hydroxy," as used herein, denotes —OH.

The term "nitro," as used herein, denotes —NO$_2$.

The term "nitrogen-protecting group," as used herein, denotes groups intended to protect an amino group against undersirable reactions during synthetic procedures. Commonly used nitrogen-protecting groups are disclosed in Green, "Protective Groups In Organic Synthesis," (John Wiley & Sons, New York (1991)). Common N-protecting groups comprise (a) acyl groups such as formyl, acetyl, propionyl, pivaloyl, tert-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, and 4-nitrobenzoyl, (b) sulfonyl groups such as benzenesulfonyl, and para-toluenesulfonyl, (c) carbamate forming groups such as benzyloxycarbonyl, para-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α, α-dimethyl-3,5-dimethoxybenzyloxycarbonyl, benzhydryloxycarbonyl, tert-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, cyclopentyloxycarbonyl, adamantyloxycarbonyl, cyclohexyloxycarbonyl, and phenylthiocarbonyl, (d) arylalkyl groups such as benzyl, triphenylmethyl, and benzyloxymethyl, and (e) silyl groups such as trimethylsily. Preferred nitrogen-protecting groups are formyl, acetyl, benzoyl, pivaloyl, tert-butylacetyl, phenylsulfonyl, benzyl, tert-butyloxycarbonyl (Boc) and benzyloxycarbonyl (Cbz).

The term "oxo," as used herein, denotes (=O).

The term "perfluoroalkoxy," as used herein, denotes a perfluoroalkyl group attached to the parent molecular group through an oxygen atom.

The term "perfluoroalkyl," as used herein, denotes an alkyl group in which all of the hydrogen atoms have been replaced by fluoride atoms.

The term "phenyl," as used herein, denotes a radical formed by the removal of one hydrogen atoms from a benzene ring. The phenyl group of this invention can be optionally substituted.

The term "prodrug" denotes compounds that are rapidly transformed in vivo to yield the parent compounds of formula I, as for example, by hydrolysis in blood. T. Higuchi and V. Stella provide a thorough discussion of the prodrug concept in "Prodrugs as Novel Delivery Systems, " Vol. 14 of the A.C.S. Symposium Series, American Chemical Society (1975). Examples of esters useful as prodrugs for compounds containing carboxyl groups may be found on pages 14–21 of *Bioreversible Carriers in Drug Design: Theory and Application,* edited by E. B. Roche, Pergamon Press (1987).

The term "prodrug ester group" denotes any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art.

The term "pharmaceutically acceptable ester" denotes esters which hydrolyze in vivo and include those that break down readily in the human body to leave the parent compound or a salt thereof. Suitable ester groups include, for example those derived from pharmaceuticallly acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

The term"sulfhydryl," as used herein, denotes —SH.

The term "thiocarbonyl," as used herein, denotes —C(S)—.

The term "thioxo," as used herein, denotes =S.

As shown in generic chemical structural formula I above, the compounds of the invention have at least one chiral center designated by the numeral "1." When Y is hydrogen, the compounds also possess at least one additional chiral center designated by the numeral "2" in the generic formula. While compounds having either the "R," "S," or "R,S" chirality at either site are described, preferred compounds of the present invention are those in which the chirality at the site designated "1" is R and the chirality at the site designated "2" is S. The "R" and "S" stereochemical designators follow the convention established by R. S. Cahn, et al., *Angewandt Chemie. Int. Ed. Engl.,* 5: 385–415 (1966).

Diastereomers having the preferred (Site 1)R and (Site 2)S stereochemistry can be synthesized by judicious choice of optically pure starting materials, asymmetric synthesis, or may be separated from mixtures of diastereomers by methods well known in the art as, for example, by reverse phase HPLC techniques.

While compounds having a structure corresponding to the generic formula I given above are considered to fall within the scope of the present invention, a preferred sub-group of compounds is defined by structural formula I where $R^2$ is —$SR^5$ where $R^5$ is lower alkyl, most preferably, methyl or ethyl.

Another preferred sub-group of compounds of the invention are compounds of formula I where $R^2$ is cycloalkyl, preferably cyclohexyl.

Another preferred sub-group of compounds of the invention are compounds of formula I where m is one and $R^2$ is lower alkyl, preferably n-propyl.

Another preferred sub-group of compounds of the invention are compounds of formula I where X is hydroxy or sulfhydryl, and Y is hydrogen, with X is hydroxyl being particularly preferred.

Another preferred sub-group of compounds of the present invention is defined by structural formula I above where X and Y, taken together with the carbon atom to which they are attached, form a carbonyl or thiocarbonyl group, with carbonyl being particularly preferred.

A preferred sub-group of compounds of the invention are defined by structural formula I where $R^3$ is an aminoacyl group derived from a naturally occurring amino acid, where the nitrogen atom at the N-terminus of the aminoacyl group is attached to the immediately adjacent carbonyl group of the parent molecular moiety, and the C-terminus, or carboxyl functionality of the aminoacyl residue is optionally and preferably capped by a carboxyl blocking group.

Carboxyl blocking groups are well known to practitioners of the organic chemical arts, and are described in some detail in Chapter 5, pages 224–276 of "Protective Groups in organic Synthesis" Second Edition, by T. W. Greene and P. G. M. Wuts, Kohn Wiley & Sons. Inc., New York, 1991, the contents of which are incorporated herein by reference. Such carboxyl protecting groups include esters such as substituted methyl esters, substituted ethyl esters, substituted benzyl esters, silyl esters, oxazoles, 2-alkyl,-1,3-oxazolines, 4-alkyl-5-oxo-1,3-oxazolidines, 5-alkyl-4-oxo-1,3-dioxalanes, ortho esters, and amides such as N,N-dialkyl amides, pyrrolidinyl amides, piperidinyl amides, 5,6-dihydropiperidinyl amides, o-nitroanilides, and hydrazides such a N-phenylhydrazides and N,N'-dialkylhydrazides.

Specific examples of individual compounds falling within the scope of the present invention include, but are not limited to (2RS,3S,1'S)-N-((1-ethoxycarbonyl)ethyl)-3-amino-2-hydroxy-5-(methylthio)pentanamide, (2RS,3S,1'S)-N-((1-ethylcarboxamido)ethyl)-3-amino-2-hydroxy-5-(methylthio)pentanamide, (2RS,3R,1'S)-N-((1-ethylcarboxamido)ethyl)-3-amino-2-hydroxy-5-(methylthio)pentanamide (2RS,3R,1'S)-N-((1-ethoxycarbonyl)ethyl)-3-amino-2-hydroxy-5-(methylthio)pentanamide, (2RS,3R)-N-((2-phenylethyl)-3-amino-2-hydroxy-5-(methylthio)pentanamide, (2RS,3R)-N-((3-phenylpropyl)-3-amino-2-hydroxy-5-(methylthio)pentanamide, (2RS,4R)-N-(4-phenylbutyl)-3-amino-2-hydroxy-5-(methylthio)pentanamide, (2RS,3R) N-(2-(4-methoxyphenyl)ethyl)-3-amino-2-hydroxy-5-(methylthio)pentanamide, (2RS,3R)-N-(2-(4-sulfonamidophenyl)ethyl)-3-amino-2-hydroxy-5-(methylthio)pentanamide, (2RS,3R)-N-(2-(2-pyridyl)ethyl)-3-amino-2-hydroxy-5-(methylthio)pentanamide, (2RS,3R)-N-(2-(4-phenoxyphenyl)ethyl)-3-amino-2-hydroxy-5-(methylthio)pentanamide, (2RS,3R,1'S)-N-((1-ethoxycarbonyl)ethyl)-3amino-2-hydroxy-5-(ethylthio)pentanamide, (2RS,3R)-N-(4-phenyl)butyl)-3-amino-2-5-(ethylthio)pentanamide, (2RS,3R)-N-(3-(carboethoxy)ethyl)-3-amino-2-hydroxy-5-(ethylthio)pentanamide, (2RS,3R)-N-(3-(carbobenzyloxy)ethyl)-3-amino-2-hydroxy-5-(ethylthio)pentanamide, (2RS,3R)-N-(3-(carboethoxy)propyl)-3-amino-2-hydroxy-5-(ethylthio)pentanamide, (2RS,3R,1'S)-N-((1-ethoxycarbonyl)ethyl)-3-amino-2-hydroxy-heptanamide, (2RS,3R)-3-amino-2-hydroxy-5-(methylthio)pentanoic acid, (2RS,3R)-N-(2-(4-pyridyl)ethyl)-3-amino-2-hydroxy-5-(methylthio)pentanamide, (2RS,3R)-N-(2-(carboethoxy)ethyl)-3-amino-2-hydroxy-4-phenyl-butanamide, (2RS,3R)-N-(3-(carboethoxy)propyl)-3-amino-2-hydroxy-4-phenyl-butanamide, (2RS,3R)-N-(4-phenylbutyl)-3-amino-2-hydroxy-4-phenyl-butanamide, (2RS,3R,1'S)-N-((1-ethoxycarbonyl)ethyl)-3amino-2hydroxy-4-cyclohexyl-butanamide, (2RS,3R)-N-(2-(carboethoxy)ethyl)-3-amino-2-hydroxy-4-cyclohexyl-butanamide, (2RS,3R)-N-(3-(carboethoxy)propyl)-3-amino-2-hydroxy-4-cyclohexyl-butanamide, (2RS,3R,1'S)-N-((1-ethoxycarbonyl)ethyl)-3-amino-2-hydroxy-4-phenyl-butanamide, (2RS,3R)-3-amino-2-hydroxy-N-(4-methoxyphenethyl)-5-(methylsulfanyl)pentanamide, (2RS,3R)-N-((2-phenylbutyl)-3-tert-butoxycarbonylamino-2-hydroxy-5-(ethylthio)pentanamide, (2RS,3R)-N-((2-phenylbutyl)-3-acetylamino-2-hydroxy-5-(ethylthio)pentanamide, (2RS,3R)-N-((phenylbutyryl)-3-amino-2-hydroxy-4-cyclohexyl)butanamide, (2RS,3R)-N-((phenylbutyryl)-3-methoxycarbonylamino-2-hydroxy-4-ethylthio)pentanamide, (2RS,3R)-N-(2-(3-pyridyl)ethyl)-3-amino-2-hydroxy-5-(methylthio)pentanamide, (2RS,3R)-3-amino-2-hydroxy-N-methyl-5-(methylsulfanyl)-N-phenethylpentanamide, (2RS,3R,1'S)-N-((2-carboxyethyl)-3-amino-2-hydroxy-4-ethylthio)pentanamide, (2RS,3R)-N-((1-methyl-1-ethoxycarboxyethyl) 3-amino-2-hydroxy-4-ethylthio)pentanamide, (2RS,3R,1'S)-N-((1-(2-hydroxy)-1-ethoxycarboxyethyl) 3-amino-2-hydroxy-4-ethylthio)pentanamide, (2RS,3R)-N-((phenylbutyryl)-3-tert-butoxycarbonylamino-2-hydroxy-4-ethylthio)pentanamide, (2RS,3R)-N-((phenylbutyryl)-3-formylamino-2-hydroxy-4-ethylthio)pentanamide, (2RS,3R)-N-Methyl-N-((ethoxycarbonylmethyl)-3-amino-2-hydroxy-4-ethylthio)pentanamide, (2RS,3R)-N-((Phenylbutyryl)-3-hydroxymethylcarbonylamino-2-hydroxy-4-ethylthio)pentanamide,
(2RS,3R,1'R)-N-((1-ethoxycarbonylethyl)-3-amino-2-hydroxy-4-ethylthio)pentanamide,
(2RS,3R,1'R)-N-((1-ethoxycarbonylethyl)-3-amino-2-hydroxy-4-cyclohexyl)butanamide,
2RS,3R)-N-((1-methyl-1-ethoxycarbonylethyl)-3-amino-2-hydroxy-4-cyclohexyl)butanamide,
(2RS,3R)-N-((Phenylbutyryl)-3-methoxycarbonylmethylamino-2-hydroxy-4-ethylthio)pentanamide,
(2RS,3R,1'S)-N-((1-ethoxycarbonylethyl)-3-amino-2-hydroxy-4-benzylthio)butanamide,
(2RS,3R,1'S)-N-((2-hydroxy-1-ethoxycarbonylethyl)-3-amino-2-hydroxy-4-cyclohexyl)butanamide,
(2RS,3R,1'S)-N-((2-acetoxypropyl)-3-amino-2-hydroxy-4-cyclohexyl)butanamide,
(2RS,3R,2'S)-N-((2-propionyloxypropyl)-3-amino-2-hydroxy-4-cyclohexyl)butanamide,
(2RS,3R,2'S)-N-((2-benzoyloxypropyl)-3-amino-2-hydroxy-4-cyclohexyl)butanamide,
(2RS,3R,2'R)-N-((2-benzoyloxypropyl)-3-amino-2-hydroxy-4-cyclohexyl)butanamide,
(2RS,3R,2'R)-N-((2-propionyloxypropyl)-3-amino-2-hydroxy-4-cyclohexyl)butanamide,
(2RS,3R,2'R)-N-((2-acetoxypropyl)-3-amino-2-hydroxy-4-cyclohexyl)butanamide,
(2RS,3R,1'S)-N-((1-benzyloxycarbonylethyl)-3-amino-2-hydroxy-4-cyclohexyl)butanamide,
(2RS,3R,1'S)-N-(4-ethoxycarbonyl-2-(1'-aminoethyl)thizole)-3-amino-2-hydroxy-4-cyclohexyl)butanamide,
(2RS,3R) N-(monodansylcadaveno)-3-amino-2hydroxy-4-cyclohexyl)butanamide,
(2RS,3R) N-(2-methyl-5-nitro imidazole-ethyl) 3-amino-2-hydroxy-4-cyclohexyl)butanamide di,
(2RS,3R) N-(5-nitropyridyl-2-aminoethyl) 3-amino-2-hydroxy-4-cyclohexyl)butanamide di,
(2RS,3R) N-(5-methoxy-tryptaminyl) 3-amino-2-hydroxy-4-cyclohexyl)butanamide,
(2RS,3R) N-(3-O-methyl-dopaminyl) 3-amino-2-hydroxy-4-cyclohexyl)butanamide,
(2RS,3R) N-(2-aminomethylbenzimidazolyl) 3-amino-2-hydroxy-4-cyclohexyl)butanamide,
((2RS,3R)-3-amino-2-hydroxy-4-cyclohexyl)butanoyl-L-alanyl-(2-methyl-5-nitroimidazolyl-ethyl)amide,
((2RS,3R)-3-amino-2-hydroxy-4-cyclohexyl)butanoyl-L-alanyl-(5-nitropyridylaminoethyl)amide,
((2RS,3R)-3-amino-2-hydroxy-4-cyclohexyl)butanoyl-L-alanyl-(ethylisonipecotate)amide,
((2RS,3R)-3-amino-2-hydroxy-4-cyclohexyl)butanoyl-L-alanyl-(2-pyrrolidinopropyl)amide,
((2RS,3R)-3-amino-2-hydroxy-4-cyclohexyl)butanoyl-L-alanyl-(5-methoxytryptamine)amide,
((2RS,3R)-3-amino-2-hydroxy-4-cyclohexyl)butanoyl-L-alanyl-(3-O-methoxydopamine)amide,
((2RS,3R)-3-amino-2-hydroxy-4-cyclohexyl)butanoyl-L-alanyl-(2-benzimidazolemethyl)amide,
((2RS,3R)-3-amino-2-hydroxy-4-cyclohexyl)butanoyl-L-alanyl-(5-phenylpyrazole-3-amide,
((2RS,3R)-3-amino-2-hydroxy-4-cyclohexyl)butanoyl-L-alanyl-(2-hydroxy-5-nitro-1)amide,
((2RS,3R)-3-amino-2-hydroxy-4-cyclohexyl)butanoyl-L-alanyl-(5-bromothizole-2-amide,
((2RS,3R)-3-amino-2-hydroxy-4-cyclohexyl)butanoyl-L-alanyl-(4-nitro-2-hydroxyphenyl-1)amide,
((2RS,3R)-3-amino-2-hydroxy-4-cyclohexyl)butanoylL-alanyl-(1-ethylpyrzole)amide,
((2RS,3R)-3-amino-2-hydroxy-4-cyclohexyl)butanoyl-(ethylisonipecotate)amide,
((2RS,3R)-3-amino-2-hydroxy-4-cyclohexyl)butanoyl-(3-imidazolylpropyl)amide,
(2RS,3R)-3-amino-2-hydroxy-4-cyclohexyl)butanoyl-(4-carboxyl-2-(1'-amino)ethyl thizole,
ethyl(2RS,3R,2'S)-2-((-3-(acetylamino)-4-cyclohexyl-2-hydroxybutanoyl)amino)propanoate,
(2RS,3R)-3-amino-2-hydroxy-4-cyclohexyl)butanoyl-(4-benzyloxycarbonylamino)butylamide,
(2RS,3R)-3-amino-2-hydroxy-4-cyclohexyl)butanoyl-beta-alanine benzyl ester,
(2RS,3R)-3-amino-2-hydroxy-4-cyclohexyl)butanoyl-monodansylcadaverine amide,
(2RS,3R)-3-amino-2-hydroxy-4-cyclohexyl)butanoyl-(4-(4-toluenesulfonyl)aminobutyl)amide,
(2RS,3R)-3-amino-2-hydroxy-4-cyclohexyl)butanoyl-(2-4-toluenesulfonylaminoethyl)amide,
(2RS,3R)-3-amino-2-hydroxy-4-cyclohexyl)butanoyl-(2-aminoethyl)amide,
(2RS,3R)-3-amino-2-hydroxy-4-cyclohexyl)butanoyl-(2-aminoethyl)amide,
(2RS,3R)-3-amino-4-cyclohexyl-2-hydroxy-N-(4-(((3-(trifluoromethyl)phenyl)sulfonyl)amino)butyl)butanamide,
(2RS,3R)-3-amino-4-cyclohexyl-N-(4-(((3,4-dimethoxyphenyl)sulfonyl)amino)butyl)-2-hydroxybutanamide,
(2RS,3R)-N-(4-(((4-acetylamino)phenyl)sulfonyl)amino)butyl)-3-amino-4-cyclohexyl-2-hydroxybutanamide,
(2RS,3R)-3-amino-4-cyclohexyl-2-hydroxy-N-(4-((2-naphthylsulfonyl)amino)butyl)butanamide,
(2RS,3R)-3-amino-2-hydroxy-4-cyclohexyl)butanoyl-L-alanine 4-sulfonamide benzyl ester,
(2RS,3R)-3-amino-2-hydroxy-4-cyclohexyl)butanoyl-L-alanine benzyl ester,
(2RS,3R)-3-amino-2-hydroxy-4-cyclohexyl)butanoyl-L-alanine cyclohexyl ester,
(2RS,3R)-3-amino-2-hydroxy-4-cyclohexyl)butanoyl-L-alanine 2-((phenylsulfonyl)methyl)benzyl ester,
(2RS,3R)-3-amino-2-hydroxy-4-cyclohexyl)butanoyl-L-alanine cyclopropyl ester(2RS,3R)-3-amino-2-hydroxy-4-cyclohexyl)butanoyl-L-alanine 4-tert-butylbenzyl ester,
(2RS,3R)-3-amino-2hydroxy-4-cyclohexyl)butanoyl-L-alanine 4-methoxycarbonylbenzyl ester,
(2RS,3R)-3-amino-2-hydroxy-4-cyclohexyl)butanoyl-L-alanine 4-trifluoromethylbenzyl ester,
(2RS,3R)-3-amino-2-hydroxy-4-cyclohexyl)butanoyl-L-alanine-(4-methyl)phenyl acetic acid phenacyl ester),
(2RS,3R)-3-amino-4-cyclohexyl-N-(2,4-dichlorobenzyl)-2-hydroxybutanamide,
(2RS,3R)-3-amino-4-cyclohexyl-2-hydroxy-N-(3-methoxyphenyl)butanamide,
methyl (2RS,3R,2'R)-2-((3-amino-4-cyclohexyl-2-hydroxybutanoyl)amino)-4-methylpentanoate, (2RS,3R)-3-amino-4-cyclohexyl-N-(2-furylmethyl)-2-hydroxybutanamide,
(2RS,3R,1'RS)-3-amino-4-cyclohexyl-2-hydroxy-N-(1-(1-naphthyl)ethyl)butanamide,
(2RS,3R)-3-amino-4-cyclohexyl-2-hydroxy-N-(3-(2-oxo-1-pyrrolidinyl)propyl)butanamide,
(2RS,3R)-3-amino-4-cyclohexyl-N-(1,2-dimethylpropyl)-2-hydroxybutanamide,
(2RS,3R)-3-amino-2-hydroxy-4-cyclohexyl)butanoyl-L-alanine,
(2RS,3R)-3-amino-2-hydroxy-4-cyclohexyl)butanoyl-L-alanine benzyl ester,
(2RS,3R)-3-amino-2-hydroxy-4-cyclohexyl)butanoyl-L-alanine,
(2RS,3R)-3-amino-4-cyclohexyl-2-hydroxy-N-phenylbutanamide,
(2RS,3R)-3-amino-N-(2-chlorophenethyl)-4-cyclohexyl-2-hydroxybutanamide,
(2RS,3R)-3-amino-4-cyclohexyl-2-hydroxy-N-(3-phenylpropyl)butanamide,
(2RS,4R)-3-amino-4-cyclohexyl-2-hydroxy-N-(1,2,3,4-tetrahydro-1-naphthalenyl)butanamide,
(2RS,3R)-3-amino-N-(4-(tert-butyl)cyclohexyl)-4-cyclohexyl-2-hydroxybutanamide,
(2RS,3R)-3-amino-4-cyclohexyl-N-(3,5-dichlorophenyl)-2-hydroxybutanamide,
(2RS,3R)-3-amino-4-cyclohexyl-N-(2-ethylhexyl)-2-hydroxybutanamide,
butyl (2RS,3R)-2-((3-amino-4-cyclohexyl-2-hydroxybutanoyl)amino)acetate,
2RS,3R)-3-amino-N-(1,3-benzodioxol-5-ylmethyl)-4-cyclohexyl-2-hydroxybutanamide,
(2RS,3R)-3-amino-4-cyclohexyl-N-(2,4-dimethoxyphenyl)-2-hydroxybutanamide,
(2RS,3R)-3-amino-4-cyclohexyl-2-hydroxy-N-(3-methoxy-5-(trifluoromethyl)phenyl)butanamide,
(2RS,3R)-3-amino-4-cyclohexyl-N-decyl-2-hydroxybutanamide,
(2RS,3R)-3-amino-N-((1R,4S)bicyclo(2.2.1)hept-2-yl)-4-cyclohexyl-2-hydroxybutanamide,
(2RS,3R)-3-amino-4-cyclohexyl-N-(2-fluorobenzyl)-2-hydroxybutanamide,
(2RS,3R)-3-amino-4-cyclohexyl-N-(4-fluoro-3-(trifluoromethyl)benzyl)-2-hydroxybutanamide,
(2RS,3R)-3-amino-4-cyclohexyl-N-(1-(4-fluorophenyl)ethyl)-2-hydroxybutanamide,
(2RS,3R)-3-amino-4-cyclohexyl-2-hydroxy-N-(tetrahydro-2-furanylmethyl)butanamide,
ethyl (2RS,3R)0(4-((-3-amino-4-cyclohexyl-2-hydroxybutanoyl)amino)-1-piperidinecarboxylate,
(2RS,3R)-3-amino-N-(1,3-benzodixol-5-yl)-4-cyclohexyl-2-hydroxybutanamide,
tert-butyl (2RS,3R)-2-((3-amino-4-cyclohexyl-2-hydroxybutanoyl)amino)acetate,
methyl (2RS,3R)-2-((3-amino-4-cyclohexyl-2-hydroxybutanoyl)amino)-3-phenylpropanoate,
methyl (2RS,3R,2'S)-2-((3-amino-4-cyclohexyl-2-hydroxybutanoyl)amino)-3-methylpentanoate,
methyl (2RS,3R,2')-2-((3-amino-4-cyclohexyl-2-hydroxybutanoyl)amino)hexanoate,
methyl (2RS,3R)-2-((3-amino-4-cyclohexyl-2-hydroxybutanoyl)amino)-3-methylbutanoate,
(2RS,3R)-3-amino-4-cyclohexyl-2-hydroxy-N-((1S)-1-(2-naphthyl)ethyl)butanamide,
(2RS,3R)-3-amino-4-cyclohexyl-2-hydroxy-N-((1R)-1-(2-naphthyl)ethyl)butanamide,
(2RS,3R)-3-amino-4-cyclohexyl-2-hydroxy-N-((1S)-1-(1-naphthyl)ethyl)butanamide,
(2RS,3R)-3-amino-4-cyclohexyl-2-hydroxy-N-((1R)-1-(1-naphthyl)ethyl)butanamide,
ethyl (2RS,3R,2'R)-2-((3-amino-4-cyclohexyl-2-hydroxybutanoyl)amino)-3-fluoropropanoate,
(2RS,3R)-3-amino-4-cyclohexyl-2-hydroxy-N-(2-hydroxy-1-(hydroxymethyl)ethyl)butanamide,
4-(tert-butyl)benzyl (2RS,3R,2'R)-2-((3-amino-4-cyclohexyl-2-hydroxybutanoyl)amino)-3-hydroxypropanoate,
4-nitrobenzyl (2RS,3R,2'S)-2-((3-amino-4-cyclohexyl-2-hydroxybutanoyl)amino)-3-hydroxypropanoate,
3-nitrobenzyl (2RS,3R,2'S)-2-((3-amino-4-cyclohexyl-2-hydroxybutanoyl)amino)-3-hydroxypropanoate,
4-(trifluoromethyl)benzyl (2RS,3R,2'S)-2-((3-amino-4-cyclohexyl-2-hydroxybutanoyl)amino)-3-hydroxypropanoate,
3-(trifluoromethoxy)benzyl (2RS,3R,2'S)-2-((3-amino-4-cyclohexyl-2-hydroxybutanoyl)amino)-3-hydroxypropanoate,
(2RS,3R)-3-amino-4-cyclohexyl-N-(4-fluorophenethyl)-2-hydroxybutanamide,
(2RS,3R)-3-amino-4-cyclohexyl-2-hydroxy-N-(4-methylphenyl)butanamide,
(2RS,3R)-3-amino-4-cyclohexyl-N-(4-fluorophenyl)-2-hydroxybutanamide,
(2RS,3R)-3-amino-4-cyclohexyl-2-hydroxy-N-(4-methoxyphenyl)butanamide,
(2RS,3R)-3-amino-4-cyclohexyl-2-hydroxy-N-(2-methoxyphenyl)butanamide,
(2RS,3R)-3-amino-N-(4-chlorophenyl)-4-cyclohexyl-2-hydroxybutanamide,
(2RS,3R)-3-amino-N-(3-chlorophenyl)-4-cyclohexyl-2-hydroxybutanamide,
(2RS,3R)-3-amino-N-(2-chlorophenyl)-4-cyclohexyl-2-hydroxybutanamide,
(2RS,3R)-3-amino-N-(4-tert-butyl)phenyl)-4-cyclohexyl-2-hydroxybutanamide,
(2RS,3R)-3-amino-4-cyclohexyl-2-hydroxy-N-(3-(trifluoromethyl)phenyl)butanamide,
(2RS,3R)-3-amino-4-cyclohexyl-2-hydroxy-N-(4-(trifluoromethyl)phenyl)butanamide,
(2RS,3R)-3-amino-4-cyclohexyl-N-(3,4-dichlorophenyl)-2-hydroxybutanamide,
(2RS,3R)-3-amino-4-cyclohexyl-N-(2,4-dichlorophenyl)-2-hydroxybutanamide,
(2RS,3R)-3-amino-N-(4-bromophenyl)-4-cyclohexyl-2-hydroxybutanamide,
(2RS,3R)-3-amino-N-(4-tert-butyl)benzyl)-4-cyclohexyl-2-hydroxybutanamide,
(2RS,3R)-3-amino-4-cyclohexyl-2-hydroxy-N-(3-(trifluoromethyl)benzyl)butanamide,
(2RS,3R)-3-amino-4-cyclohexyl-2-hydroxy-N-(4-(trifluoromethyl)benzyl)butanamide,
(2RS,3R)-3-amino-N-(2-chlorobenzyl)-4-cyclohexyl-2-hydroxybutanamide,
(2RS,3R)-3-amino-4-cyclohexyl-2-hydroxy-N-(2-methoxy-5-nitrophenyl)butanamide,
(2RS,3R)-3-amino-4-cyclohexyl-N-(3,5-dimethoxyphenyl)-2-hydroxybutanamide,
(2RS,3R)-3-amino-4-cyclohexyl-2-hydroxy-N-(3-phenoxyphenyl)butanamide, (((2RS,3R)-3-amino-4-cyclohexyl-2-hydroxybutanoyl) amino)(2,5-dimethoxybenzyl)chloronium, (2RS,3R)-3-amino-4-cyclohexyl-N-(2,4-dichlorophenethyl)-2-hydroxybutanamide, (2RS,3R)-3-amino-4-cyclohexyl-N-(2,6-dichlorophenethyl)-2-hydroxybutanamide, (2RS,3R)-3-amino-4-cyclohexyl-N-(3-fluorophenethyl)-2-hydroxybutanamide, (2RS,3R)-3-amino-N-(3,4-bis(benzyloxy)phenethyl)-4-cyclohexyl-2-hydroxybutanamide, (2RS,3R)-3-amino-4-cyclohexyl-2-hydroxy-N-(4-phenoxyphenethyl)butanamide, (2RS,3R)-3-amino-4-cyclohexyl-2-hydroxy-N-(2-(trifluoromethoxy)phenyl)butanamide, (2RS,3R)-3-amino-4-cyclohexyl-2-hydroxy-N-(3-(trifluoromethoxy)phenyl)butanamide, (2RS,3R)-3-amino-4-cyclohexyl-2-hydroxy-N-(2-methylphenyl)butanamide, (2RS,3R)-3-amino-4-cyclohexyl-N-(2,6-dimethylphenyl)-2-hydroxybutanamide, (2RS,3R)-3-amino-4-cyclohexyl-2-hydroxy-N-(4-iodo-2-methylphenyl)butanamide, (2RS,3R)-3-amino-N-(4-anilino-2-methoxyphenyl)-4-cyclohexyl-2-hydroxybutanamide, (2RS,3R)-3-amino-4-cyclohexyl-N-(2-ethoxyphenyl)-2-hydroxybutanamide, (2RS,3R)-3-amino-N-(4-chloro-2-methoxy-5-methylphenyl)-4-cyclohexyl-2-hydroxybutanamide, (2RS,3R)-3-amino-4-cyclohexyl-N-(2,5-dimethoxyphenyl)-2-hydroxybutanamide, (2RS,3R)-N-(5-acetylamino)-2-methoxyphenyl)-3-amino-4-cyclohexyl-2-hydroxybutanamide, (2RS,3R)-3-amino-4-cyclohexyl-2-hydroxy-N-(2-methoxydibenzo(b,d)furan-3-yl)butanamide, (2RS,3R)-3-amino-N-(5-chloro-2,4-dimethoxyphenyl)-4-cyclohexyl-2-hydroxybutanamide, (2RS,3R)-3-amino-4-cyclohexyl-N-(2,5-diethoxyphenyl)-2-hydroxybutanamide, (2RS,3R)-3-amino-N-(5-tert-butyl)-2-methoxyphenyl)-4-cyclohexyl-2-hydroxybutanamide, (2RS,3R)-3-amino-4-cyclohexyl-2-hydroxy-N-(2-phenoxyphenyl)butanamide, (2RS,3R)-3-amino-4-cyclohexyl-2-hydroxy-N-(2-methyl-5-nitrophenyl)butanamide, (2RS,3R)-3-amino-4-cyclohexyl-2-hydroxy-N-(4-phenoxyphenyl)butanamide, (2RS,3R)-3-amino-4-cyclohexyl-2-hydroxy-N-(4-methoxybenzyl)butanamide, (2RS,3R)-3-amino-4-cyclohexyl-2-hydroxy-N-(4-methylbenzyl)butanamide, (2RS,3R)-3-amino-N-(3-chlorobenzyl)-4-cyclohexyl-2-hydroxybutanamide, (2RS,3R)-3-amino-4-cyclohexyl-2-hydroxy-N-(3-methoxybenzyl)butanamide, (2RS,3R)-3-amino-N-(4-bromobenzyl)-4-cyclohexyl-2-hydroxybutanamide, (2RS,3R)-3-amino-4-cyclohexyl-2-hydroxy-N-(3-methylbenzyl)butanamide, (2RS,3R)-3-amino-4-cyclohexyl-2-hydroxy-N-phenethylbutanamide, (2RS,3R)-3-amino-N-(4-chlorobenzyl)-4-cyclohexyl-2-hydroxybutanamid, (2RS,3R)-3-amino-4-cyclohexyl-2-hydroxy-N-(4-methylphenethyl)butanamide, (2RS,3R)-3-amino-4-cyclohexyl-2-hydroxy-N-(4-methoxyphenethyl)butanamide, (2RS,3R)-3-amino-4-cyclohexyl-2-hydroxy-N-(3-methoxyphenethyl)butanamide, (2RS,3R)-3-amino-4-cyclohexyl-2-hydroxy-N-(2-methoxyphenethyl)butanamide, (2RS,3R)-3-amino-N-(4-chlorophenethyl)-4-cyclohexyl-2-hydroxybutanamide, (2RS,3R)-3-amino-N-(3-chlorophenethyl)4-cyclohexyl-2-hydroxybutanamide, (2RS,3R)-3-amino-4-cyclohexyl-2-hydroxy-N-(3-(trifluoromethyl)phenethyl)butanamide, (2RS,3R)-3-amino-N-(4-bromophenethyl)4-cyclohexyl-2-hydroxybutanamide, (2RS,3R)-N-(1-adamantyl)-3-amino-4-cyclohexyl-2-hydroxybutanamide, (2RS,3R)-N-(2-adamantyl)-3-amino-4-cyclohexyl-2-hydroxybutanamide, (2RS,3R)-3-amino-N-cycloheptyl-4-cyclohexyl-2-hydroxybutanamide, (2RS,3R)-3-amino-4-cyclohexyl-N-(cyclohexylmethyl)-2-hydroxybutanamide, (2RS,3R)-3-amino-N,4-dicyclohexyl-2-hydroxybutanamide, (2RS,3R)-3-amino-4-cyclohexyl-N-cyclopentyl-2-hydroxybutanamide, (2RS,3R)-3-amino-N-cyclobutyl-4-cyclohexyl-2-hydroxybutanamide, (2RS,3R)-3-amino-4-cyclohexyl-2-hydroxy-N-(1-methyl-3-phenylpropyl)butanamide, (2RS,3R)-3-amino-4-cyclohexyl-2-hydroxy-N-(1-methyl-2-(3-(trifluoromethyl)phenyl)ethyl)butanamide, (2RS,3R)-3-amino-4-cyclohexyl-N-(1,5-dimethylhexyl)-2-hydroxybutanamide, (2RS,3R)-3-amino-4-cyclohexyl-2-hydroxy-N-(1-methylhexyl)butanamide, (2RS,3R)-3-amino-4-cyclohexyl-2-hydroxy-N-(3-isopropoxypropyl)butanamide, (2RS,3R)-3-amino-4-cyclohexyl-2-hydroxy-N-(3-isobutoxypropyl)butanamide, (2RS,3R)-3-amino-4-cyclohexyl-2-hydroxy-N-(4(4-morpholinyl)phenyl)butanamide, (2RS,3R)-3-amino-4-cyclohexyl-N-(3,3-diphenylpropyl)-2-hydroxybutanamide, (2RS,3R)-3-amino-4-cyclohexyl-N-(1,4-dimethylpentyl)-2-hydroxybutanamide, (2RS,3R)-3-amino-4-cyclohexyl-2-hydroxy-N-methyl-N-(1-naphthylmethyl)butanamide, (2RS,3R)-3-amino-4-cyclohexyl-2-hydroxy-N-methyl-N-((1S)-1-(1-naphthyl)ethyl)butanamide, (2RS,3R)-3-amino-4-cyclohexyl-2-hydroxy-N-(2-methoxy-5-(trifluoromethyl)phenyl)butanamide, (2RS,3R)-3-amino-4-cyclohexyl-2-hydroxy-N-(4-methoxy(1,1'-biphenyl)-3-yl)butanamide, (2RS,3R)-3-amino-4-cyclohexyl-N-(2,3-dihydro-1,4-benzodioxin-6-yl)-2-hydroxybutanamide, (2RS,3R)-3-amino-N-(3-(benzyloxy)phenyl)-4-cyclohexyl-2-hydroxybutanamide, (2RS,3R)-3-amino-4-cyclohexyl-N-(3-ethoxyphenyl)-2-hydroxybutanamide, (2RS,3R)-3-amino-4-cyclohexyl-2-hydroxy-N-(3,4,5-trimethoxyphenyl)butanamide, (2RS,3R)-3-amino-4-cyclohexyl-N-)2-(2-fluorophenyl)-1-methylethyl)-2-hydroxybutanamide, (2RS,3R)-3-amino-4-cyclohexyl-N-(2-(4-fluorophenyl)-1,1-dimethylethyl)-2-hydroxybutanamide, (2RS,3R)-3-amino-4-cyclohexyl-N-(2,3-dihydro-1H-inden-1-yl)-2-hydroxybutanamide, (2RS,3R)-3-amino-4-cyclohexyl-2-hydroxy-N-((1S,2R)-2-phenylcyclopropyl)butanamide, (2RS,3R)-3-amino-4-cyclohexyl-2-hydroxy-N-(1,1,3,3-tetramethylbutyl)butanamide, (2RS,3R)-3-amino-4-cyclohexyl-N-(1,3-dimethylbutyl)-2-hydroxybutanamide, methyl 4-(((2RS,3R)-3-amino-4-cyclohexyl-2-hydroxybutanoyl)amino)-3-thiophenecarboxylate, (2RS,3R)-N-(1-(1-adamantyl)ethyl)-3-amino-4-cyclohexyl-2-hydroxybutanamide, (2RS,3R)-3-amino-2-hydroxy-4-cyclohexyl)butanoyl-((S)-(-)-(1-naphthyl)ethyl)amide, (2RS,3R)-3-amino-4-ethylthio-2-hydroxy-N-(1-naphthylmethyl)butanamide, (2RS,3R)-3-amino-4-cyclohexyl-2-hydroxy-N-(3-(trifluoromethoxy)benzyl)butanamide, (2RS,3R)-3amino-N-(3,5-bis(trifluoromethyl)benzyl)-4-cyclohexyl-2-hydroxybutanamide, (2RS,3R)-3-amino-4-cyclohexyl-2-hydroxy-N-(2-(trifluoromethyl)benzyl)butanamide, (2RS,3R)-3-amino-4-cyclohexyl-2-hydroxy-N-(4-(trifluoromethoxy)benzyl)butanamide, (2RS,3R)-3-amino-N-(6-chloro-3-pyridinyl)-4-cyclohexyl-2-hydroxybutanamide, (2RS,3R)-3-amino-4-cyclohexyl-2-hydroxy-N-(6-methyl-2-pyridinyl)butanamide, (2RS,3R)-3-amino-N-(5chloro-2-methoxyphenyl)-4-cyclohexyl-2-hydroxybutanamide, (2RS,3R)-3-amino-4-cyclohexyl-2-hydroxy-N-(2-methoxy-5-methylphenyl)butanamide, (2RS,3R)-3-amino-N-(4-chloro-2,5-dimethoxyphenyl)-4-cyclohexyl-2-hydroxybutanamide, (2RS,3R)-3-amino-4-cyclohexyl-N-(2,3-dimethoxyphenyl)-2-hydroxybutanamide, (2RS,3R)-3-amino-4-cyclohexyl-N-(3,4-dimethoxyphenyl)-2hydroxybutanamide, (2RS,3R)-3-amino-4-cyclohexyl-2-hydroxy-N-(3-methoxy-4-methylphenyl)butanamide, (2RS,3R)-3-amino-4-cyclohexyl-2-hydroxy-N-(4-methoxy-2-naphthyl)butanamide, (2RS,3R)-3-amino-4-cyclohexyl-2-hydroxy-N-(2-thienylmethyl)butanamide, (2RS,3R)-3-amino-N-butyl-4-cyclohexyl-2-hydroxy-N-methylbutanamide, (2RS,3R)-3-amino-4-cyclohexyl-1-(2,6-dimethyl-4-morpholinyl)-2-hydroxy-1-butanone, (2RS,3R)-3-amino-4-cyclohexyl-2-hydroxy-N,N-bis(methoxymethyl)butanamide, (2RS,3R)-3-amino-4-cyclohexyl-1-[3,4-dihydro-2(1H)-isoquinolinyl]-2-hydroxy-1-butanone, (2RS,3R)-3-amino-1-(1-azepanyl)-4-cyclohexyl-2-hydroxy-1-butanone, (2RS,3R)-3-amino-4-cyclohexyl-2-hydroxy-1-[4-phenyl-3,6-dihydro-1(2H)-pyridinyl]-1-butanone (2RS,2R)-3-amino-N-benzyl-N-butyl-4-cyclohexyl-2-hydroxybutanamide (2RS,3R)-3-amino-4-cyclohexyl-1-[(2R,6S)-2,6-dimethylmorpholinyl]-2-hydroxy-1-butanone, (2RS,3R)-3-amino-N-[(2-chloro-2,3,5-cyclohexatrien-1-yl)methyl]-4-cyclohexyl-2-hydroxy-N-methylbutanamide, (2RS,3R)-3-amino-N-(1,3-benzodioxol-5-ylmethyl)-4-cyclohexyl-2-hydroxy-N-methylbutanamide, (2RS,3R)-3-amino-4-cyclohexyl-N-(2,4-dichlorobenzyl)-N-ethyl-2-hydroxybutanamide, ethyl 3-[[(2RS,3R)-3-amino-4-cyclohexyl-2-hydroxybutanoyl](benzyl)amino]propanoate, and (2RS,3R)-3-amino-4-cyclohexyl-2-hydroxy-1-(1-piperidinyl)-1-butanone.

or a pharmaceutically acceptable salt, ester, or prodrug thereof.

Biological Assay

The ability of compounds of the present invention to inhibit methionine aminopeptidase 2 was evaluated using the following assay.

Recombinant methionine aminopeptidase-2 (MetAP2) was expressed as a secreted protein with a baculovirus system and purified from the insect cell culture supernatant as previously described by R. L. Kendal, et al., *J. Biol. Chem.*, 267(29): 20667–20673 (1992) and Xuan Li, et al., *Biochem. And Biophys. Res. Comm.*, 227: 152–159 (1996), the contents of which are incorporated herein by reference.

Assays for MetAP2 enzyme activity and MetAP2 inhibition were performed in 96-well microtiter plates. Compounds to be tested for MetAP2 inhibition were dissolved in dimethyl-sulfoxide at 10 mM and diluted ten-fold in assay buffer (50 nM HEPES, pH 7.4, 100 mM NaCl). Ten microliters of solution of each compound to be tested for inhibition were introduced into each cell of the plate, with each compound being tested in triplicate. Zero inhibition of enzyme activity was taken to be the result obtained in cells in which 10 mL of assay buffer was placed, and 100 percent inhibition of enzyme activity was taken to be the result obtained in cells in which 10 mM of fumagillin (Sigma Chemical Co., St. Louis, Mo., USA, Catalog No. F-6771) in assay buffer was placed.

A mixture totaling 90 $\mu$L per well, and made up of of 84 mL of assay buffer, 1 $\mu$L of L-amino acid oxidase (Sigma Catalog No. A-9378, ~11 mg/mL), 1 $\mu$L of horseradish peroxidase (Sigma Catalog No. P-8451, dissolved in assay buffer at a concentration of 10 mg/mL), 1 $\mu$L of the tripeptide Met—Ala—Ser (Bachem), dissolved in assay buffer at concentration of 50 mM), 1 mL of ortho-dianisidine (Sigma Catalog No. D-1954, freshly made solution in water at a concentration of 10 mg,mL), and MetAP2 at a final concentration of 4 $\mu$g/mL was rapidly mixed and added to each cell containing test or control compound. The absorbence at 450 nanometers was measured every 20 seconds over a period of twenty minutes using an automaic plate reader (Molecular Devices, CA, USA). The $V_{max}$ in mOD/min, calculated for each well was used to represent MetAP2 activity. The $IC_{50}$ for each inhibitor was obtained by plotting the remaining MetAP2 activity versus inhibitor concentration. The results of these tests appear in Table 1.

TABLE 1

Inhibition of MetAP2 Activity by Representative Compounds of the Invention

| Example | $IC_{50}(\mu M)$ | Example | $IC_{50}(\mu M)$ |
| --- | --- | --- | --- |
| 1 | 11. | 126 | 13. |
| 2 | 47. | 127 | 28. |
| 3 | 10. | 128 | 14. |
| 4 | 2.4 | 129 | 27. |
| 5 | 2.6 | 130 | 4.3 |
| 6 | 3.0 | 131 | 0.99 |
| 7 | 2.0 | 132 | 4.1 |
| 8 | 2.3 | 133 | 0.27 |
| 9 | 2.3 | 134 | 3.1 |
| 10 | 3.6 | 135 | 3.2 |
| 11 | 2.6 | 136 | 1.8 |
| 12 | 0.86 | 137 | 8.4 |
| 13 | 1.1 | 138 | 1.6 |
| 14 | 0.72 | 139 | 1.7 |
| 15 | 0.72 | 140 | 2.2 |
| 16 | 0.78 | 141 | 3.7 |
| 17 | 1.4 | 142 | 0.40 |
| 18 | 0.15 | 143 | 0.87 |
| 19 | 1.6 | 144 | 2.1 |
| 20 | 5.8 | 145 | 1.2 |

TABLE 1-continued

Inhibition of MetAP2 Activity by
Representative Compounds of the Invention

| Example | IC$_{50}$($\mu$M) | Example | IC$_{50}$($\mu$M) |
|---|---|---|---|
| 21 | 14. | 146 | 1.5 |
| 22 | 3.4 | 147 | 1.0 |
| 23 | 1.3 | 148 | 0.52 |
| 24 | 1.0 | 149 | 0.93 |
| 25 | 1.9 | 150 | 3.1 |
| 26 | 4.7 | 151 | 0.43 |
| 27 | 1.7 | 152 | 2.4 |
| 28 | 100 | 153 | 0.37 |
| 29 | 100 | 154 | 1.9 |
| 30 | 1.1 | 155 | 052 |
| 31 | 100 | 156 | 3.9 |
| 32 | 1.4 | 157 | 1.6 |
| 33 | 2.5 | 158 | 2.8 |
| 34 | 3.1 | 159 | 1.5 |
| 35 | 0.11 | 160 | 0.90 |
| 36 | 0.14 | 161 | 0.62 |
| 37 | 16. | 162 | 1.2 |
| 38 | 100 | 163 | 0.48 |
| 39 | 5.1 | 164 | 0.65 |
| 40 | 81 | 165 | 0.26 |
| 41 | .09 | 166 | 0.59 |
| 42 | 2.8 | 167 | 3.3 |
| 43 | 6.8 | 168 | 1.5 |
| 44 | 13 | 169 | 3.3 |
| 45 | 5.2 | 170 | 1.0 |
| 46 | 1.1 | 171 | 0.95 |
| 47 | 1.5 | 172 | 5.0 |
| 48 | 1.5 | 173 | 0.58 |
| 49 | 2.2 | 174 | 1.5 |
| 50 | 3.7 | 175 | 2.1 |
| 51 | 5.0 | 176 | 3.4 |
| 52 | 6.1 | 177 | 2.0 |
| 53 | 1.8 | 178 | 11. |
| 54 | 2.6 | 179 | 4.9 |
| 55 | 2.7 | 180 | 2.0 |
| 56 | 12. | 181 | 9.8 |
| 57 | 3.1 | 182 | 8.0 |
| 58 | 3.5 | 183 | 8.7 |
| 59 | 1.5 | 184 | 0.43 |
| 60 | 18. | 185 | 1.8 |
| 61 | 13. | 186 | 1.1 |
| 62 | 7.6 | 187 | 1.2 |
| 63 | 20. | 188 | 1.6 |
| 64 | 19 | 189 | 1.5 |
| 65 | 5.6 | 190 | 1.3 |
| 66 | 10. | 191 | 2.5 |
| 67 | 13. | 192 | 1.2 |
| 68 | 3.8 | 193 | 2.5 |
| 69 | 5.3 | 194 | 1.4 |
| 70 | 5.4 | 195 | 1.3 |
| 71 | 12. | 196 | 0.82 |
| 72 | 9.2 | 197 | 0.58 |
| 73 | 6.8 | 198 | 0.84 |
| 74 | 30. | 199 | 1.0 |
| 75 | 9.4 | 200 | 1.5 |
| 76 | 100 | 201 | 0.71 |
| 77 | 3.3 | 202 | 8.3 |
| 78 | 1.8 | 203 | 4.9 |
| 79 | 0.10 | 204 | 3.8 |
| 80 | 1.3 | 205 | 2.5 |
| 81 | 1.8 | 206 | 10. |
| 82 | 38. | 207 | 4.1 |
| 83 | 26. | 208 | 2.7 |
| 84 | 3.3 | 209 | 14. |
| 85 | 3.2 | 210 | 2.3 |
| 86 | 1.7 | 211 | 2.4 |
| 87 | 2.7 | 212 | 1.7 |
| 88 | 2.2 | 213 | 2.6 |
| 89 | 6.6 | 214 | 2.8 |
| 90 | 2.3 | 215 | 1.3 |
| 91 | 2.3 | 216 | 1.8 |
| 92 | 1.4 | 217 | 1.8 |
| 93 | 5.4 | 218 | 0.46 |
| 94 | 0.91 | 219 | 1.8 |
| 95 | 5.2 | 220 | 5.5 |
| 96 | 2.9 | 221 | 5.4 |
| 97 | 3.0 | 222 | 0.20 |
| 98 | 0.58 | 223 | 0.88 |
| 99 | 35 | 224 | 0.43 |
| 100 | 5.9 | 225 | 0.35 |
| 101 | 0.31 | 226 | 0.97 |
| 102 | 13 | 227 | 0.88 |
| 103 | 100 | 228 | 0.93 |
| 104 | 28 | 229 | 1.2 |
| 105 | 19. | 230 | 34. |
| 106 | 100 | 231 | 2.5 |
| 107 | 1.2 | 232 | 100 |
| 108 | 0.63 | 233 | 2.7 |
| 109 | 1.7 | 235 | 0.97 |
| 110 | 1.0 | 236 | 1.9 |
| 111 | 8.2 | 237 | 5.1 |
| 112 | 1.5 | 238 | 2.7 |

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waves; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ration of drug to polymer and the nature of the particular polymer employed, the rate of drug release can be controlled. Examples of the biodegradable polymers include poly(orthoesters) and poly(anhydrides). Depot injectable formulations are also prepared by entrapping the drug in liposomes or microemulsions which are compatible with body tissues. Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluoro-hydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Therapeutic Administration

According to the methods of treatment of the present invention, disorders caused by undesirable angiogenesis are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to inhibit angiogenesis, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. However, a well-known technique utilized by medical practitioners is to "dose titrate" the patient; that is, to start with dose lower than that required to obtain the desired effect, and to gradually increase the dose until the desired therapeutic benefit is obtained.

The total daily dose of the compounds of this invention administered to a human or other mammal in single or in divided doses can be in amounts, for example, from 0.01 to 50 mg/kg body weight or more usually from 0.11 to 25 mg/kg body weight. Single dose compositions may contain such amounts or submultiples thereof to make up the daily dose. In general, treatment regiments according to the present invention comprise administration to a patient in need of such treatment from about 1 mg to about 500 mg of the compound(s) of this invention per day in single or multiple doses.

General Synthetic Methods

As shown in Reaction Scheme 1, 3-amino-2-hydroxy-carboxylic acids used as starting materials for the synthesis of compounds of the present invention are available from appropriately substituted alpha-aminoacids by conversion to the corresponding aminoaldehyde, formation of the corresponding cyanohydrin, and hydrolysis. Protection of the free amino group, for example with a tert-butyl carbamate group, followed by coupling with an appropriate amine, amino acid derivative, or alcohol and deprotection provides the target compounds. The coupling partners may be purchased from commercial sources or prepared using known chemical transformations. Subsequent conversion of the 3-amino-2-hydroxy compounds to compounds of the present invention are by standard methods well known to practitioners of the organic chemical arts and are illustrated by the Examples which appear below.

Scheme 1

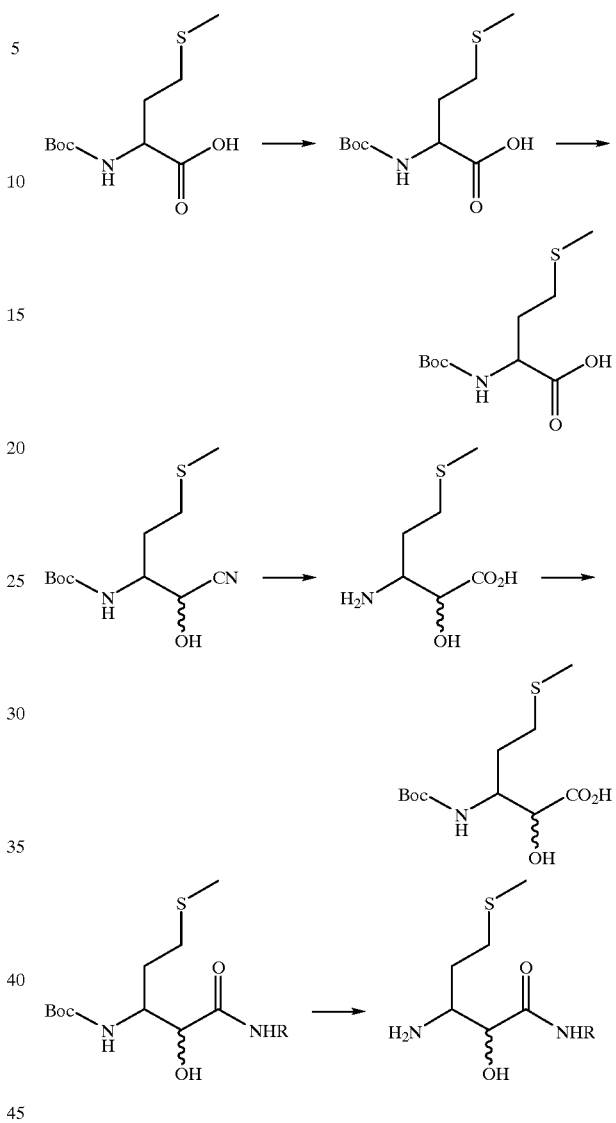

The compounds and processes of the present invention will be better understood in connection with the following examples, which are intended as an illustration of and not a limitation upon the scope of the invention.

Example 1

(2RS,3S,1'S)-N-((1-ethoxycarbonyl)ethyl)-3-amino-2-hydroxy-5-(methylthio)pentanamide hydrochloride Example 1A A solution of N-(tert-butoxycarbonyl)-L-methionine (12.47 g, 50 mmol) and REDAL (50 mmol) in dry toluene (125 mL) was stirred at 0° C. for 30 minutes, then at ambient temperature for 1 hour. The mixture was treated with aqueous Rochelle salt and extracted with ethyl ether. The extract was washed sequentially with brine and aqueous NaHCO$_3$, dried (MgSO$_4$), and concentrated to give a colorless syrup (9.05 g).

Example 1B

A solution of the product of example 1A (9.05 g, 38.5 mmol), sulfur trioxide pyridine complex (30.64 g, 192.5 mmol) and triethylamine (26.8 mL, 192.5 mmol) in DMSO (30 mL) was stirred at ambient temperature for 30 minutes, cooled to 0° C., then treated sequentially with water (20 mL) and saturated aqueous $KHSO_4$ (120 mL), and extracted with ethyl acetate. The extract was washed sequentially with saturated aqueous $KHSO_4$ and brine, dried ($MgSO_4$), and concentrated to give a colorless syrup (9.00 g).

Example 1C

A solution of the product of example 1B (9.00 g, 38.5 mmol), and sodium bisulfite (3.80 g, 36.6 mmol) in water (200 mL) was stirred at 5° C. for 72 hours, warmed to ambient temperature, then treated with potassium cyanide (2.51 g, 38.6 mmol) in ethyl acetate (250 mL) for 4 hours. The separated ethyl acetate layer was washed sequentially with water and brine, dried ($MgSO_4$), and concentrated to give a colorless syrup, which was dissolved in dioxane (75 mL) and 12 N HCl (75 mL), then heated at reflux for 16 h. The mixture was concentrated in vacuo and redissolved in water (8 mL) and acetone (300 mL), the pH adjusted to 5.5 with 1 N NaOH, and the resulting solid collected by filtration and dried to provide 5.81 g solid material.

MS (ESI+Q1MS) m/e 180: $(M+H)^+$, 202 $(M+Na)^+$; (ESI-Q1MS) m/e: 178 $(M-H)^-$ $^1$H NMR (300 MHz, $D_2O$) δ4.25 (d, 0.5H), 4.14 (d, 0.5H), 3.78 (m, 0.5H), 3.66 (m, 0.5H), 2.65 (m, 2H), 2.13 (s, 1.5H), 2.09 (s, 1.5H), 1.93 (m, 2H).

Example 1D

A solution of the product of example 1C (5.81 g, 32.4 mmol), BOC-ON (9.58 g, 38.9 mmol) and triethylamine (6.77 mL, 48.6 mmol) in water (70 mL) and dioxane (70 mL) was stirred at 45° C. for 5 hours, diluted with ethyl acetate and 10% aqueous $KHSO_4$ then extracted with ethyl acetate. The extract was washed sequentially with water and brine, dried ($MgSO_4$), and concentrated to give (2RS,3S) 3-(tert-butoxycarbonylamino)-2-hydroxy-5-(methylthio) pentanoic acid. (4.05 g).

MS (ESI+Q1MS) m/e 280: $(M+H)^+$, 302 $(M+Na)^+$, 581 $(2M+Na)^+$; (ESI−Q1MS) m/e 278: (M−H).

Example 1E

A solution of example 1D (2.79 g, 10 mmol), L-alanine ethylester hydrochloride (1.84 g, 12 mmol), EDCI (2.30 g, 12 mmol), HOBT (1.84 g, 12 mmol) and NMM (1.32 mL, 12 mmol) in $CH_2Cl_2$ (35 mL) was stirred at ambient temperature for 16 hours, evaporated to dryness, redissolved in ethyl acetate then washed sequentially with aqueous $NaHCO_3$, brine, 10% aqueous $KHSO_4$ and brine, dried ($MgSO_4$), and concentrated. The residue was purified by flash chromatography on silica gel with 50% ethyl acetate/toluene to provide the designated compound (2.74 g).

MS (ESI+Q1MS) m/e 379 $(M+H)^+$, 396 $(M+Na)^+$, 279 $(M+H-BOC)^+$.

Example 1F

A solution of the product of example 1E (0.40 g, 1.1 mmol), in hydrogen chloride saturated dioxane (8 mL) was stirred at ambient temperature for 1 hour, evaporated to dryness, suspended in ethyl ether then concentrated and vacuum dried to give the title compound (0.24 g).

MS (ESI+Q1MS) m/e 279 $(M+H)^+$, 557 $(2M+H)^+$;

$^1$H NMR (300 MHz, DMSO-$d_6$) δ 8.46 (d, 0.6H), 8.43 (d, 0.4H), 8.14 (br. 1H), 7.97 (br., 1H), 6.63 (d, 0.6H), 6.51 (d, 0.4H), 4.05–4.38 (m, 5H), 2.42–2.67 (m, 2H), 2.04 (s, 1.8H), 2.01 (s, 1.2H), 1.65–1.96 (m, 2H), 1.35 (d, 0.6H), 1.33 (d, 1.2H), 1.17–1.23 (dt, 1.8H).

Example 2

(2RS,3S,1'S)-N-((1-Ethylcarboxamido)ethyl)-3-amino-2-hydroxy-5-(methylthio)pentanamide hydrochloride The product of example 1D and alanine ethylamide were processed as in examples 1E and 1F to provide the title compound.

MS (ESI+Q1MS) m/e 278 $(M+H)^+$, 300 $(M+Na)^+$;

$^1$H NMR (300 MHz, $D_2O$) δ 4.28–4.52 (m, 2H), 3.83–3.88 (m, 0.5H), 3.72–3.78 (m, 0.5H), 3.22 (q, 2H), 2.52–2.73 (m, 2H), 1.83–2.17 (m, 5H), 1.41 (d, 3H), 1.11 (t, 1.5H), 1.10 (t, 1.5H).

Example 3

(2RS,3R,1'S)-N-((1-Ethylcarboxamido)ethyl)-3-amino-2-hydroxy-5-(methylthio)pentanamide hydrochloride

Example 3A

N-(tert-butoxycarbonyl)-D-methionine was processed as in examples 1A through 1D to provide (2RS,3R) 3-(tert-butoxycarbonylamino)-2-hydroxy-5-(methylthio)pentanoic acid.

Example 3B

The product of example 3A and L-alanine ethylamide were processed as in example 2 to provide the title compound.

MS (ESI+Q1MS) m/e 278 $(M+H)^+$, 300 $(M+Na)^+$;

$^1$H NMR (300 MHz, $D_2O$) δ 4.27–4.52 (m, 2H), 3.85–3.92 (m, 0.5H), 3.74–3.81 (m, 0.5H), 3.17–3.26 (m, 2H), 2.52–2.74 (m, 2H), 1.85–2.17 (m, 5H), 1.42 (d, 3H), 1.12 (t, 3H).

Example 4

(2RS,3R,1'S)-N-((1-ethoxycarbonyl)ethyl)-3-amino-2-hydroxy-5-(methylthio)pentanamide hydrochloride The product of example 3A and L-alanine ethylester hydrochloride were processed as in example 2 to provide the title compound.

MS (ESI+Q1MS) m/e 279 $(M+H)^+$, 301 $(M+Na)^+$;

$^1$H NMR (300 MHz, $D_2O$) δ 4.37–4.53 (m, 2H), 3.86–3.93 (m, 0.4H), 3.73–3.78 (m, 0.6H), 2.53–2.77 (m, 2H), 1.89–2.17 (m, 5H), 1.48 (d, 3H), 1.28 (t, 3H).

Example 5

(2RS,3R)-N-((2-phenylethyl)-3-amino-2-hydroxy-5-(methylthio)pentanamide hydrochloride The product of example 3A and 1-amino-2-phenylethane were processed as in example 2 to provide the title compound.

MS (APCI+) m/e 283 $(M+H)^+$;

$^1$H NMR (300 MHz, DMSO-$d_6$) δ 8.20 (m, 1H), 7.80 (m, 2H), 7.30 (m, 2H), 7.21 (m, 3H), 6.50 (m, 1H), 4.09 (m, 1H), 3.40 (m, 3H), 2.79 (m, 2H), 2.53 (m, 2H), 2.04 (s, 3H), 1.68 (m, 2H).

Example 6

(2RS,3R)-N-((3-phenylpropyl)-3-amino-2-hydroxy-5-(methylthio)pentanamide hydrochloride The product of example 3A and 1-amino-3-phenylpropane were processed as in example 2 to provide the title compound.

MS (APCI+) m/e 297 (M+H)+;

$^1$H NMR (300 MHz, DMSO-d$_6$) δ 8.20 (m, 1H), 7.82 (m, 2H), 7.28 (m, 5H), 6.54 (d, 0.6H), 6.47 (d, 0.4H), 4.09 (m, 1H), 3.40 (m, 2H), 2.68 (m, 2H), 2.57 (m, 2H), 2.05 (s, 1.8H), 1.98 (s, 1.2H), 1.68 (m, 2H).

Example 7

(2RS,3R)-N-(4-phenylbutyl)-3-amino-2-hydroxy-5-(methylthio)pentanamide hydrochloride The product of example 3A and 1-amino-4-phenylbutane were processed as in example 2 to provide the title compound.

MS (APCI+) m/e 311 (M+H)+;

$^1$H NMR (300 MHz, DMSO-d$_6$) δ 8.18 (m, 1H), 7.82 (m, 2H). 7.22 (m, 5H), 6.45 (m, 1H), 4.09 (m, 1H), 3.39 (m, 1H), 3.15 (m, 2H), 2.56 (m, 4H), 2.03 (s, 3H), 1.80 (m, 2H), 1.51 (m, 4H).

Example 8

(2RS,3R) N-(2-(4-methoxyphenyl)ethyl)-3-amino-2-hydroxy-5-(methylthio)pentanamide hydrochloride The product of example 3A and 1-amino-2-(4-methoxyphenyl)ethane were processed as in example 2 to provide the title compound.

MS (APCI+) m/e 313 (M+H)+;

$^1$H NMR (300 MHz, DMSO-d$_6$) δ 8.17 (m, 1H), 7.87 (bds, 2H), 7.12 (s, 2H), 6.86 (d, 2H), 6.5 (m, 1H), 4.1 (m, 1H), 3.72 (s, 3H), 3.30 (m, 2H), 2.70 (m, 2H), 2.54 (m, 2H), 2.05 (s, 3H), 1.78 (m, 2H).

Example 9

(2RS,3R)-N-(2-(4-sulfonamidophenyl)ethyl)-3-amino-2-hydroxy-5-(methylthio)pentanamide hydrochloride The product of example 3A and 1-amino-2-(4-sulfonamidophenyl)ethane were processed as in example 2 to provide the title compound.

MS (APCI+) m/e 362 (M+H)+;

$^1$H NMR (300 MHz, DMSO-d$_6$) δ 8.24 (m, 1H), 7.84 (m, 2H), 7.75 (d, 2H), 7.42 (d, 2H), 7.32 (s, 2H), 6.52 (d, 1H), 4.09 (m, 1H), 3.70 (m, 1H), 3.45 (m, 1H), 2.86 (m, 2H), 2.58 (m, 2H), 2.04 (s, 3H), 1.67 (m, 2H).

Example 10

(2RS,3R)-N-(2-(2-pyridyl)ethyl)-3-amino-2-hydroxy-5-(methylthio)pentanamide dihydrochloride The product of example 3A and 1-amino-2-(2-pyridyl)ethane were processed as in example 2 to provide the title compound.

MS (APCI+) m/e 284 (M+H)+;

$^1$H NMR (300 MHz, DMSO-d$_6$) δ 8.74 (m, 1H), 8.38 (m, 2H), 8.10 (m, 1H), 7.90 (m, 2H), 7.78 (m, 2H), 4.09 (m, 1H), 3.70 (m, 2H), 3.57 (m, 2H), 3.49 (m, 2H), 2.57 (m, 1H), 2.04 (s, 3H), 1.80 (m, 2H).

Example 11

(2RS,3R)-N-(2-(4-phenoxyphenyl)ethyl)-3-amino-2-hydroxy-5-(methylthio)pentanamide hydrochloride The product of example 3A and 1-amino-2-(4-phenoxyphenyl)ethane were processed as in example 2 to provide the title compound.

MS (APCI+) m/e 375 (M+H)+;

$^1$H NMR (300 MHz, DMSO-d$_6$) δ 8.17 (m, 1H), 7.69 (m, 2H), 7.39 (m, 2H), 7.23 (m, 2H), 7.13 (m, 1H), 6.98 (m, 4H), 6.50 (m, 1H), 4.09 (m, 1H), 3.38 (m, 3H), 2.75 (m, 2H), 2.56 (m, 2H), 2.04 (s, 3H), 1.74 (m, 2H).

Example 12

(2RS,3R,1'S)-N-((1-ethoxycarbonyl)ethyl)-3-amino-2-hydroxy-5-(ethylthio)pentanamide hydrochloride

Example 12A

N-(tert-butoxycarbonyl)-D-ethionine was processed as in example 1A through 1D to provide (2RS,3R) 3-(tert-butoxycarbonylamino)-2-hydroxy-5-(ethylthio)pentanoic acid.

Example 12B

The product of example 12A and L-alanine ethylester hydrochloride were processed as in example 2 to provide the title compound.

MS (ESI+Q1MS) m/e 293 (M+H)+, 585 (2M+H)+;

$^1$H NMR (300 MHz, D$_2$O) δ 4.37–4.53 (m, 2H), 4.24 (q, 2H), 3.87–3.92 (m, 0.4H), 3.73–3.79 (m, 0.6H), 2.68–2.82 (m, 2H), 2.52–2.65 (m, 2H), 1.91–2.16 (m, 2H), 1.47 (d, 3H), 1.20–1.30 (m, 6H).

Example 13

(2RS,3R)-N-(4-phenyl)butyl)-3-amino-2-hydroxy-5-(ethylthio)pentanamide hydrochloride The product of example 12A and 1-amino-4-phenylbutane were processed as in example 2 to provide the title compound.

MS (ESI+Q1MS) m/e 3.25 (M+H)+, 347 (M+Na)+, 649 (2M+H)+, 671 (2M+Na)+;

$^1$H NMR (300 MHz, DMSO-d$_6$) δ 7.16–7.31 (m, 5H), 6.77 (br., 1H), 5.22 (br.d., 0.6H), 5.01 (br.d., 0.4H), 4.23 (d. 0.4H), 4.12 (d, 0.6H), 3.94 (br.m. 1H), 3.24–3.36 (m, 2H), 2.46–2.68 (m, 6H), 1.94–2.16 (m, 2H), 1.47–1.62 (m, 4H), 1.19–1.28 (m, 3H).

Example 14

(2RS,3R)-N-(3-(carboethoxy)ethyl)-3-amino-2-hydroxy-5-(ethylthio)pentanamide hydrochloride The product of example 12A and ethyl 3-aminopropionate were processed as in example 2 to provide the title compound.

MS (ESI+Q1MS) m/e 293 (M+H)+;, 315 (M+Na)+;

$^1$H NMR (300 MHz, D$_2$O) δ 4.45 (d. 0.4H), 4.31 (d, 0.6H), 4.17 (q, 2H), 3.81–3.87 (m, 0.4H), 3.67–3.77 (m, 0.6H), 3.44–3.63 (m, 2H), 2.52–2.74 (m, 6H), 1.75–2.12 (m, 2H), 1.19–1.28 (m, 6H).

Example 15

(2RS,3R)-N-(3-(carbobenzyloxy)ethyl)-3-amino-2-hydroxy-5-(ethylthio)pentanamide hydrochloride The product of example 12A and benzyl 3-aminopropionate were processed as in example 2 to provide the title compound.

MS (ESI+Q1MS) m/e 355 (M+H)$^+$, 377 (M+Na)$^+$;

$^1$H NMR (300 MHz, DMSO-d$_6$) δ 7.45 (br.m., 5H), 5.18 (s, 2H), 4.41 (d. 0.4H), 4.21 (d, 0.6H), 3.46–3.87 (m, 3H), 2.43–2.72 (m, 6), 1.70–2.03 (m, 2H), 1.16–1.26 (m, 3H).

Example 16

(2RS,3R)-N-(3-(carboethoxy)propyl)-3-amino-2-hydroxy-5-(ethylthio)pentanamide hydrochloride The product of example 12A and ethyl 4-amino-butyrate were processed as in example 2 to provide the title compound.

MS (ESI+Q1MS) m/e 307 (M+H)$^+$, 325 (M+Na)$^+$;

$^1$H NMR (300 MHz, DMSO-d$_6$) δ 4.46 (d. 0.4H), 4.32 (d, 0.6H), 4.17 (q, 2H), 3.83–3.88 (m, 0.4H), 3.71–3.80 (m, 0.6H), 3.20–3.41 (m, 2H), 2.58–2.79 (m, 2H), 2.52–2.55 (m, 2H), 2.44 (t, 2H), 1.81–2.13 (m, 4H), 1.20–1.29 (m, 6H).

Example 17

(2RS,3R,1'S)-N-((1-ethoxycarbonyl)ethyl)-3-amino-2-hydroxy-heptanamide hydrochloride

Example 17A

N-(tert-butoxycarbonyl)-D-norleucine was processed as in examples 1A through 1D to provide (2RS,3R) 3-(tert-butoxycarbonylamino)-2-hydroxy-heptanoic acid.

Example 17B

The product of example 17A and L-alanine ethyl ester hydrochloride were processed as in example 1E to provide the title compound.donnerg MS (APCI) m/e 295 (M+H)$^+$;

$^1$H NMR (300 MHz, DMSO-d$_6$) δ 8.39 (m, 1H), 7.89 (m, 1H), 6.48 (m, 1H), 4.13 (m, 1H), 4.08 (m, 3H), 3.60 (m, 1H), 1.34 (m, 9H), 1.19 (m, 3H), 0.88 (m, 3H).

Example 18

(2RS,3R)-3-amino-2-hydroxy-5-(methylthio)pentanoic acid

N-(tert-butoxycarbonyl)-D-methionine was processed as in examples 1A through 1C to provide (2RS,3R) 3-amino-2-hydroxy-5-(methylthio)pentanoic acid.

MS (APCI) m/e 180 (M+H)$^+$;

$^1$H NMR (300 MHz, DMSO-d$_6$) δ 7.52 (bs, 2H), 3.64 (d, 1H), 3.50 (m, IH), 3.30 (m, 2H), 2.58 (m, 2H), 2.03 (s, 3H).

Example 19

(2RS,3R)-N-(2-(4-pyridyl)ethyl)-3-amino-2-hydroxy-5-(methylthio)pentanamide

The product of example 3A and 1-amino-2-(4-pyridyl)ethane were processed as in example 2 to provide the title compound.

MS (APCI) m/e 284 (M+H)$^+$;

$^1$H NMR (300 MHz, DMSO-d$_6$) δ 8.78 (m, 2H), 8.32 (m, 1H), 8.10 (m, 1H), 7.90 (m, 1H), 7.84 (m, 2H), 4.22 (m, 1H), 4.08 (m, 1H), 3.49 (m, 2H), 3.04 (m, 2H), 2.55 (m, 2H), 2.04 (s, 3H), 1.75 (m, 2H).

Example 20

(2RS,3R)-N-(2-(carboethoxy)ethyl)-3-amino-2-hydroxy-4-phenyl-butanamide hydrochloride

Example 20A

N-(tert-Butoxycarbonyl)-D-phenylalanine was processed as in examples 1A through 1D to provide (2RS,3R) 3-(tert-butoxycarbonylamino)-2-hydroxy-4-phenyl-butanoic acid.

Example 20B

The product of example 20A and ethyl 3-aminopropionate were processed as in example 2 to provide the title compound.

MS (ESI+Q1MS) m/e 295 (M+H)$^+$, 317 (M+Na)$^+$ $^1$H NMR (300 MHz, MeOH-d$_4$) δ 1.19–1.26 (m, 3H), 2.49–2.58 (m, 2H), 2.80–3.10 (m, 2H), 3.41–3.53 (m, 2H), 3.78–3.85 (m, 1H), 4.03 (d, 0.6H), 4.07–4.16 (m, 2H), 4.27 (d, 0.4H), 7.25–7.40 (m, 5H); 3.10–3.19 (m, 1H), 4.02 (d, 1H), 4.29 (m, 1H), 7.10–7.27 (m, 5H).

Example 21

(2RS,3R)-N-(3-(carboethoxy)propyl)-3-amino-2-hydroxy-4-phenyl-butanamide hydrochloride The product of example 20A and ethyl 4-amino-2-hydroxy-4-phenyl-butanamide hydrochloride The product of example 20A and ethyl 4-amino-butyrate were processed as in example 2 to provide the title compound.

MS (ESI+Q1MS) m/e 309 (M+H)$^+$, 325 (M+NH$_4$)$^+$ $^1$H NMR (300 MHz, MeOH-d$_4$) δ 1.23 (dt, 3H), 1.75–1.87 (m, 2H), 2.32–2.38 (m, 2H), 2.82–3.38 (m), 3.79–3.86 (m, 1H), 4.05–4.15 (m, 3H), 4.28 (d, 0.3H), 7.25–7.40 (m, 5H).

Example 22

(2RS,3R)-N-(4-phenylbutyl)-3-amino-2-hydroxy-4-phenyl-butanamide hydrochloride

The product of example 20A and 4-phenylbutylamine were processed as in example 2 to provide the title compound.

MS (ESI+Q1MS) m/e 327 (M+H)$^+$, 653 (2M+H)$^+$ $^1$H NMR (300 MHz, MeOH-d$_4$) δ 1.47–1.69 (m, 4H), 2.65 (t, 2H), 2.80–3.39 (m), 3.75–3.84 (m, 1H), 4.03 (d, 0.7H), 4.29 (d, 0.3H), 7.08–7.39 (m, 10H).

Example 23

(2RS,3R,1'S)-N-((1-ethoxycarbonyl)ethyl)-3-amino-2-hydroxy-4-cyclohexyl-butanamide hydrochloride

Example 23A

N-(tert-Butoxycarbonyl)-D-cyclohexylalanine was processed as in examples 1A through 1D to provide (2RS,3R) 3-(tert-butoxycarbonylamino)-2-hydroxy-4-cyclohexyl-butanoic acid.

Example 23B

The product of example 23A and L-alanine ethyl ester hydrochloride were processed as in example 1E to provide the title compound.

MS (ESI+Q1MS) m/e 301 (M+H)+, 601 (2M+H)+

¹H NMR (300 MHz, MeOH-d₄) δ 0.90–1.82 (m, 19H, includes 1.27,t, 3H; 1.45, d, 3H) 3.57–3.65 (m, 3H), 4.15–4.23 (m, 3H), 4.45 (q, 2H);

Example 24

(2RS,3R)-N-(2-(carboethoxy)ethyl)-3-amino-2-hydroxy-4-cyclohexyl-butanamide hydrochloride The product of example 23A and ethyl 3-amino-propionate were processed as in example 2 to provide the title compound.

MS (ESI+Q1MS) m/e 301 (M+H)+, 323 (M+Na)+

¹H NMR (300 MHz, MeOH-d₄) δ 0.93–1.84 (m, 16H, includes 1.26,t, 3H) 2.55–2.61 (m, 2H), 3.47–3.54 (m, 2H), 4.11–4.24 (m, 3H).

Example 25

(2RS,3R)-N-(3-(carboethoxy)propyl)-3-amino-2-hydroxy-4-cyclohexyl-butanamide hydrochloride The product of example 23A and ethyl 4-amino-butyrate were processed as in example 2 to provide the title compound.

MS (ESI+Q1MS) m/e 335 (M+Na–H)+;

¹H NMR (300 MHz, MeOH-d₄) δ 0.82–1.88 (m, 18H, includes 1.25,t, 3H), 2.34–2.39 (m, 2H), 3.18–3.38 (m, overlapped with MeOH peak), 3.57–3.67 (m, 2H), 4.08–4.25 (m, 3H).

Example 26

(2RS,3R,1'S)-N-((1-ethoxycarbonyl)ethyl)-3-amino-2-hydroxy-4-phenyl-butanamide hydrochloride The product of example 20A and L-alanine ethyl ester hydrochloride were processed as in example 1E to provide the title compound.

MS (ESI+Q1MS) m/e 295 (M+H)+;

¹H NMR (300 MHz, MeOH-d₄) δ1.25 (dt, 3H), 1.44 (d, 3H), 2.83–3.17 (m, 2H), 3.76–3.83 (m, 1H), 4.08–4.21 (m, 3H), 4.35–4.47 (m, 1H), 7.25–7.40 (m, 5H).

Example 27

(2RS,3R)-3-amino-2-hydroxy-N-(4-methoxyphenethyl)-5-(methylthio)pentanamide hydrochloride The product of example 23A and 1-amino-2-(4-methoxyphenyl)ethane were processed as in example 2 to provide the title compound.

MS (APCI) m/e 313 (M+H)+;

¹H NMR (300 MHz, DMSO-d₆) δ8.24 (m, 1H), 7.82 (m, 2H), 7.12 (d, 2H), 6.86 (d, 2H), 6.53 (d, 1H), 4.08 (m, 1H), 3.72 (s, 3H), 3.38 (m, 2H), 2.70 (m, 2H), 2.54 (m, 2H), 2.04 (s, 3H), 1.75 (m, 2H).

Example 28

(2RS,3R)-N-((2-phenylbutyl)-3-tert-butoxycarbonylamino-2-hydroxy-5-(ethylthio)pentanamide The product of example 12A and 4-phenylbutyl amine were processed as in example 1E to provide the title compound.

MS (APCI-Q1MS) m/e 459 (M+2NH₄-H)+

¹H NMR (300 MHz, MeOH-d₄) δ1.16–1.25 (dt, 3H), 1.39 (s, 0.4×9H), 1.43 (s, 0.6×9H), 1.52–1.84 (m, 6H), 2.43–2.55 (m, 3H), 3.14–3.26 (m, 1H), 3.99 (brd, 0.6H), 4.09 (brd, 0.4H), 7.10–7.27 (m, 5H);

Example 29

(2RS,3R)-N-(2-phenylbutyl)-3-acetylamino-2-hydroxy-5-(ethylthio(pentanamide

The product of example 13 and acetic anhydride were reacted in methylene chloride in the presence of triethylamine and purified on silica gel column chromatography, eluting with 1% methanol in chloroform to provide the title compound.

MS (ESI+Q1MS) m/e 367 (M+H)+, 389 (M+Na)+, 733 (2M+H)+, 755 (2M+Na)+

¹H NMR (300 MHz, MeOH-d₄) δ1.23 (t, 3H), 1.48–1.68 (m, 4H), 1.73–1.93 (m, 5H, includes, 1.87, s, 3H), 2.49–2.57 (m, 4H), 2.63 (t, 2H), 3.10–3.19 (m, 1H), 4.02 (d, 1H), 4.29 (m, 1H), 7.10–7.27 (m, 5H);

Example 30

(2RS,3R)-N-((phenylbutyryl)-3-amino-2-hydroxy-4-cyclohexyl)butanamide hydrochloride The product of example 23A and 4-phenylbutyl amine were processed as in examples 1E and 1F to provide the title compound.

MS (ESI+Q1MS) m/e 333 (M+H)+, 665 (2M+H)+

¹H NMR (300 MHz, CDCl3) δ7.14–7.30 (m, 5H), 5.04 (br. 0.7H), 4.82 (br.d, 0.3H), 4.17 (br., 0.3H), 4.04 (br.d, 0.7H), 3.86 (br.m, 1H), 3.22–3.36 (m, 2H), 2.63 (t, 2H), 0.80–1.83 (m, 19H).

Example 31

(2RS,3R)-N-((phenylbutyryl)-3-methoxycarbonylamino-2-hydroxy-4-ethylthio)pentanamide hydrochloride The product of example 13 and methyl chloroformate were reacted in tetrahydrofuran in the presence of triethylamine and purified on silica gel column chromatography, eluting with 0.5–0.75% methanol in chloroform to provide the title 15 compound.

MS (ESI+Q1MS) m/e 383 (M+H)+, 400 (M+NH4)+

¹H NMR (300 MHz, CDCl3) δ7.16–7.30 (m, 5H), 6.73 (br.d, 1H), 5.18 and 5.35 (both br. d.,total 1H), 4.25·(br.d, 0.3H), 4.14 (d, 0.7H), 3.97–4.07 (m, 1H), 3.59 and 3.67 (both s, total 3H), 3.23–3.37 (m, 2H), 2.45–2.68 (m, 6H), 1.90–2.12 (m, 2H), 1.52–1.71 (m, 6H), 1.25 (dt, 3H).

Example 32

(2RS,3R)-N-(2-(3-pyridyl)ethyl)-3-amino-2-hydroxy-5-(methylthio)pentanamide

The product of example 3A and 1-amino-2-(3-pyridyl)ethane were processed as in example 2 to provide the title compound.

MS (APCI) m/e 284 (M+H)+;

¹H NMR (300 MHz, DMSO-d₆) δ8.74 (m, 1H), 8.38 (m, 2H), 8.10 (m, 1H), 7.90 (m, 2H), 7.78 (m, 2H), 4.09 (m, 1H), 3.70 (m, 2H), 3.57 (m, 2H), 3.49 (m, 2H), 2.57 (m, 1H), 2.04 (s, 3H), 1.80 (m, 2H).

Example 33

(2RS,3R)-3-amino-2-hydroxy-N-methyl-5-(methylthio)-N-phenethylpentanaamide hydrochloride The product of example 3A and 1-(N-methylamino)-2-phenylethane were processed as in example 2 to provide the title compound.

MS (APCI) m/e 297 (M+H)$^+$;
$^1$H NMR (300 MHz, DMSO-d$_6$) δ7.88 (m, 1H), 7.76 (m, 2H), 7.37 (m, 5H), 6.38 (m, 1H), 4.42 (m, 1H), 4.23 (s., 3H), 3.70 (m, 4H), 3.49 (m, 3H), 3.05 (m, 1H), 2.92 (m, 1H), 2.04 (m, 3H).

Example 34

(2RS,3R,1'S)-N-((2-carboxyethyl)-3-amino-2-hydroxy-4-ethylthio)pentanamide hydrochloride Following example 12B an intermediate product tert-butoxycarbonyl derivative was obtained. This was saponified by 1N-lithium hydroxide in methanol-water to obtain N-protected carboxylic acid derivative, which was then treated in the same method described in example 1F provide the title compound.

MS (ESI+Q1MS) m/e 265 (M+H)$^+$, 287 (M+Na)$^+$, 529 (2M+H)$^+$, 551 (2M+Na)$^+$
$^1$H NMR (300 MHz, D2O) δ2.75–2.50 (m, 4H), 2.12–1.90 (m, 2H), 1.40 (d, 3H), 1.24 (dt, 3H);

Example 35

(2RS,3R)-N-((1-methyl-1-ethoxycarboxyethyl) 3-amino-2-hydroxy-4-ethylthio)pentanamide hydrochloride The product of example 12A and alpha aminoisobutyric acid ethyl ester hydrochloride were processed as in examples 1E and 1F to provide the title compound.

MS (ESI+Q1MS) m/e 307 (M+H)$^+$
$^1$H NMR (300 MHz, MeOH-d$_4$) δ4.26–4.14 (m, 3H), 3.77–3.53 (m, 4H), 2.77–2.55 (m, 4H), 2.14–1.84 (m, 2H), 1.54–1.51 (m, 6H), 1.29–1.22 (m, 6H);

Example 36

(2RS,3R)-N-((1-(2-hydroxy)-1-ethoxycarboxyethyl) 3-amino-2-hydroxy-4-ethylthio)pentanamide hydrochloride The product of example 12A and L-serine ethyl ester hydrochloride were processed as in examples 1E and 1F to provide the title compound.
MS (ESI+Q1MS) m/e 309 (M+H)$^+$
$^1$H NMR (300 MHz, D2O) δ4.67–4.63, (m, 1H) 4.57 (d, 0.3),4.44 (d, 0.7H), 4.24–4.15 (m, 2H), 4.06 –3.87 (3H), 3.76–3.84 (m, 1H), 2.52–2.83 (m.. 4H), 2.18–1.93 (m, 2H), 1.32–1.20 (m, 6H);

Example 37

(2RS,3R)-N-((phenylbutyryl)-3-tert-butoxycarbonylamino-2-hydroxy-4-ethylthio)pentanamide The product of example 12A and 4-phenylbutyl amine were processed as in example 1E to provide the title compound.

MS (ESI+Q1MS) m/e 439 (M+H)$^+$
$^1$H NMR (300 MHz, CDCl3) δ7.30–7.15 (m, 5H), 7.03 (t, 1H), 3.34–3.26 (m, 2H), 2.73–2.47 (m, 6H), 1.98–1.85 (m, 2H), 1.73–1.53 (m, 6H), 1.46 (s, 3H), 1.28–1.21 (m, 3H).

Example 38

(2RS,3R)-N-((phenylbutyryl)-3-formylamino-2-hydroxy-4-ethylthiol)pentanamide

The product of example 13 and formic acid-acetic anhydride in methylene chloride in the presence of triethylamine were processed as in example 1E, and purified by silica gel, eluting with 2% methanol in chloroform to provide the title compound.

MS (ESI+Q1MS) m/e 353 (M+H)$^+$, 375 (M+Na)$^+$, 727 (2M+Na)$^+$
$^1$H NMR (300 MHz, MeOH-d$_4$) δ7.26–7.11 (m, 5H), 4.44–4.38 (m, 1H), 4.05 (d, 0.7H), 4.00 (d, 0.3H), 3.27–3.12 (m, 2H), 2.63–2.49 (m, 4H), 1.93–1.30 (m, 8H), 1.26–1.20 (m, 3H).

Example 39

(2RS,3R)-N-Methyl-N-((ethoxycarbonylmethyl)-3-amino-2-hydroxy-4-ethylthio)pentanamide hydrochloride The product of example 12A and sarcosine ethyl ester hydrochloride were processed as in examples 1E and 1F to provide the title compound.

MS (ESI+Q1MS) m/e 293 (M+H)$^+$
$^1$H NMR (300 MHz, D2O) δ4.22–4.27 (m, 1H), 3.76 (s, 3H), 3.24–2.98 (m, 2H), 2.83–2.54 (m, 6H), 2.23–1.92 (m, 4H), 1.31–1.19 (m, 6H).

Example 40

(2RS,3R)-N-((Phenylbutyryl)-3-hydroxymethoylcarbonylamino-2-hydroxy-4-ethylthio)pentanamide hydrochloride The product of example 13 and glycolic acid were processed as in examples 1E and 1F to provide the title compound.

MS (ESI+Q1MS) m/e 383 (M+H)$^+$, 405 (M+Na)$^+$, 787 (2M+Na)$^+$
$^1$H NMR (300 MHz, MeOH-d$_4$) δ8.01 (br.t, 1H), 7.68 (d, 1H), 7.26–7.13 (m, 5H), 4.43–4.32 (m, 1H), 3.94–3.85 (m, 1H), 3.78–3.65 (m, 1H), 3.26–3.15 (m, 2H), 3.24–2.98 (m, 2H), 2.64–2.48 (m, 6H), 1.97–1.49 (m, 6H), 1.22 (t, 3H).

Example 41

(2RS,3R,1'R)-N-((1-ethoxycarbonylethyl)-3-amino-2-hydroxy-4-ethylthio)pentanamide hydrochloride The product of example 12A and D-alanine ethyl ester hydrochloride were processed as in examples 1E and 1F to provide the title compound.

MS (ESI+Q1MS) m/e 293 (M+H)$^+$,
$^1$H NMR (300 MHz, MeOH-d$_4$) δ4.55–4.15 (m, 4H), 3.76–3.67 (m, 2H), 2.75–2.51 (m, 4H), 2.05–2.17 (m, 1H), 1.97–1.85 (m, 1H), 1.45 (t, 3H), 1.31–1.22 (m, 6H).

Example 42

(2RS,3R,1'R)-N-((1-ethoxycarbonylethyl)-3-amino-2-hydroxy-4-cyclohexyl)butanamide hydrochloride The product of example 23A and D-alanine ethyl ester hydrochloride were processed as in examples 1E and 1F to provide the title compound.

MS (ESI+Q1MS) m/e 301 (M+H)$^+$,
$^1$H NMR (300 MHz, MeOH-d$_4$) δ4.54–4.42 (m, 1H), 4.28–4.16 (m, 2H), 3.76–3.57 (m, 2H), 1.82–0.83 (m, 19H).

Example 43

(2RS-3R)-N-((1-methyl-1-ethoxycarbonylethyl)-3-amino-2-hydroxy-4-cyclohexyl)butanamide hydrochloride The product of example 23A and alpha aminoisobutyric acid ethyl ester hydrochloride were processed as in examples 1E and 1F to provide the title compound.

MS (ESI+Q1MS) m/e 315 (M+H)+, 629 (2M+H)+,
¹H NMR (300 MHz, MeOH-d₄) δ4.23–4.09 (m, 3H), 3.76–3.57 (m, 1H), 1.82–0.82 (m, 22H).

Example 44

(2RS,3R)-N-((Phenylbutyryl)-3-methoxycarbonylmethylamino-2-hydroxy-4-ethylthio)pentanamide hydrochloride The product of example 13 and methyl bromoacetate were reacted in dimethylsulfoxide in the presence of sodium hydride and processed as in example 1E to provide the title compound.

MS (ESI+Q1MS) m/e 397 (M+H)+, 419 (M+Na)+,
¹H NMR (300 MHz, CDCl3) δ8.01 (s, 1H), 7.31–7.16 (m, 5H), 6.53 (br. 1H), 4.35–4.25 (m, 1H), 3.85–3.71 (m, 4H), 3.33–3.25 (m, 2H), 2.68–2.48 (m, 6H), 1.97–1.49 (m, 6H), 1.22 (t, 3H), 1.99–1.50 (m, 8H), 1.28–1.19 (m, 3H).

Example 45

(2RS,3R,1'S)-N-((1-ethoxycarbonylethyl)-3-amino-2-hydroxy-4-benzylthio)butanamide hydrochloride Example 45A N-(tert-Butoxycarbonyl)-S-benzyl-D-cysteine was processed as in Example 1A through 1B to prepare N-(tert-butoxycarbonyl)-S-benzyl-D-cysteinal.

Example 45B

The product of example 286491.1A (3.56 g, 12.1 mmol) was suspended in ice-cold water (70 mL) and sodium bisulfite (1.26 g, 12.1 mmol) was added, and stirred at 0° C. for 1.5 hours, and was then kept in a refrigerator for one over night. Ethyl acetate (70 mL) and potassium cyanide (0.79 g, 12.1 mmol) were added and vigorously stirred for 4 hours. The separated ethyl acetate layer was washed sequentially with water and brine, dried (MgSO₄), and concentrated to give a colorless syrup to provide 3.40 g solid material.

Example 45C

The product of example 45B (3.40 g) was dissolved in 50 mL of methanol in an ice bath and hydrogen chloride gas was bubbled through the reaction mixture until saturated. It was then stirred at 0° C. for 3 hours and at room temperature for one over night. Solvent was evaporated dryness and 20 mL of water was added to the residue. 10%-sodium hydrogen carbonate was added to the mixture to adjust pH over 9, an oil was extracted with ethyl acetate (50 mL×2). The combined ethyl acetate layer was washed with 10%-sodium hydrogen carbonate (2X), brine (3X), quickly dried over sodium sulfate anhydrous. Ethyl acetate was removed by evaporation to yield 1.77 g of dark brown oil.

This was processed as in Example 1D, and purified by silica gel column chromatography, eluting with 12.5% acetone in hexane to yield 0.12 g of (2RS, 3R)-3(tert-butoxycarbonylamino)-2-hydroxy-4-benzylthio-butanoic acid methyl ester.

Example 45D

The product of example 45C was treated with 1N-lithium hydroxide in methanol-water to provide its free carboxylic acid derivatives and coupled with L-alanine ethyl ester as in example 1E and deprotection was carried out according to the method described in example 1F to provide the title compound.

S (ESI+Q1MS) m/e 341 (M+H)+, 363 (M+Na)+, 681 (2M+H)+,
¹H NMR (300 MHz, MeOH-d₄) δ7.38–7.22 (m, 5H), 4.51–4.38 (m, 2H), 4.23–4.05 (m, 2H), 3.76–3.56 (m, 4H), 2.86–2.77 (m, 1H), 2.72–2.61 (m, 1H), 1.46–1.38 (m, 3H), 1.32–1.16 (m, 3H).

Example 46

(2RS,3R,1'S)-N-((2-hydroxy-1-ethoxycarbonylethyl)-3-amino-2-hydroxy-4-cyclohexyl)butanamide hydrochloride The product of example 23A and L-serine ethyl ester hydrochloride were processed as in examples 1E and 1F to provide the title compound.

MS (ESI+Q1MS) m/e 317 (M+H)+, 633 (2M+H)+,
¹H NMR (300 MHz, MeOH-d₄) δ4.45–4.55 (m, 1H), 4.26–4.18 (m, 3H), 4.00–3.87 (m, 2H), 3.69–3.63 (m, 1H), 0.94–1.83 (m, 16H, includes 1.29 t, 3H).

Example 47

(2RS,3R,1'S)-N-((2-acetoxypropyl)-3-amino-2-hydroxy-4-cyclohexyl)butanamide hydrochloride Example 47A N-(tert-Butoxycarbonyl)-L-alaninol (438 mg, 2.5 mmol) was dissolved in 5 mL of methylene chloride in an ice bath and acetyl chloride (0.294 mL, 3.75 mmol), followed by triethylamine (0.7 mL, 5 mmol) were added. It was then reacted at 0° C. for 1 hour and at room temperature for 2 days. The mixture was diluted with 25 mL of ethyl acetate and the organic layer was washed with 10%-sodium hydrogen carbonate (3x), brine (2x), dried over magnesium sulfate anhydrous, and then evaporated to dryness to yield 380 mg of N-(tert-butoxycarbonyl)-O-acetyl-L-alaninol.

Example 47B

The product of example 47A (380 mg) was processed as in example 1F to yield 0.26 g, of its corresponding salt. This (0.26 g, 1.69 mmol) was coupled with the product of example 23A (509 mg, 1.69 mmol) according to the method described in example 1E and purified by silica gel column eluting with 15% acetone in hexane to yield 0.35 g of N-(tert-butoxycarbonyl) derivative. The obtained product (0.35 g) was processed as in example 1F to give the title product (290 mg).

MS (ESI+Q1MS) m/e 301 (M+H)+, 601 (2M+H)+,
¹H NMR (300 MHz, MeOH-d₄) δ4.26–3.97 (m, 4H), 3.74–3.56 (m, 2H), 2.05, 2.03 (2.05, s, major, 2.03 s, minor, total 3H), 1.83–0.94 (m, 16H).

Example 48

(2RS,3R,2'S)-N-((2-propionyloxypropyl)-3-amino-b2-hydroxy-$-cyclohexyl)butanamide hydrochloride Following the procedure of example 47A, but replacing acetyl chloride with hydrochloride proplonyl chloride, provided N-(tert-butoxycarbonyl)-O-proplonyl-L-alaninol. This was followed the procedure described in example 47B to give the title compound.

MS(ESI+Q1MS) m/e 315 (M+H)+, 629(2M+H)+,
¹H NMR (300 MHz, MeOH-d₄) δ4.25–3.97 (m, 4H), 3.74–3.56 (m, 2H), 2.40–2.32 (m, 2H), 1.83–0.94 (m, 19H).

Example 49

(2RS, 3R,2'S)-N-((2-benzoyloxypropyl)-3-amino-2-hydroxy-4-cyclohexyl)butanamide hydrochloride Following the procedure of example 47A, but replacing acetyl chloride with benzoyl chloride, provided N-(tert-butoxycarbonyt)-O-benzoyl-L-alaninol. This was followed the procedure described in example 47B to give the title compound.

MS (ESI+Q1MS) m/e 363 (M+H)$^+$, 725 (2M+H)$^+$, 747 (2M+Na)$^+$, $^1$H NMR (300 MHz, MeOH-d$_4$) δ8.07–8.02 (m, 2H), 7.65–7.58 (m, 1H), 7.52–7.45 (m, 2H), 4.44–4.07 (m, 4H), 3.60–3.54 (m, 1H), 1.78–0.82 (m, 16H).

Example 50

(2RS,3R,2'R)-N-((2-benzoyloxypropyl)-3-amino-2-hydroxy-4-cyclohexyl)butanamide hydrochloride Following the procedure of example 47A, but replacing N-(tert-butoxycarbonyl)-L-alaninol with N-(tert-butoxycarbonyl)-D-alaninol and acetyl chloride with benzoyl chloride, provided N-(tert-butoxycarbonyl)-O-benzoyl-D-alaninol. This was followed the procedure described in example 47B to give the title compound.

MS (ESI+Q1MS) m/e 363 (M+H)$^+$, 725 (2M+H)$^+$, $^1$H NMR (300 MHz, MeOH-d$_4$) δ8.07–8.02 (m, 2H), 7.65–7.58 (m, 1H), 7.53–7.44 (m, 2H), 4.43–4.12 (m, 4H), 3.62–3.48 (m, 1H), 1.74–0.82 (m, 16H).

Example 51

(2RS,3R,2'R)-N-((2-propionyloxypropyl)-3-amino-2-hydroxy-4-cyclohexyl)butanamide hydrochloride Following the procedure of example 47A, but replacing N-(tert-butoxycarbonyl)L-alaninol with N-(tert-butoxycarbonyl)-D-alaninol and acetyl chloride with propionyl chloride, provided N-(tert-butoxycarbonyl)-O-propionyl-D-alaninol. This was followed the procedure described in example 47B to give the title compound.

MS (ESI+Q1MS) m/e 315 (M+H)$^+$, 629 (2M+H)$^+$, $^1$H NMR (300 MHz, MeOH-d$_4$) δ4.23–4.00 (m, 4H), 3.62–3.53 (m, 1H), 2.43–2.32 (m, 2H), 1.82–0.94 (m, 19H).

Example 52

(2RS,3R,2'R)-N-((2-acetoxypropyl)-3-amino-2-hydroxy-4-cyclohexyl)butanamide hydrochloride Following the procedure of example 47A, but replacing N-(tert-butoxycarbonyl)-L-alaninol with N-(tert-butoxycarbonyl)-D-alaninol, provided N-(tert-butoxycarbonyl)-O-acetyl-D-alaninol. This was followed the procedure described in example 47B to give the title compound.

MS (ESI+Q1MS) m/e 301 (M+H)$^+$, 601 (2M+H)$^+$, $^1$H NMR (300 MHz, MeOH-d$_4$) δ4.25–3.99 (m, 4H), 3.74–3.54 (m, 2H), 2.06,2.04 (2.04, s, major, 2.06 s, minor, total 3H), 1.83–0.82 (m, 16H).

Example 53

(2RS,3R,1'S)-N-((1-benzyloxycarbonylethyl)-3-amino-2hydroxy-$-cyclohexyl)butanamide hydrochloride The product of example 23A and L-alanine benzyl ester hydrochloride were processed as In examples 1E and 1F to provide the title compound.

MS (ESI+Q1MS) m/e 363 (M+H)$^+$, 725 (2M+H)$^+$, $^1$H NMR (300 MHz, MeOH-d$_4$) δ7.38–7.32 (m, 5H), 5.21–5.17 (m, 2H), 4.57–4.48 (m, 1H), 4.27–4.15 (m, 1H), 3.63–3.56 (m, 1H), 1.82–0.87 (m, 16H).

Example 54

(2RS,3R,1'-S)-N-(4-ethoxycarbonyl-2-(1'-aminoethyl)thizole)-3-amino-2-hydroxy-4-cyclohexyl)butanamide hydrochloride

Example 54A

N-(tert-Butoxycarbonyl)-L-alanine amide (3.76 g, 20 mmol) was suspended in 70 mL of methylene chloride in an lee bath and triethyloxonium hexafluorophosphate (4.97 g, 20 mmol) was added. It was stirred at 0° C. for 30 minutes and at room temperature for one over night. Methylene chloride layer was washed with water (2x), 10%-sodium hydrogen carbonate (2x), water (2x), dried over sodium sulfate anhydrous. It was then evaporated to dryness, dried under high vaccum to yiels 2.72 of iminoether. MS (ESI+Q1MS) m/e 217 (M+H)$^+$, 433 (2M+H)$^+$, 455 (2M+Na)$^+$

Example 54B

The product of example 54A (2.72 g, 12.6 mmol) was dissolved in 40 mL of ethanol and L-cysteine ethyl ester hydrochloride (2.57 g, 13.86 mmol) was added. It was stirred at room temperature for 2 days. Ethanol was removed by evaporation, and the residue was directly purified by silica gel column chromatography, eluting with 30% ethyl acetate in hexane to yield 2.91 g of pure thizoline analogue. MS (ESI+Q1MS) m/e 303 (M+H)$^+$, 325 (M+Na)$^+$,

Example 54C

To the product of example 54B (604 mg, 2 mmol) in a 50 mL of round bottle flask were added copper (I) bromide (316 mg, 1.1 mmol) and copper (II) acetate anhydrous (0.40 g, 2.2 mmol). The flask was evacuated with argon repeatedly and 15 mL of benzene was added via syringe. While stirring at 60° C., tert-butyl perbenzoate was carefully added in a period of 15 minutes, and gently refluxed for 4 hours. The crude product was directly purified by silica gel column chromatography, eluting eith 10% ethyl acetate in hexane to yield 390 mg of pure thiazole derivative. The obtained product (320 mg was treated according to the method as in example 1F and coupled with the product of example 23A as in example 1E to give N-(tert-butoxycarbonyl) derivative of the title compound (220 mg).

Example 54D

The product of example 54C (60 mg) was processed as in example 1F to yield the title compound.

MS (ESI+Q1MS) m/e 384 (M+H)$^+$, 767 (2M+H)$^+$, $^1$H NMR (300 MHz, MeOH-d$_4$) δ8.38, 8.34 (8.34, s, major, 8.38, s, minor both 1H), 5.51–5.27 (m, 1H), 4.43–4.23 (m, 4H), 3.71–3.57 (m, 1H), 1.70, d, 3H), 1.86–0.88 (m, 19H, includes 1.37 t, 3H).

Example 55

(2RS,3R) N-(monodansylcadaverenyl-3-amino-2-hydroxy-4-cyclohexyl)butanamide dihydrochloride The product of example 23A and monodansyl cadaverive were processed as in examples 1E and 1F to provide the title compound. MS (ESI+Q1MS) m/e 519 (M+H)$^+$;

¹NMR (300 MHz, MeOH-d₄) δ8.90 (d, 1H), 8.58 (d, 1H), 8.36 (d, 1H), 8.06 (d, 1H), 7.87 (q, 2H), 4.23 (d, 0.3H), 4.12 (d, 0.7H), 3.72–3.44 (m, 8H), 3.23–2.97 (m, 2H), 2.87 (t, 2H), 1.81–0.77 (m, 19H).

Example 56

(2RS,3R) N-(2-methyl-5-nitro imidazole-ethyl) 3-amino-2-hydroxy-4-cyclohexyl)butanamide dihydrochloride The product of example 23A and 1-(2-aminoethyl)-2-methyl-5-nitro imidazole were processed as in examples 1E and 1F to provide the title compound.

MS (ESI+Q1MS) m/e 354 (M+H)⁺, 707 (2M+H)⁺;

¹H NMR (300 MHz, MeOH-d₄) δ8.63 (mn, 1H), 8.52, 8.50 (both s, total 1H), 4.75–4.56 (m, 2H), 4.11 (d, 0.4H), 4.00 (d, 0.6H), 3.96–3.72 (m, 2H), 3.63–3.53 (m, 2H), 2.72 (s, 3H), 1.82 –0.77 (m, 13H).

Example 57

(2RS,3R) N-(5-nitropyridyl-2-aminoethyl) 3-amino-2-hydroxy-4-cyclohexyl)butanamide dihydrochloride The product of example 23A and 2-(2-aminoethylamino)-5-nitro-pyridine were processed as in examples 1E and 1F to provide the title compound.

MS (ESI+Q1MS) m/e 366 (M+H)⁺, 731 (2M+H)⁺;

¹H NMR (300 MHz, MeOH-d₄) δ8.94 (br.d, 1H), 8.41 (br. 1H), 7.90 (d, 1H), 7.77 (d, 1H), 7.61–7.49 (m, 2H), 6.98 (br., 1H), 4.28 (d, 0.4H), 4.18 (d, 0.6H), 3.96–3.72 (m, 2H), 3.77–3.42 (m, 6H), 2.72 (s, 3H), 1.80–0.77 (m, 13H).

Example 58

(2RS,3R) N-(5-methoxy-tryptaminyl) 3-amino-2-hydroxy-4-cyclohexy)butanamide dihydrochloride The product of example 23A and 5-methoxy tryptamine were processed as in examples 1E and 1F to provide the title compound.

MS (ESI+Q1MS) m/e 374 (M+H)⁺, 747 (2M+H)⁺,

¹H NMR (300 MHz, MeOH-d₄) δ7.91 (m, 1H), 7.78 (d, 1H), 7.63–7.52 (m, 2H), 7.25–7.06 (m, 1H), 4.24 (d, 0.3H), 4.13 (d, 0.7H), 3.93–3.82 (m, 4H, includes 3.84, s, 3H), 3.75–3.44 (m, 4H), 3.00–2.87 (m, 2H), 1.76–0.66 (m, 13H).

Example 59

(2RS,3R) N-(3-O-methyl-dopaminyl) 3-amino-2-hydroxy-4-cyclohexyl)butanamide hydrochride The product of example 23A and 3-O-methyl dopamine hydrochloride were processed as in examples 1E and 1F to provide the title compound.

MS (ESI+Q1MS) m/e 351 (m+H)⁺, 701 (2M+H)⁺;

¹H NMR (300 MHz, MeOH-d₄) δ7.90–7.74 (m, 1H) 7.60–7.46 (m, 1H), 6.84–6.65 (m, 3H), 4.21 (d, 0.3H), 4.10 (d, 0.7H), 3.85 (s, 3H), 3.62–3.34 (m, 4H), 2.75 (t, 2H), 1.82–0.76 (m, 13H).

Example 60

(2RS,3R) N-(2-aminomethylbenzimidazolyl) 3-amino-2-hydroxy-4-cyclohexyl)butanamide hydrochloride The product of example 23A and 2-(aminomethyl) benzimidazole dihydrochloride monohydrate were processed as in examples 1E and 1 F to provide the title compound.

MS (ESI+Q1MS) m/e 331 (M+H)⁺, 661 (2M+H)⁺;

¹H NMR (300 MHz, MeOH-d₄) δ7.92–7.47 (m, 5H), 4.46 (d, 0.3H), 4.39 (d, 0.7H), 3.77–3.56 (m, 2H), 1.84–0.83 (m, 13H).

Example 61

((2RS,3R)-3-amino-2-hydroxy-4-cyclohexyl) butanoyl-L-alanyl-(2-methyl-5-nitroimidazolyl-ethyl)amide hydrochloride

Example 61A

The product of example 23A and L-alanine benzyl ester hydrochloride were processed as in example 1E to yield N-(tert-butoxycarbonyl) drivative (3.80 g), which was hydrogenated in 50 mL of ethanol in the presence of 0.3 g of 10% palladium on charcoal as a catalyst for 3.5 hours. The mixture was passed through celite 545 and evaporated to dryness to yield (2RS,3R) N-[(3-tert-butoxycarbonylamino-2-hydroxy-4-cyclohexyl)butanoyl-L-alanine (3.16 g)

Example 61B

The product of example 61A and 1-(2-aminoethyl)-2-methyl-5-nitro imidazole were processed as in examples 1E and 1F to yield the title compound.

MS (ESI+Q1MS) m/e 425 (M+H)⁺, 849 (2M+H)⁺,

¹H NMR (300 MHz, MeOH-d₄) δ8.58, 8.56 (both s, total 1H), 4.73–4.57 (m, 2H), 4.26–4.17 (m, 2H), 3.84–3.56 (m, 4H), 2.77 (s, 3H), 1.85–0.82 (m, 16H includes 1.34 d).

Example 62

((2RS,3R)-3-amino-2-hydroxy-4-cyclohexyl) butanoyl-L-alanyl-(5-nitropyridylaminoethyl)amide dihydrochloride The product of example 61A and 2-(2-aminoethylamino)-5-nitro-pyridine were processed as in examples 1E and 1F to yield the title compound.

MS (ESI+Q1MS) m/e 437 (M+H)⁺, 873 (2M+H)⁺,

¹H NMR (300 MHz, MeOH-d₄) δ8.94–8.37 (br. m, 1H), 7.92–7.75 (m, 1H), 7.62–7.50 (m, 1H), 4.37–4.17 (m, 3H), 3.78–3.50 (m, 5H), 1.85–0.80 (m, 16H).

Example 63

((2RS,3R)-3-amino-2-hydroxy-4-cyclohexyl) butanoyl-L-alanyl-(ethylisonipecotate)amide hydrochloride The product of example 61A and ethyl isonipecotate were processed as in examples 1E and 1F to yield the title compound.

MS (ESI+Q1MS) m/e 412 (M+H)⁺, 823 (2M+H)⁺;

¹H NMR (300 MHz, MeOH-d₄) δ4.41–3.93 (m, 4H), 3.76–3.57 (m, 3H), 3.00–2.82 (m, 1H), 2.72–2.53 (m, 1H), 2.08–1.92 (m, 2H), 1.85–0.80 (m, 23H).

Example 64

((2RS,3R)-3-amino-2-hydroxy-4-cyclohexyl) butanoyl-L-alanyl-(2-pyrrolidinopropyl)amide hydrochloride The product of example 61A and 1-(3-aminopropyl)-2-pyrrolidone were processed as in examples 1E and 1F to yield the title compound.

MS (ESI+Q1MS) m/e 397 (M+H)$^+$, 793 (2M+H)$^+$, $^1$H NMR (300 MHz, MeOH-d$_4$) δ4.38–4.24 (m, 2H), 3.74–3.56 (m, 2H), 3.52–3.43 (m, 2H), 3.27–3.08 (m, 2H), 2.41 (t, 2H), 2.12–2.00 (m, 2H), 1.84–1.70 (m, 8H), 1.53–0.91 (m, 10H includes 1.42, d, 3H).

Example 65

((2RS,3R)-3-amiono-2-hydroxy-4-cyclohexyl)butanoyl-L-alanyl-(5-methoxytryptamine)amide hydrochloride The product of example 61A and 5-methoxy tryptamine were processed as in examples 1E and 1F to yield the title compound.

MS (ESI+Q1MS) m/e 455 (M+H)$^+$, 889 (2M+HP$^+$;

$^1$H NMR (300 MHz, MeOH-d$_4$) δ4.38–4.24 (m, 2H), 3.74–3.56 (m, 2H), 3.52–3.43 (m, 2H), 3.27–3.08 (m, 2H), 2.41 (t, 2H), 2.12–2.00 (m, 2H), 1.84–1.70 (m, 8H), 1.53–0.91 (m, 10H includes 1.42, d, 3H).

Example 66

((2RS,3R)-3-amino-2-hydroxy-4-cyclohexyl)butanoyl-L-alanyl-(3-O-methoxydopamine)amide hydrochloride The product of example 61A and 3-O-methoxydopamine hydrochloride were processed as in examples 1E and 1F to yield the title compound.

MS (SEI+Q1MS) m/e 422 (M+H)$^+$, 843 (2M+H)$^+$;

$^1$H NMR (300 MHz, MeOH-d$_4$) δ6.80–6.63 (m, 4H), 4.38–4.16 (m, 2H), 3.84 (s, 3H), 3.67–3.56 (m, 1H), 3.44–3.35 (m, 2H), 2.72 (t, 2H), 1.85–0.82 (m, 16H includes 1.34, d, 3H).

Example 67

((2RS,3R)-3-amino-2-hydroxy-4-cyclohexyl)butanoyl-L-alanyl-(2-benzimidazolemethyl)amide hydrochloride The product of example 61A and 2-(aminomethyl)benzimidazole dihydrochloride monohydrate were processed as in examples 1E and 1F to yield the title compound.

MS (ESI+Q1MS) m/e 402 (M+H)$^+$, 803 (2M+H)$^+$;

$^1$H NMR (300 MHz, MeOH-d$_4$) δ7.90–7.46 (m, 5H), 4.54–4.44 (m, 1H), 4.24 (d, 0.7H), 3.75–3.48 (m, 2H), 1.80–0.83 (m, 16H includes 1.50, d, 3H).

Example 68

((2RS,3R)-3-amino-2-hydroxy-4-cyclohexyl)butanoyl-L-alanyl-(5-phenyl-pyrazole-3)amide hydrochloride The product of example 61A and 3-amino-5phenyl pyrazole were processed as in examples 1E and 1F to yield the title compound.

MS (ESI+Q1MS) m/e 414 (M+H)$^+$, 827 (2M+H)$^+$;

$^1$H NMR (300 MHz, MeOH-d$_4$) δ7.92–7.46 (m, 5H), 6.80 (br., 1H), 4.64–4.56 (m, 1H), 4.33 (d, 0.3 H), 4.24 (d, 0.7H), 3.75–3.56 (m, 2H), 1.84–0.93 (m, 16H).

Example 69

((2RS,3R)-3-amino-2-hydroxy-4-cyclohexyl)butanoyl-L-alanyl-(2-hydroxy-5-nitrophen-1-yl)amide hydrochloride The product of example 61A and 2-amino-4-nitrophenol were processed as in examples 1E and 1F to yield the title compound.

MS (ESI+Q1MS) m/e 409 (M+H)$^+$, 817 (2M+H)$^+$, $^1$H NMR (300 MHz, MeOH-d$_4$) δ9.03–8.96 (m, 1H), 7.98–7.77 (m, 2H), 7.47–7.60 (m, 1H), 4.55–4.65 (m, 1H), 4.33 (d, 03H), 4.23 (d, 0.7H), 3.75–3.55 (m, 2H), 1.84–0.69 (m, 16H).

Example 70

((2RS,3R)-3-amino-2-hydroxy-4-cyclohexyl)butanoyl-L-alanyl-(5-bromothizole-2)amide hydrochloride The product of example 61A and 2-amino-5-bromothizole hydrobromide were processed as in examples 1E and 1F to yield the title compound.

MS (ESI+Q1MS) m/e 433 (M+H)$^+$, 867 (2M+H)$^+$;

$^1$NMR (300 MHz, MeOH-d$_4$) δ7.42 (s, 1H), 4.65–4.57 (m, 1H), 4.31 (d, 0.3H), 4.20 (d, 0.7H), 3.76–3.49 (m, 2H), 1.84–0.76 (m, 16H),

Example 71

((2RS,3R)-3-amino-2-hydroxy-4-cyclohexyl)butanoyl-L-alanyl-(4-nitro-2-hydroxyphen-1-yl)amide hydrochloride The product of example 61A and 2-amino-5-nitrophenol were processed as in examples 1E and 1F to yield the title compound.

MS (ESI+Q1MS) m/e 409 (M+H)$^+$, 8.17 (2M+H)$^+$ $^1$H NMR (300 MHz, D2O) δ8.08–7.98 (m, 1H), 7.85–7.68 (m, 2H), 4.68–4.57 (m, 1H), 3.76–3.49 (m, 2H), 1.88–0.80 (m, 16H).

Example 72

((2RS,3R)-3-amino-2-hydroxy-4-cyclohexyl)butanoylL-alanyl-(1-ethylpyrazole)amide hydrochloride The product of example 61A and 5-amino-1-ethylpyrazole were processed as in examples 1E and 1F to yield the title compound.

MS (ESI+Q1MS) m/e 366 (M+H)$^+$;

$^1$H NMR (300 MHz, D2O) δ7.74–7.70 (br., 1H), 7.55 (br., 1H), 4.52–3.98 (m, 4H), 3.71–3.62 (m, 1H), 1.76–0.86 (m, 19H).

Example 73

((2RS,3R)-3-amino-2hydroxy-4-cyclohexyl)butanoyl-(ethylisonipecotate)amide hydrochloride The product of example 23A and ethyl isonipecotate were processed as in examples 1E and 1F to yield the title compound.

MS (ESI+Q1MS) m/e 341 (M+H)$^+$, $^1$H NMR (300 MHz, MeOH-d$_4$) δ4.14 (q, 2H), 3.73–3.48 (m, 2H), 0.83–1.93 (m, 20H).

Example 74

((2RS,3R)-3-amino-2-hydroxy-4-cyclohexyl)butanoyl-(3-imidazolylpropyl)amide dihydrochloride The product of example 23A and 1-(3-aminoproyl)imidazole were processed as in examples 1E and 1F to yield the total compound.

MS (ESI+Q1MS) m/e 309 (M+H)$^+$, 617 (2M+H)$^+$;

$^1$H NMR (300 MHz, MeOH-d$_4$) δ9.04 (s, 1H), 7.73 (s, 1H), 7.60 (s, 1H), 4.35–4.21 (m, 3H), 3.42–3.16 (m, 2H), 2.18–2.07 (m, 2H), 0.82–1.83 (m, 15H).

Example 75

(2RS,3R)-3-amino-2-hydroxy-4-cyclohexyl) butanoyl-(4-carboxyl-2-(1'amino)ethyl thizole hydrochloride The product of example 54C (0.2 g, 0.414 mmol) was treated with 1N-lithium hydroxide (0.5 mL, 0.5 mmol) in methanol for 3hours. 8 mL of water was added to the mixture, and methanol was removed by evaporation. The aqueous layer was washed with ethyl acetate, and acidified by an addition of 10% potassium hydrogen sulfate. The product was extracted with ethyl acetate (15mL×2), and ethyl acetate layer was washed with brine (2×), dried over magnesium sulfate anhydrous. Evaporation of solvent gave 160 mg, which was then processed as in example 1F to obtain the title compound (120 mg).

MS (ESI+Q1MS) m/e 356 (M+H)$^+$, 378 (M+Na)$^+$, 711 (2M+H)$^+$, 733 (2M+Na)$^+$;

$^1$H NMR (300 MHz, D2O) δ8.20 (s, 1H), 5.40–5.29 (m, 1H), 4.34 (d, 0.3H), 4.27 (d, 0.7H), 3.69–3.53 (m, 2H), 1.72–0.73 (m, 16H).

Example 76

Ethyl (2RS,3R,2'S)-2-((-3-(acetylamino)-4-cyclohexyl-2-hydroxtybtanoyl)amino)propanoate The product of example 23 (0.050 g, 0.15 mmol), diisopropylethylamine (0.055 mL, 0.31 mmol) and acetyl chloride (0.012 mL, 0.16 mmol) in dichloromethane was stirred at 0° C. for 2 hours, washed sequentially with aqueous sodium bicarbonate, water and brine, dried (MgSO$_4$), and concentrated to give the title compound.

MS (APCI) m/e 343 (m+H)$^+$;

$^1$H NMR (300 MHz, MeOH-d$_4$), δ7.81 (m, 1H), 7.32 (m, 2H), 5.92 (d, 1H), 4.30 (1H), 4.11 (m, 4H), 3.95 (m, 1H), 3.73 (m, 2H), 3.38 (m, 1H), 1.78 (s, 3H), 1.63 (6H), 1.32 (m, 2H), 1.23 (m, 9H), 0.89 (m, 1H).

Example 77

(2RS,3R)-3-amino-2-hydroxy-4-cyclohexyl) butanoyl-(4-benzloxycarbonylamino)butylamide hydrochloride The product of example 23A and N-benzyloxycarbonyl-1,4-diaminobutane hydrochloride were processed as in examples 1E and 1F to yield the title compound.

MS (ESI+Q1MS) m/e 406 (M+H)$^+$, 428 (M+Na)$^+$, 811 (2M+H)$^+$;

$^1$H NMR (300 MHz, MeOH-d$_4$) δ7.39–7.27 (m, 5H), 5.06 (s, 2H), 4.23 (d, 0.3H), 4.14 (d, 0.7H), 3.73–3.56 (m, 2H), 3.27–3.08 (m, 4H), 1.84–0.80 (m, 17H).

Example 78

(2RS,3R)-3-amino-2-hydroxy-4-cyclohexyl) butanoyl-beta-alanine benzyl ester hydrochloride The product of example 23A and benzyl N-(2-aminoethyl)carbamate hydrochloride were processed as in examples 1E and 1F to yield the title compound.

MS (ESI+Q1MS) m/e 378 (M+H)$^+$, 400 (M+Na)$^+$ $^1$H NMR (300 MHz, MeOH-d$_4$) δ7.39–7.27 (m, 5H), 5.07 (s, 2H), 4.22 (d, 0.3H), 4.14 (d, 0.7H), 3.76–3.56 (m, 2H), 3.45–3.15 (m, 4H overlapped with MeOH peak), 1.84–0.91 (m, 13H).

Example 79

(2RS,3R)-3-amino-2-hydroxy-4-cyclohexyl) butanoyl-monodansylcadaverine amide dihydrochloride The product of example 12A and monodansyl cadaverine were processed as in examples 1E and 1F to yield the title compound.

MS (ESI+Q1MS) m/e 511 (M+H)$^+$, 533 (M+Na)$^+$;

$^1$H NMR (300 MHz, MeOH-d$_4$) δ8.87 (d, 1H), 8.55 (d, 1H), 8.35 (d, 1H), 8.02 (d, 1H), 7.88 –7.82 (m, 2H), 4.26 (d, 0.4H), 4.18 (d, 0.6H), 3.70–3.56 (m, 2H), 3.43 (s, 6H), 3.22–2.98 (m, 2H), 2.87 (t, 2H), 2.73–2.63 (m, 2H), 2.59–2.46 (m, 2H), 2.12–1.78 (m, 3H), 1.50–1.34 (m, 4H), 1.29–1.18 (m, 4H).

Example 80

(2RS,3R)-3-amino-2-hydroxy-4-cyclohexyl) butanoyl-(4-(4-toluenesulfonyl)aminobutyl)amide hydrochloride Example 80A Following example 77, the product of example 23A and N-benzyloxycarbonyl-1,4-diaminobutane hydrochloride were coupled as in examples 1E to yield the both protected compound. The product (260 mg) was hydrogenated in 10 mL of ethanol in the presence of 30 mg of 10%-palladium on charcoal for 3 hours. It was treated in the same method described in Example 61A to yield 200 mg. MS (ESI+Q1MS) m/e 372 (M+H)$^+$ Example 80B The product of example 80A (92.8 mg, 0.25 mmol) was dissolved in 5 mL of methylene chloride in an ice bath, and diisopropylethylamine (0.048 mL, 0.275 mmol) and p-toluenesulfonyl chloride (47.7 mg, 0.25 mmol) were added. It was reacted at 0° C. for 3 hours and at room temperature for over night. Methylene chloride was removed and the residue was purified by silica gel column chromatography, eluting with 15–30% acetone in hexane. The obtained product was processed as in example 1F to yield the title compound (70 mg).

MS (ESI+Q1MS) m/e 426 (M+H)$^+$, 448 (M+Na)$^+$, 533 (M+Na)$^+$;

$^1$H NMR (300 MHz, MeOH-d$_4$) δ7.73 (d, 2H), 7.37 (d, 2H), 4.22 (d, 0.4H), 4.13 (d, 0.6H), 3.74–3.56 (m, 2H), 3.25–3.07 (m, 1H), 2.84 (t, 2H), 2.43 (s, 3H), 1.84–0.81 (m, 17H).

Example 81

(2RS,3R)-3-amino-2-hydroxy-4-cyclohexyl) butanoyl-(2-4-toluenesulfonylaminoethyl)amide hydrochloride Example 81A Following example 77, the product of example 23A and benzyl N-(2-aminoethyl)carbamate hydrochloride were coupled as in example 1E to yield the protected compound. The product (220 mg) was hydrogenated in 10 mL of ethanol in the presence of 20 mg of 10%-palladium on charcoal for 3 hours. It was treated in the same method described in example 61A to yield 130 mg. MS (ESI+Q1MS) m/e 344 (M+H)+

Example 81B

The product of example 81A (42.8 mg, 0.125 mmol) and p-toluenesulfonyl chloride (23.8 mg, 0.125 mmol) were processed as in example 80B to yield the title compound (20 mg).

MS (ESI+Q1MS) m/e 426 (M+H)+, 448 (M+Na)+, 533 (M+Na)+;

$^1$H NMR (300 MHz, MeOH-d$_4$) δ7.73 (d, 2H), 7.38 (d, 2H), 4.23 (d, 0.4H), 4.15 (d, 0.6H), 3.76–3.56 (m, 2H), 3.25–3.07 (m, 1H), 3.02–2.93 (m, 2H), 2.84 (t, 2H), 2.43 (s, 3H), 1.84–0.92 (m, 13H).

Example 82

(2RS,3R)-3-amino-2-hydroxy-4-cyclohexyl) butanoyl-(4-aminobutyl)amide dihydrochloride The product of example 80A (100 mg) was processed as in example 1F to yield the title compound (70 mg).

MS (ESI+Q1MS) m/e 272 (m+H)+;

$^1$H NMR (300 MHz, MeOH-d$_4$) δ4.28 (d, 0.4H), 4.16 (d, 0.6H), 3.77–3.56 (m, 2H), 3.46–314 (m, 2H overlapped with MeOH peak), 2.96 (t, 2H), 1.84–0.80 (m, 17H).

Example 83

(2RS,3R)-3-amino-2-hydroxy-4-cyclohexyl) butanoyl-(2-aminoethyl)amide dihydrochloride The product of example 81A (60 mg) was processed as in example 1F to yield the title compound (45 mg).

MS (ESI+Q1MS) m/e 244 (m+H)+;

$^1$H NMR (300 MHz, MeOH-d$_4$) δ4.33 (d, 0.2H), 4.24 (d, 0.8H), 3.75–3.56 (m, 3H), 3.48–3.38 (m, 1H), 3.18–3.03 (m, 2H), 1.84–0.92 (m, 13H).

Example 84

(2RS,3R)-3-amino-4-cyclohexyl-2-hydroxy-N-(4-(((3-(trifluoromethyl)phenyl)sulfonyl)amino)butyl) butanamide hydrochloride The product of example 81A and m-(trifluoromethyl) benzenesulfonyl chloride were processed as in example 80B to yield the title compound.

MS (APCI) m/e 480 (M+H)+;

$^1$H NMR (300 MHz, DMSO-d$_6$) δ8.08 (m, 4H), 7.86 (m, 2H), 7.73 (m, 1H), 6.41 (d, 1H), 3.99 (m, 1H), 3.70 (m, 2H), 3.49 (m, 1H), 3.06 (m, 2H), 2.76 (m, 2H), 1.65 (m, 4H), 1.40 (m, 5H), 1.15 (m, 3H), 0.84 (m, 3H).

Example 85

(2RS,3R)-3-amino-4-cyclohexyl-N-(4-(((3,4-dimethoxyphenyl)sulfonyl)amino)butyl)-2-hydroxybutanamide hydrochloride The product of example 81A and 3,4-dimethoxybenzenesulfonyl chloride were processed as in example 80B to yield the title compound.

MS (APCI) m/e 472 (M+H)+;

$^1$H NMR (300 MHz, DMSO-d$_6$) δ8.10 (m, 1H), 7.92 (m, 1H), 7.73 (m, 1H), 7.44 (m, 1H), 7.42 (m, 1H), 7.12 (m, 1H), 6.42 (m, 1H), 3.98 (m, 1H), 3.84 (s, 3H), 3.81 (s, 3H), 3.70 (m, 2H), 3.49 (m, 1H), 3.08 (m, 2H), 2.67 (m, 2H), 1.65 (m, 4H), 1.40 (m, 5H), 1.18 (m, 3H), 0.84 (m, 3H).

Example 86

(2RS,3R)-N-(4-(((4-(acetylamiono)phenyl)sulfonyl) amino)butyl)-3-amino-4-cyclohexyl-2-hydroxybutanamide hydrochloride The product of example 81A and 4-acetamidobenzenesulfonyl chloride were processed as in example 80B to yield the title compound.

MS (APCI) m/e 469 (M+H)+;

$^1$H NMR (300 MHz, DMSO-d$_6$) δ7.72 (m, 4H), 7.41 (m, 1H), 5.93 (d, 1H), 3.79 (m, 3H), 3.04 (m, 2H), 2.73 (s, 3H), 2.68 (m, 1H), 2.09 (s, 3H), 1.60 (m, 2H), 1.24 (m, 4H), 1.13 (m, 5H), 0.85 (m, 3H).

Example 87

(2RS,3R)-3-amino-4-cyclohexyl-2-hydroxy-N-(4-((2-naphthylsulfonyl)amino)butyl)butanamide hydrochloride The product of example 81A and 2-naphthylsulfonyl chloride were processed as in example 80B to yield the title compound.

MS (APCI) m/e 462 (M+H)+;

$^1$H NMR (300 MHz, DMSO-d$_6$) δ8.61 (s, 1H), 8.15 (m, 2H), 8.04 (m, 2H), 7.82 (m, 1H), 7.70 (m, 4H), 6.41 (m, 1H), 3.99 (m, 1H), 3.69 (m, 2H), 3.50 (m, 1H), 3.04 (m, 2H), 2.77 (m, 2H), 1.64 (m, 4H), 1.42 (5H), 1.14 (m, 3H), 0.85 (m, 3H).

Example 88

(2RS,3R)-3-amino-2-hydroxy-4-cyclohexyl) butanoyl-L-alanine-4-sulfonamide benzyl ester hydrochloride The product of example 23A and 4-(2-aminoethyl) benzenesulfonamide were processed as in examples 1E and 1F to yield the title compound.

MS (ESI+Q1MS) m/e 384 (M+H)+;

$^1$H NMR (300 MHz, MeOH-d$_4$) δ4.20 (d,), 4.10 (d,), 3.75–3.56 (m, 3H), 3.85–3.37 (m, 2H), 2.93 (t, 2H), 1.8–0.91 (m, 15H).

Example 89

(2RS,3R)-3-Amino-2-hydroxy-4-cyclohexyl) butanoyl-L-alanine Benzyl Ester Hydrochloride The product of example 23A and amino isobutyric acid benzyl ester were processed as in examples 1E and 1F to yield the title compound.

MS (ESI+Q1MS) m/e 377 (M+H)+, 753 (2M+H)+;

$^1$H NMR (300 MHz, MeOH-d$_4$) δ 7.39–7.30 (m, 5H), 5.17 (s, 2H), 4.22 (d, 0.3H), 4.08 (d, 0.7H), 3.76–3.46 (m, 2H), 1.81–0.74 (m, 19H).

Example 90

(2RS,3R)-3-Amino-2-hydroxy-4-cyclohexyl) butanoyl-L-alanine Cyclohexyl Ester Hydrochloride

Example 90A

N-(tert-Butoxycarbonyl)-L-alanine (0.945 g, 5 mmol) was dissolved in 10 mL of methanol and 2 mL of water was added, and pH was then adjusted to 7.0 by an addition of 20% cesium carbonate. The mixture was eveporated to dryness, re-evaporated twice from 5 mL of N,N-dimethylformamide, and suspended into 10 mL of N,N-dimethylformamide.

Cyclohexyl bromide (0.677 mL, 5.5 mmol) was added and stirred at room temperature for over night. The mixture was diluted with 40 mL of ethyl acetate, the organic layer was washed with brine (2×), 10% sodium hydrogen carbonate (2×), brine (2×), dried over magnesium sulfate anhydrous. It was then evapotated to dryness to yield 0.97 g of N-(tert-butoxycarbonyl)-L-alanine cyclohexyl ester. All was processed as in example 1F to obtained L-alanine cyclohexyl ester hydrochloride (0.68 g).

Example 90B

The product of example 23A and the product of example 90A were processed as in examples 1E and 1F to yield the title compound.

MS (ESI+Q1MS) m/e 355 (M+H)$^+$, 709 (2M+H)$^+$;

$^1$H NMR (300 MHz, MeOH-d$_4$) δ 4.46–4.35 (m, 1H), 4.28 (d, 0.3H), 4.17 (d, 0.7H), 3.78–3.56 (m, 2H), 0.74–1.81 (m, 27H includes 1.45 d, 3H).

Example 91

(2RS,3R)-3-Amino-2-hydroxy-4-cyclohexyl) butanoyl-L-alanine-2-((phenylsulfonyl)methyl) benzyl Ester Hydrochloride Following the procedure of example 90A, but replacing cyclohexyl bromine with 1-bromomethyl-2-[(phenylsulfonyl)methyl]benzene, followed by the procedure of example 1F provided the desired title compound.

MS (ESI+Q1MS) m/e 517 (M+H)$^+$, 539 (M+Na)$^{30}$, 1033 (2M+H)$^+$;

$^1$H NMR (300 MHz, MeOH-d$_4$) δ 7.75–7.68 (m, 3H), 7.62–7.53 (m, 2H), 7.46–7.32 (m, 2H), 7.27–7.18 (m, 1H), 7.06–6.98 (m, 1H), 5.22–5.18 (m, 2H), 4.69–4.66 (m, 2H), 4.54–4.44 (m, 1H), 4.27 (d, 0.3H), 4.16 (d, 0.7H), 3.76–3.54 (m, 2H), 1.83–0.74 (m, 16H).

Example 92

(2RS,3R)-3-Amino-2-hydroxy-4-cyclohexyl) butanoyl-L-alanine Cyclopropyl Ester Hydrochloride Following the procedure of example 90A, but replacing cyclohexyl bromide with cyclopropyl bromide, and followed by the procedure of example 1F provided the desired title compound.

MS (ESI+Q1MS) m/e 315 (M+H)$^+$, 629 (2M+H)$^+$;

$^1$H NMR (300 MHz, MeOH-d$_4$) δ 5.06–4.97 (m, 1H), 4.45–4.36 (m, 1H), 4.17 (d, 0.7H), 3.63–3.57 (m, 1H), 1.84–0.90 (m, 20H).

Example 93

(2RS,3R)-3-Amino-2-hydroxy-4-cyclohexyl) butanoyl-L-alanine 4-tert-butylbenzyl Ester Hydrochloride Following the procedure of example 90A, but replacing cyclohexyl bromide with 4-tert-butylbenzyl bromide, followed by the procedure of example 1F provided the desired title compound.

MS (ESI+Q1MS) m/e 419 (M+H)$^+$, 837 (2M+H)$^+$;

$^1$H NMR (300 MHz, MeOH-d$_4$) δ 7.42–7.28 (m, 4H), 5.15 (s, 2H), 4.56–4.47 (m, 1H), 4.28 (d, 0.3H), 4.16 (d, 0.7H), 3.74–3.55 (m, 2H), 1.84–0.90 (m, 25H includes 1.32 s, 9H and 1.45 d, 3H).

Example 94

(2RS,3R)-3-Amino-2-hydroxy-4-cyclohexyl) butanoyl-L-alanine 4-methoxycarbonylbenzyl Ester Hydrochloride Following the procedure of example 90A, but replacing cyclohexyl bromide with 4-methoxycarbonylbenzyl bromide, followed by the procedure of example 1F provided the desired title compound.

MS (ESI+Q1MS) m/e 421 (M+H)$^+$, 841 (2M+H)$^+$;

$^1$H NMR (300 MHz, MeOH-d$_4$) δ 8.04–7.46 (m, 4H), 5.26 (s, 2H), 4.62–4.51 (m, 1H), 4.29 (d, 0.3H), 4.16 (d, 0.7H), 3.90 (s, 3H), 3.75–3.55 (m, 2H), 0.66–1.79 (m, 16H).

Example 95

(2RS,3R)-3-Amino-2-hydroxy-4-cyclohexyl) butanoyl-L-alanine 4-trifluoromethylbenzyl Ester Hydrochloride Following the procedure of example 90A, but replacing cyclohexyl bromide with 4-trifluoromethylbenzyl bromide, followed by the procedure of example 1F provided the desired title compound.

MS (ESI+Q1MS) m/e 431 (M+H)$^+$, 861 (2M+H)$^+$;

$^1$H NMR (300 MHz, MeOH-d$_4$) δ 7.70–7.56 (m, 4H), 5.27 (s, 2H), 4.62–4.52 (m, 1H), 4.31 (d, 0.3H), 4.16 (d, 0.7H), 3.76–3.56 (m, 2H), 1.81–0.66 (m, 16H).

Example 96

(2RS,3R)-3-Amino-2-hydroxy-4-cyclohexyl) butanoyl-L-alanine-(4-(methyl)phenyl Acetic Acid Phenacyl Ester) Hydrochloride Following the procedure of example 294115.1A, but replacing cyclohexyl bromide with 4-(bromomethyl)phenyl acetic acid phenacyl ester, followed by the procedure of example 1F provided the desired title compound.

MS (ESI+Q1MS) m/e 539 (M+H)$^+$;

$^1$H NMR (300 MHz, MeOH-d$_4$) δ 7.96–7.32 (m, 9H), 5.46–5.17 (m, 4H), 4.59–4.48 (m, 1H), 4.28 (d, 0.3H), 4.16 (d, 0.7H), 3.84 (s, 2H), 3.76–3.54 (m, 2H), 1.80–0.75 (m, 16H).

Example 97

(2RS,3R)-3-Amino-4-cyclohexyl)-N-(2,4-dichlorobenzyl)-2-hydroxybutanamide Hydrochloride The product of example 23A and 2,4-dichlorobenzylamine were processed as in example 101 to provide the title compound.

MS (ESI+Q1MS) m/e 359 (M+H)$^+$ $^1$H NMR (300 MHz, MeOH-d$_4$) δ 7.47 (d, 1H), 7.39 (d, 1H), 7.30 (dd, 1H), 4.54 (q, 2H), 4.13 (d, 1H), 3.49 (m, 1H), 3.0 (br s, 1H), 0.82–1.80 (m, 13H).

Example 98

(2RS,3R)-3-Amino-4-cyclohexyl-2-hydroxy-N-(3-methoxyphenyl)butanamide Hydrochloride The product of example 23A and 3-methoxyaniline were processed as in example 101 to provide the title compound.

MS (ESI+Q1MS) m/e 307 (M+H)$^+$, 329 (M+Na)$^+$ $^1$H NMR (300 MHz, MeOH-d$_4$) δ 7.37 (t, 1H), 7.23 (dd, 1H), 7.16 (m, 1H), 6.72 (m, 1H), 4.24 (d, 1H), 3.79 (s, 3H), 3.66 (m, 1H), 0.80–1.85 (m, 13H).

Example 99

Methyl (2RS,3R,2'R)-2-(3-Amino-4-cyclohexyl-2-hydroxybutanoyl)amino)-4-methylpentanoate Hydrochloride The product of example 23A and L-leucine methyl ester were processed as in example 101 to provide the title compound.

MS (ESI+Q1MS) m/e 329 (M+H)$^+$, 351 (M+Na)$^+$ $^1$H NMR (300 MHz, MeOH-d$_4$) δ 4.05 (m, 1H), 4.10 (d, 1H), 3.73 (s, 3H), 3.39 (m, 1H), 1.2–1.81 (m, 13H), 0.9–1.0 (m, 9H).

Example 100

(2RS,3R)-3-Amino-4-cyclohexyl-N-(2-furylmethyl)-2-hydroxybutanamide Hydrochloride The product of example 23A and furfurylamine were processed as in example 101 to provide the title compound.

MS (ESI+Q1MS) m/e 281 (M+H)$^+$, 303 (M+Na)$^+$ $^1$H NMR (300 MHz, MeOH-d$_4$) δ 7.42 (m, 1H), 6.35 (m, 1H), 6.28 (d, 1H), 4.47 (q, 2H), 4.13 (d, 1H), 3.51 (m, 1H), 0.90–1.80 (m, 13H).

Example 101

(2RS,3R,1'RS)-3-Amino-4-cyclohexyl-2-hydroxy-N-(1-(1-naphthyl)ethyl)butanamide Hydrochloride The product of example 23A (2.4 g, 8.64 mmol) was dissolved in N,N-dimethylacetamide to give 48 ml (solution A). 1-Hydroxy-7-azabenzotriazole (HOAT-1.92 g, 13.2 mmol), O-(7-azabenzotriazol-1-yl)-1,1,3,3-tetramethyluronium hexafluorophosphate (HATU-4.8 g, 13.4 mmol), and diisopropylethylamine (2.4 ml, 13.4 mmol) were dissolved in N,N-dimethylacetamine to make 48 ml (solution B). Solution A was distributed equally into 48 individual reactors. Solution B was then added to these same reactors in equal portions. The reactors were shaken 10 min at room temperature. To one of these reactors, 1-(1-naphthyl)ethylamine(0.04 ml, 0.275 mmol) was added and the mixture was shaken ca. 75 h. Dichloromethane (5 ml) and water (5 ml) were added to the reaction and shaken. The aqueous layer was removed and the reactor place on a liquid phase extractor to wash twice with 1N hydrochloric acid, once with water, and finally, twice with 2N sodium carbonate. Any residual water was removed and the solvent was concentrated to dryness. The residue was dissolved in dichloromethane (1 ml) and placed on a solid phase extractor to be eluted on a 1 g silica gel cartridge with 13% ethyl acetate in hexane. The appropriate fractions were collected and dried down. The residue was dissolved in 4M hydrochloric acid in dioxane (1 ml) to cleave the protecting group. After one hour, the solvent was concentrated to dryness. 48 amines were processed at one time in batch mode. Based on HPLC purity, the material was either submitted as is, or sent for preparative HPLC purification prior to submission.

MS (ESI+Q1MS) m/e 355 (M+H)$^+$, 377 (M+Na)$^+$ $^1$H NMR (300 MHz, MeOH-d$_4$) δ 8.16 (m, 1H), 7.89 (d, 1H), 7.81 (d, 1H), 7.44–7.63 (m, 4H), 5.90 (q, 1H), 4.08 (dd, 1H), 3.48 (m, 1H), 2.98 (br s, 1H), 0.85–1.91 (m, 17H).

Example 102

(2RS,3R)-3-Amino-4-cyclohexyl-2-hydroxy-N-(3-(2-oxo-1-pyrrolidinyl)propyl)butanamide Hydrochloride The product of example 23A and 1-(3-aminopropyl)-2-pyrrolidone were processed as in examples 1E and 1F to provide the title compound.

MS (ESI+Q1MS) m/e 326 (M+H)$^+$, 651 (2M+H)$^+$;

$^1$H NMR (300 MHz, MeOH-d$_4$) δ 4.24 (d, 0.4H), 4.15 (d, 0.6H), 3.54–3.41 (m, 2H), 3.27–3.15 (m, 2H), 2.44–2.34 (m, 2H), 2.12–2.02 (m, 2H), 1.86–0.72 (m, 19H).

Example 103

(2RS,3R)-3-Amino-4-cyclohexyl-N-(1,2-dimethylpropyl)-2-hydroxybutanamide Hydrochloride The product of example 23A and 1,2-dimethylpropylamine were processed as in example 101 to provide the title compound.

MS (ESI+Q1MS) m/e 271 (M+H)$^+$, 293 (M+Na)$^+$ $^1$H NMR (300 MHz, MeOH-d$_4$) δ 4.28 (d, 1H), 3.74 (m, 1H), 1.05–1.80 (m, 13H), 0.88–0.94 (m, 11H).

Example 104

(2RS,3R)-3-Amino-2-hydroxy-4-cyclohexyl)butanoyl-L-alanine Hydrochloride

The product of example 61A was processed as in example 1F to yield the title compound.

MS (ESI+Q1MS) m/e 271 (M−H)$^+$, 307 (M+Na−H)$^+$, 543 (2M−H)$^+$, 565 (2M+Na−H)$^+$;

$^1$H NMR (300 MHz, D2O) δ 4.28–4.47 (m, 2H), 3.86–3.62 (m, 2H), 1.75–0.78 (m, 16H).

Example 105

(2RS,3R)-3-Amino-2-hydroxy-4-cyclohexyl)butanoyl-L-alanine Benzyl Ester Hydrochloride The product of example 20A and L-alanine benzyl ester were processed as in examples 1E and 1F to yield the title compound.

MS (ESI+Q1MS) m/e 357 (M+H)$^+$, 713 (2M+H)$^+$;

$^1$H NMR (300 MHz, D2O) δ 7.39–7.17 (m, 10H), 5.16 (s, 2H), 4.53–4.43 (m, 1H), 4.35 (d, 0.3H), 4.07 (d, 0.7H), 3.82–3.63 (m, 2H, 3.12–2.76 (m, 2H, 1.45 (d, 3H).

Example 106

(2RS,3R)-3-Amino-2-hydroxy-4-cyclohexyl)butanoyl-L-alanine Hydrochloride

Example 106A

The product of example 20A and L-alanine benzyl ester were processed as in examples 1E to yield (2RS,3R)-3-(tert-butoxycarbonylamino)-2-hydroxy-4-cyclohexyl)butanoyl-L-alanine benzyl ester. 0.5 g of the above product was hydrogenated in 2 mL of isopropyl alcohol in the presence of 20 mg of 10%-palladium on charcoal to yield (2RS,3R)-3-(tert-butoxycarbonylamino)-2-hydroxy-4-cyclohexyl)butanoyl-L-alanine (0.4 g).

Example 106B

The product of example 106.1A was processed as in example 1F to yield the title compound.

MS (ESI+Q1MS) m/e 267 (M+H)⁺, 289 (M+Na)⁺, 533 (2M+H)⁺, 555 (2M+Na)⁺;

¹H NMR (300 MHz, D2O) δ 7.46–7.27 (m, 5H), 4.52–4.13 (m, 2H), 4.03–3.85 (m, 2H), 3.19–2.88 (m, 2H), 1.45–1.38 (dt, 3H).

Example 107

(2RS,3R)-3-Amino-4-cyclohexyl-2-hydroxy-N-phenylbutanamide Hydrochloride

The product of example 23A and aniline were processed as in example 101 to provide the title compound.

MS (APCI) m/e 277 (M+H)⁺

¹H NMR (300 MHz, MeOH-d₄) δ 7.64 (m, 2H), 7.35 (m, 2H), 7.14 (m, 1H), 4.22 (d, 1H), 3.61 (m, 1H), 0.91–1.85 (m, 13H).

Example 108

(2RS,3R)-3-Amino-N-(2-chlorophenethyl)-4-cyclohexyl-2-hydroxybutanamide Hydrochloride The product of example 23A and 2-(2-chlorophenyl)ethylamine were processed as in example 101 to provide the title compound.

MS (APCI) m/e 339 (M+H)⁺

¹H NMR (300 MHz, MeOH-d₄) δ 7.2–7.4 (m, 4H), 4.04 (d, 1H), 3.00 (m, 1H), 0.9–1.81 (m, 13H).

Example 109

(2RS,3R)-3-Amino-4-cyclohexyl-2-hydroxy-N-(3-phenylpropyl)butanamide Hydrochloride The product of example 23A and 3-phenyl-1-propylamine were processed as in example 101 to provide the title compound.

MS (APCI) m/e 319 (M+H)⁺

¹H NMR (300 MHz, MeOH-d₄) δ 7.12–7.3 (m, 5H), 4.1 (d, 1H), 3.25 (m, 1H), 2.65 (m, 6H), 0.90–1.90 (m, 13H).

Example 110

(2RS,3R)-3-Amino-4-cyclohexyl-2-hydroxy-N-(1,2,3,4-tetrahydro-1-naphthalenyl)butanamide Hydrochloride The product of example 23A and 1,2,3,4-tetrahydro-1-naphthylamine were processed as in example 101 to provide the title compound.

MS (APCI) m/e 3661 (2M+H)⁺

¹H NMR (300 MHz, MeOH-d₄) δ 7.15 (m, 4H), 5.12 (m, 1H), 4.14 (m, 1H), 3.58 (m, 1H), 2.81 (m, 2H), 2.05 (m, 1H), 0.90–1.90 (m, 16H).

Example 111

(2RS,3R)-3-Amino-N-(4-(tert-butyl)cyclohexyl)-4-cyclohexyl-2-hydroxybutanamide Hydrochloride The product of example 23A and 1-amino-4-(1,1-dimethylethyl)cyclohexane were processed as in example 101 to provide the title compound.

MS (APCI) m/e 339 (M+H)⁺, 677.3 (2M+H)⁺

¹H NMR (300 MHz, MeOH-d₄) δ 4.03 (d, 1H), 3.62 (m, 1H), 3.49 (m, 1H), 0.90–2.00 (m, 22H), 0.89 (m, 9H).

Example 112

(2RS,3R)-3-Amino-4-cyclohexyl-N-(3,5-dichlorophenyl)-2-hydroxybutanamide Hydrochloride The product of example 23A and 3,4-dichloroaniline were processed as in example 101 to provide the title compound.

MS (APCI) m/e 345 (M+H)⁺

¹H NMR (300 MHz, MeOH-d₄) δ 7.74 (d, 2H), 7.20 (t, 1H), 4.23 (d, 1H), 3.58 (m, 1H), 0.92–1.85 (m, 13H).

Example 113

(2RS,3R)-3-Amino-4-cyclohexyl-N-(2-ethylhexyl)-2-hydroxybutanamide Hydrochloride The product of example 23A and 2-ethylhexylamine were processed as in example 101 to provide the title compound.

MS (APCI) m/e 313 (M+H)⁺

¹H NMR (300 MHz, MeOH-d₄) δ 4.03 (dd, 1H), 3.13 (m, 1H), 0.89–1.85 (m, 29H).

Example 114

Butyl (2RS,3R)-2-((3-Amino-4-cyclohexyl-2-hydroxybutanoyl)amino)acetate Hydrochloride The product of example 23A and glycine n-butyl ester were processed as in example 101 to provide the title compound.

MS (APCI) m/e 315 (M+H)⁺

¹H NMR (300 MHz, MeOH-d₄) δ 4.16 (m, 2H), 4.02 (m, 1H), 3.50 (m, 1H), 0.90–1.85 (m, 19H), 0.95 (t, 3H).

Example 115

(2RS,3R)-3-Amino-N-(1,3-benzodioxol-5-ylmethyl)-4-cyclohexyl-2-hydroxybutanamide Hydrochloride The product of example 23A and piperonylamine were processed as in example 101 to provide the title compound.

MS (APCI) m/e 335 (M+H)⁺, (669 (2M+H)⁺

¹H NMR (300 MHz, MeOH-d₄) δ 6.80 (m, 2H), 5.92 (s, 1H), 4.32 (q, 2H), 4.11 (d, 1H), 3.50 (m, 1H), 0.85–1.80 (m, 13H).

Example 116

(2RS,3R)-3-Amino-4-cyclohexyl-N-(2,4-dimethoxyphenyl)-2-hydroxybutanamide Hydrochloride The product of example 23A and 2,4-dimethoxyaniline were processed as in example 101 to provide the title compound.

MS (APCI) m/e 673 (2M+H)⁺

¹H NMR (300 MHz, MeOH-d₄) δ 8.09 (d, 1H), 6.63 (d, 1H), 6.51 (dd, 1H), 4.27 (d, 1H), 3.89 (s, 3H), 3.79 (s, 3H), 3.67 (m, 1H), 0.95–1.87 (m, 13H).

Example 117

(2RS,3R)-3-Amino-4-cyclohexyl-2-hydroxy-N-(3-methoxy-5-(trifluoromethyl)phenyl)butanamide Hydrochloride The product of example 23A and 3-methoxy-5-(trifluoromethyl)aniline were processed as in example 101 to provide the title compound.

MS (APCI) m/e 375 (M+H)⁺, 748 (2M+H)⁺

¹H NMR (300 MHz, MeOH-d₄) δ 7.55 (m, 1H), 7.47 (t, 1H), 6.85 (m, 1H), 4.10 (d, 1H), 3.45 (m, 1H), 0.80–1.75 (m, 13H).

Example 118

(2RS,3R)-3-Amino-4-cyclohexyl-N-decyl-2-hydroxybutanamide Hydrochloride

The product of example 23A and undecylamine were processed as in example 101 to provide the title compound.

MS (APCI) m/e 681 (2M+H)+

$^1$H NMR (300 MHz, MeOH-d$_4$) δ 3.85 (d, 1H), 3.22 (m, 2H), 3.13 (m, 1H), 0.85–1.85 (m, 32H).

Example 119

(2RS,3R)-3-Amino-N-((1R,4S)bicyclo(2.2.1)hept-2-yl)-4-cyclohexyl-2-hydroxybutanamide The product of example 23A and 2-aminonorbornane were processed as in example 101 to provide the title compound.

MS (APCI) m/e 295 (M+H)+, 589 (2M+H)+

$^1$H NMR (300 MHz, MeOH-d$_4$) δ 4.05 (t, 1H), 3.66 (m, 1H), 3.51 (m, 1H), 2.30 (br s, 1H), 2.22 (m, 1H), 0.90–1.80 (m, 21H).

Example 120

(2RS,3R)-3-Amino-4-cyclohexyl-N-(2-fluorobenzyl)-2-hydroxybutanamide Hydrochloride The product of example 23A and 2-fluorobenzylamine were processed as in example 101 to provide the title compound.

MS (APCI) m/e 309 (M+H)+, 616 (2M+H)+

$^1$H NMR (300 MHz, MeOH-d$_4$) δ 7.32 (m, 2H), 7.11 (m, 2H), 4.5 (q, 2H), 4.14 (d, 1H), 3.52 (m, 1H), 0.87–1.80 (m, 13H).

Example 121

(2RS,3R)-3-Amino-4-cyclohexyl-N-(4-fluoro-3-(trifluoromethyl)benzyl)-2-hydroxybutanamide Hydrochloride The product of example 23A and 3-(trifluoromethyl)-4-fluorobenzylamine were processed as in example 101 to provide the title compound.

MS (APCI) m/e 377 (M+H)+

$^1$H NMR (300 MHz, MeOH-d$_4$) δ 7.64 (m, 2H), 7.29 (t, 1H), 4.45 (q, 2H), 4.12 (d, 1H), 3.49 (m, 1H), 0.80–1.80 (me, 13H).

Example 122

(2RS,3R)-3-Amino-4-cyclohexyl-N-(1-(4-fluorophenyl)ethyl)-2-hydroxybutanamide Hydrochloride The product of example 23A and 4-fluoro-a-methylbenzylamine were processed as in example 101 to provide the title compound.

MS (APCI) m/e 645 (2M+H)+

$^1$H NMR (300 MHz, MeOH-d$_4$) δ 7.36 (m, 2H), 7.04 (t, 2H), 5.06 (m, 1H), 4.05 (d, 1H), 3.47 (m, 1H), 0.80–1.85 (m, 17H).

Example 123

(2RS,3R)-3-Amino-4-cyclohexyl-2-hydroxy-N-(tetrahydro-2-furanylmethyl)butanamide Hydrochloride The product of example 23A and tetrahydrofurfurylamine were processed as in example 101 to provide the title compound.

MS (APCI) m/e 285 (M+H)+

$^1$H NMR (300 MHz, MeOH-d$_4$) δ 4.07 (m, 1H), 3.88 (m, 1H), 3.75 (m, 1H), 3.48 (m, 1H), 1.92 (m, 1H), 0.90–185 (m, 19H).

Example 124

Ethyl (2RS,3R)-(4-((-3-Amino-4-cyclohexyl-2-hydroxybutanoyl)amino)-1-piperidinecarboxylate Hydrochloride The product of example 23A and 4-amino-1-piperidinecarboxylate were processed as in example 101 to provide the title compound.

MS (APCI) m/e 356 (M+H)+

$^1$H NMR (300 MHz, MeOH-d$_4$) δ 4.1 (q, 2H), 4.05 (t, 1H), 3.91 (m, 1H), 3.48 (m, 1H), 2.94 (m, 2H), 1.26–1.90 (m, 17H), 1.25 (t, 3H), 0.95 (m, 2H).

Example 125

(2RS,3R)-3-amino-N-(1,3-benzodioxol-5-yl)-4-cyclohexyl-2-hydroxybutanamide hydrochloride The product of example 23A and 3,4-methylenedioxyaniline were processed as in example 101 to provide the title compound.

MS (APCI) m/e 321 (M+H)+, 640 (2M+H)+

$^1$H NMR (300 MHz, MeOH-d$_4$) δ7.32 (d, 1H), 7.00 (dd, 1H), 6.77 (dd, 1H), 5.94 (s, 2H), 4.25 (d, 1H), 3.68 (m, 1H), 0.90–1.85 (m, 13H).

Example 126 tert-butyl (2RS,3R)-2-((3-amino-4-cyclohexyl-2-hydroxybutanoyl)amino)acetate hydrochloride The product of example 23A and glycine tert-butyl ester were processed as in example 101 to provide the title compound.

MS (APCI) m/e 315 (M+H)+

$^1$H NMR (300 MHz, MeOH-d$_4$) δ4.10 (d, 1H), 3.91 (q, 2H), 3.45 (m, 1H), 1.48 (s, 9H), 0.90–1.85 (m, 13H).

Example 127 methyl (2RS,3R)-2-((3-amino-4-cyclohexyl-2-hydroxybutanoyl)amino)-3-phenylpropanoate hydrochloride The product of example 23A and phenylalanine methyl ester were processed as in example 101 to provide the title compound.

MS (APCI) m/e 363 (M+H)+

$^1$H NMR (300 MHz, MeOH-d$_4$) δ7.23 (m, 5H), 4.74 (m, 1H), 4.17 (d, 1H), 3.73 (s, 3H), 3.47 (m, 1H), 3.01–3.25 (m, 2H), 0.70–1.78 (m, 13H).

Example 128 methyl (2RS,3R,2'S)-2-((3-amino-4-cyclohexyl-2-hydroxybutanoyl)amino)-3-methylpentanoate hydrochloride The product of example 23A and L-isoleucine methyl ester were processed as in example 101 to provide the title compound.

MS (APCI) m/e 657 (2M+H)+

$^1$H NMR (300 MHz, MeOH-d$_4$) δ4.41 (m, 2H), 4.33 (d, 1H), 4.17 (m, 1H), 3.95 (s, 3H), 3.73 (d, 2H), 0.90–1.78 (m, 22H).

Example 129 methyl (2RS,3R,2'S)-2-((3-amino-4-cyclohexyl-2-hydroxybutanoyl)amino)hexanoate hydrochloride The product of example 23A and L-norleucine methyl ester were processed as in example 101 to provide the title compound.

MS (APCI) m/e 657 (2M+H)$^+$ $^1$H NMR (300 MHz, MeOH-d$_4$) δ4.44 (m, 1H), 4.13 (d, 1H), 3.74 (s, 3H), 3.45 (m, 1H), 0.90–1.82 (m, 22H).

Example 130 methyl (2RS,3R)-2-((3-amino-4-cyclohexyl-2-hydroxybutanoyl)amino)-3-methylbutanoate hydrochloride The product of example 23A and L-valine methyl ester were processed as in example 101 to provide the title compound.

MS (APCI) m/e 315 (M+H)$^+$ $^1$H NMR (300 MHz, MeOH-d$_4$) δ4.36 (d, 2H), 4.05 (d, 1H), 3.72 (s, 3H), 2.20 (m, 2H), 0.98 (s, 3H), 0.96 (s, 3H), 0.87–1.84 (m, 13H).

Example 131

(2RS,3R)-3-amino-4-cyclohexyl-2-hydroxy-N-((1S)-1-(2-naphthyl)ethyl)butanamide

The product of example 23A and (S)-1-amino-1-(2-naphthyl)ethane were processed as in example 24 to provide the title compound.

MS (ESI) m/e 355 (M+H)$^+$;

$^1$H NMR (300 MHz, DMSO-d$_6$) δ8.63 (d, 1H), 7.88 (m, 2H), 7.78 (m, 3H), 7.54 (dd, 1H), 7.48 (m, 2H), 6.46 (d, 1H), 5.13 (m, 1H), 4.02 (m, 1H), 3.28 (m, 1H), 1.58 (m, 2H), 1.52 (d, 3H), 1.38–1.06 (m, 9H), 0.77 (m, 1H), 0.63 (m, 1H);

Anal. calcd for $C_{22}H_{30}N_2O_2S$•HCl: C, 67.59; H, 7.99; N, 7.17. Found: C, 67.42; H, 8.03; N, 7.08.

Example 132

(2RS,3R)-3-amino-4-cyclohexyl-2-hydroxy-N-((1R)-1-(2-naphthyl)ethyl)butanamide hydrochloride The product of example 23A and (R)-1-amino-1-(2-naphthyl)ethane were processed as in example 24 to provide the title compound.

MS (ESI) m/e 355 (M+H)$^+$;

$^1$H NMR (300 MHz, DMSO-d$_6$) δ8.67 (d, 1H), 7.83 (m, 5H), 7.56 (dd, 1H), 7.48 (m, 2H), 6.49 (d, 1H), 5.13 (m, 1H), 4.09 (t, 1H), 3.28 (m, 1H), 1.58 (m, 2H), 1.50 (d, 3H), 1.38–1.06 (m, 9H), 0.77 (m, 1H), 0.63 (m, 1H).

Example 133

(2RS,3R)-3-amino-4-cyclohexyl-2-hydroxy-N-((1S)-1-(1-naphthyl)ethyl)butanamide hydrochloride The product of example 23A and (S)-1-amino-1-(1-naphthyl)ethane were processed as in example 24 to provide the title compound.

MS (ESI) m/e 355 (M+H)$^+$;

$^1$H NMR (300 MHz, DMSO-d$_6$) δ8.69 (d, 1H), 8.13 (d, 1H), 7.94 (dd, 1H), 7.81 (m, 3H), 7.60 (d, 1H), 7.52 (m, 2H), 6.47 (d, 1H), 5.77 (m, 1H), 3.99 (t, 1H), 3.23 (m, 1H), 1.61 (m, 2H), 1.57 (d, 3H), 1.38–1.11 (m, 9H), 0.78–0.60 (m, 2H);

Anal. calcd for $C_{22}H_{30}N_2O_2S$•HCl; C, 67.59; H, 7.99; N, 7.17. Found: C, 67.25; H, 7.92; N, 6.96.

Example 134

(2RS,3R)-3-amino-4-cyclohexyl-2-hydroxy-N-((1R)-1-(1-naphthyl)ethyl)butanamide hydrochloride The product of example 23A and (R)-1-amino-1-(1-naphthyl)ethane were processed as in example 24 to provide the title compound.

MS (ESI) m/e 355 (M+H)$^+$;

$^1$H NMR (300 MHz, DMSO-d$_6$) δ8.71 (d, 1H), 8.14 (d, 1H), 7.94 (dd, 1H), 7.82 (d, 1H), 7.79 (bds, 2H), 7.60 (d, 1H), 7.52 (m, 2H), 6.43 (d, 1H), 5.76 (m, 1H), 4.11 (t, 1H, J=5 Hz), 3.23 (m, 1H), 1.61 (m, 2H), 1.53 (d, 3H), 1.38–1.11 (m, 9H), 0.81 (m, 1H), 0.63 (m, 1H);

Anal. calcd for $C_{22}H_{30}N_2O_2S$•HCl•0.33 H$_2$O: C, 66.58; H, 8.04; N, 7.06. Found: C, 66.46; H, 8.07; N, 6.81.

Example 135 ethyl (2RS,3R,2'R)-2-((3-amino-4-cyclohexyl-2-hydroxybutanoyl)amino)-3-fluoropropanoate trifluoroacetate

Example 135A

HB-fluoro-DL-alanine was processed as in example 1D to provide the title compound.

MS (APCI+) m/e 208 (M+H)$^+$.

Example 135B

The product of example 135A was processed as in example 137A to provide the title compound.

MS (APCI+) m/e 236 (M+H)$^+$.

Example 135C

The product of example 135B was processed as in example 1F to provide the title compound.

MS (APCI+) m/e 136 (M+H)$^+$.

Example 135D

The product of example 23A and the product of example 135C were processed as in example 1E to provide the title compound.

MS (APCI+) m/e 419 (M+H)$^+$.

Example 135E

A solution of example 135D (0.27 g, 0.62 mmol) in dichloromethane (3 mL) containing trifluoroacetic acid (2 mL) was stirred at ambient temperature for 3 hours, evaporated to dryness, suspended in ethyl ether, then concentrated and vacuum dried to give the title compound (0.24 g).

MS (APCI) m/e 336 (M+H)$^+$;

$^1$H NMR (300 MHz, DMSO-d$_6$) δ7.75 (m, 2H), 6.43 (m, 1H), 6.18 (m, 2H), 5.84 (m, 1H), 4.26 (m, 1H), 4.13 (m, 3H), 3.38 (m, 1H), 1.67 (m, 8H), 1.28 (m, 1H), 1.19 (m, 3H), 1.10 (m, 2H).

Example 136

(2RS,3R)-3-amino-4-cyclohexyl-2-hydroxy-N-(2-hydroxy-1-(hydroxymethyl)ethyl)butanamide trifluoroacetate

Example 136A

N-(Benzyloxycarbonyl)-O-(t-butyl)-L-Serine was processed as in example 1A to provide the title compound.

MS (ESI+Q1MS) m/e 282 (M+H)+

Example 136B

The product of example 136A was processed as in example 106.1A to provide the title compound.
MS (APCI+) m/e 311 (M+H)+

Example 136C

The product of example 23A and the product of example 136B were processed as in examples 1E and 135B to provide the title compound.
MS (APCI) m/e 275 (M+H)+;
$^1$H NMR (300 MHz, D2O) δ7.64 (m, 2H), 6.49 (m, 1H), 4.70 (m, 1H), 4.04 (m, 2H), H), 3.78 (m, 2H), 3.42 (m, 2H), 3.35 (m, 2H), 1.64 (m, 4H), 1.41 (m, 3H), 1.22 (m, 3H), 0.89 (m, 1H).

Example 137

4-(tert-butyl)benzyl (2RS,3R,2'R)-2-((3-amino-4-cyclohexyl-2-hydroxybutanoyl)amino-3-hydroxypropanoate trifluoroacetate

Example 137A

A solution of N-(t-butyloxycarbonyl)-O-(t-butyl)-L-Serine (0.54 g, 2.1 mmol) and DCC (0.47 g, 2.2 mmol) in CH$_2$Cl$_2$(5 mL) was stirred at 0° C. for 15 minutes, treated with para-t-butyl benzyl alcohol (0.33 g, 2.0 mmol) and catalytic DMAP and stirred for 16 hours. The solution was evaporated to dryness and the residue was purified by flash chromatography on silica gel with 5% ethyl acetate/toluene to provide the designated compound (0.49 g).
MS (APCI+) m/e 311 (M+H)+

Example 137B

The product of example 137A was processed as in examples 1F, 1E, and 135B to provide the title compound.
MS (APCI) m/e 435 (M+H)+;
$^1$H NMR (300 MHz, D2O) δ7.72 (m, 2H), 7.41 (m, 3H), 7.28 (m, 1H), 5.40 (s, 2H), 5.14 (m, 2H), 4.89 (m, 1H), 4.70 (m, 2H), 4.12 (m, 1H), 3.76 (m, 1H), 1.64 (m, 6H), 1.42 (m, 2H), 1.28 (s, 9H), 1.14 (m, 1H), 0.84 (m, 2H).

Example 138

4-nitrobenzyl (2RS,3R,2'S)-2-((3-amino-4-cyclohexyl-2-hydroxybutanoyl)amino)-3-hydroxypropanoate trifluoroacetate

Example 138A

N-BOC-O-(t-Butyl)-L-Serine and 4-nitro-benzyl alcohol were processed as in example 137A to provide the title compound.

Example 138B

The product of example 23A and the product of example 138 were processed as in example 138B to provide the title compound.
MS (APCI) m/e 424 (M+H)+;
$^1$H NMR (300 MHz, DMSO-d$_6$) δ8.86 (m, 1H), 8.23 (d, 2H), 7.67 (m, 1H), 7.63 (d, 2H), 5.32 (s, 2H), 4.93 (m, 1H), 4.76 (m, 2H), 4.48 (m, 1H), 4.13 (m, 1H), 3.78 (m, 2H), 1.62 (m, 6H), 1.40 (m, 2H), 1.18 (m, 3H).

Example 139

3-nitrobenzyl (2RS,3R,2'S)-2-((3-amino-4-cyclohexyl-2-hydroxybutanoyl)amino)-3-hydroxypropanoate trifluoroacetate N-BOC-O-(t-Butyl)-L-Serine and 3 nitro-benzyl alcohol were processed as in examples 137A and 137B to provide the title compound.
MS (APCI) m/e 424 (M+H)+;
$^1$H NMR (300 MHz, DMSO-d$_6$) δ8.80 (m, 1H), 8.24 (m, 1H), 7.70 (m, 2H), 5.32 (m, 2H), 4.91 (m, 1H), 4.74 (m, 2H), 4.13 (m, 1H), 3.32 (m, 2H), 1.63 (m, 6H), 1.40 (m, 2H), 1.15 (m, 2H) 0.80 (m, 1H).

Example 140

4-(trifluoromethyl)benzyl (2RS,3R,2'S)-2-((3-amino-4-cyclohexyl-2-hydroxybutanoyl)amino)-3-hydroxypropanoate trifluoroacetate N-BOC-O-(t-Butyl)-L-Serine and 4-(trifluoromethyl) benzyl alcohol were processed as in examples 137A and 137B to provide the title compound.
MS (APCI) m/e 447 (M+H)+;
$^1$H NMR 300 MHz, DMSO-d$_6$) δ8.82 (m, 1H), 7.74 (m, 3H), 7.58 (m, 1H), 5.28 (s, 2H), 4.91 (m, 1H), 4.48 (m, 1H), 4.23 (m, 2H), 4.21 (m, 1H), 3.83 (m, 2H), 1.65 (m, 6H), 1.40 (m, 2H), 1.18 (m, 2H), 0.79 (m, 1H).

Example 141

3-(trifluoromethoxy)benzyl (2RS,3R,2'S)-2-((3-amino-4-cyclohexyl-2-hydroxybutanoyl)amino)-3-hydropanoate trifluoroacetate N-BOC-O-(t-Butyl-L-Serine and 3-(trifluoromethoxy) benzyl alcohol were processed as in examples 137A and 137B to provide the title compound.
MS (APCI) m/e 463 (M+H)+;
$^1$H NMR (300 MHz, DMSO-d$_6$) δ8.78 (m, 1H), 7.73 (m, 2H), 7.50 (m, 1H), 7.37 (m, 3H), 5.24 (m, 2H), 4.90 (m, 1H), 4.83 (m, 2H), 4.11 (m, 1H), 4.05 (m, 1H), 3.99 (m, 2H), 1.62 (m, 6H), 1.40 (m, 2H), 1.15 (m, 2H), 0.82 (m, 1H).

Example 142

(2RS,3R)-3-amino-4-cyclohexyl-N-(4-fluorophenethyl)-2-hydroxybutanamide hydrochloride The product of example 23A and 4-fluoro phenethylamine were processed as in example 101 to provide the title compound.
MS (APCI) m/e 323 (M+H)+;
$^1$H NMR (300 MHz, MeOH-d$_4$) δ7.25 (m, 2H), 7.00 (m, 2H), 4.10 (d, 1H), 3.60 (m, 2H), 3.40 (m, 2H), 2.85 (t, 2H), 1.70 (m, 5H), 1.40 (m, 6H), 0.90 (m, 2H).

Example 143

(2RS,3R)-3-amino-4-cyclohexyl-2-hydroxy-N-(4-methylphenyl)butanamide

The product of example 23A and p-toluidine were processed as in example 101 to provide the title compound.
MS (APCI) m/e 291 (M+H)+
$^1$H NMR (300 MHz, MeOH-d$_4$) δ7.52 (d, 2H), 7.16 (d, 2H), 4.28 (d, 1H), 3.65 (m, 1H), 2.31 (s, 3H), 0.92–1.86 (m, 13H).

Example 144

(2RS,3R)-3-amino-4-cyclohexyl-N-(4-fluorophenyl)-2-hydroxybutanamide

The product of example 23A and 4-fluoroaniline were processed as in example 101 to provide the title compound.
MS (APCI) m/e 295 (M+H)+
$^1$H NMR (300 MHz, MeOH-d$_4$) δ7.65 (q, 2H), 7.07 (t, 2H), 4.29 (d, 1H), 3.74 (m, 1H), 0.92–1.88 (m, 13H).,

Example 145

(2RS,3R)-3-amino-4-cyclohexyl-2-hydroxy-N-(4-methoxyphenyl)butanamide

The product of example 23A and p-anisidine were processed as in example 101 to provide the title compound.
MS (APCI) m/e 307 (M+H)+
$^1$H NMR (300 MHz, MeOH-d$_4$) δ7.54 (d, 2H), 6.90 (d, 2H), 4.29 (d, 1H), 3.80 (s, 3H), 3.67 (m, 1H), 0.92–1.88 (m, 13H).

Example 146

(2RS,3R)-3-amino-4-cyclohexyl-2-hydroxy-N-(2-methoxyphenyl)butanamide

The product of example 23A and o-anisidine were processed as in example 101 to provide the title compound.
MS (APCI) m/e 307 (M+H)+
$^1$H NMR (300 MHz, MeOH-d$_4$) δ8.28 (dd, 1H), 7.03–7.15 (m, 2H), 6.94 (td, 1H), 4.34 (d, 1H), 3.91 (s, 3H), 3.77 (m, 1H), 0.96–1.89 (m, 13H).

Example 147

(2RS,3R)-3-amino-N-(4-chlorophenyl)-4-cyclohexyl-2-hydroxybutanamide

The product of example 23A and 4-chloroaniline were processed as in example 101 to provide the title compound.
MS (APCI) m/e 311 (M+H)+
$^1$H NMR (300 MHz, MeOH-d$_4$) δ7.67 (d, 2H), 7.33 (d, 2H), 4.30 (d, 2H), 3.74 (m, 1H), 0.92–1.86 (m, 13H).

Example 148

(2RS,3R)-3-amino-N-(3-chlorophenyl)-4-cyclohexyl-2-hydroxybutanamide

The product of example 23A and 3-chloroaniline were processed as in example 101 to provide the title compound.
MS (APCI) m/e 311 (M+H)+
$^1$H NMR (300 MHz, MeOH-d$_4$) δ7.87 (t, 1H), 7.15 (qd, 1H), 7.32 (t, 1H), 7.14 (qd, 1H), 4.31 (d, 1H), 3.73 (m, 1H), 0.93–1.87 (m, 13H).

Example 149

(2RS,3R)-3-amino-N-(2-chlorophenyl)-4-cyclohexyl-2-hydroxybutanamide

The product of example 23A and 2-chloroaniline were processed as in example 101 to provide the title compound.
MS (APCI) m/e 311 (M+H)+
$^1$H NMR (300 MHz, MeOH-d$_4$) δ8.33 (dd, 1H), 7.48 (dd, 1H), 7.34 (dt, 1H), 7.16 (dt, 1H), 4.40 (d, 1H), 3.80 (m, 1H), 2.69 (s, 1H), 0.96–1.88 (m, 13H).

Example 150

(2RS,3R)-3-amino-N-(4-(tert-butyl)phenyl-4-cyclohexyl-2-hydroxybutanamide

The product of example 23A and 4-tert-butylaniline were processed as in example 101 to provide the title compound.
MS (APCI) m/e 333 (M+H)+
$^1$H NMR (300 MHz, MeOH-d$_4$) δ7.57 (d, 2H), 7.54 (d, 2H), 4.28 (d, 1H), 3.72 (m, 1H), 1.33 (s, 9H), 0.92–1.88 (m, 13H).

Example 151

(2RS,3R)-3-amino-4-cyclohexyl-2-hydroxy-N-(3-(trifluoromethyl)phenyl)butanamide

The product of example 23A and 3-(trifluoromethyl)aniline were processed as in example 101 to provide the title compound.
MS (APCI) m/e 345 (M+H)+
$^1$NMR (300 MHz, MeOH-d$_4$) δ8.16 (s, 1H), 7.86 (d, 1H), 7.54 (t, 1H), 7.43 (d, 1H), 4.33 (d, 1H), 3.77 (m, 1H), 0.93–1.87 (m, 13H).

Example 152

(2RS,3R)-3-amino-4-cyclohexyl-2-hydroxy-N-(4-(trifluoromethyl)phenyl)butanamide

The product of example 23A and 4-(trifluoromethyl)aniline were processed as in example 101 to provide the title compound.
MS (APCI) m/e 345 (M+H)+
$^1$H NMR (300 MHz, MeOH-d$_4$) δ7.89 (d, 2H), 7.64 (d, 2H), 4.34 (d, 1H), 3.74 (m, 1H), 0.95–1.87 (m, 13H).

Example 153

(2RS,3R)-3-amino-4-cyclohexyl-N-(3,4-dichlorophenyl)-2-hydroxybutanamide

The product of example 23A and 3,4-dichloroaniline were processed as in example 101 to provide the title compound.
MS (APCI) m/e 345 (M)+
$^1$H NMR (300 MHz, MeOH-d$_4$) δ8.04 (d, 1H), 7.55 (dd, 1H), 7.47 (d, 1H), 4.32 (d, 1H), 3.75 (m, 1H), 0.92–1.83 (m, 13H).

Example 154

(2RS,3R)-3-amino-4-cyclohexyl-N-(2,4-dichlorophenyl)-2-hydroxybutanamide

The product of example 23A and 2,4-dichloroaniline were processed as in example 101 to provide the title compound.
MS (APCI) m/e 345 (M)+
$^1$H NMR (300 MHz, MeOH-d$_4$) δ8.32 (d, 1H), 7.55 (d, 1H), 7.37 (dd, 1H), 4.40 (d, 1H), 3.66 (m, 1H), 0.95–1.87 (m, 13H).

Example 155

(2RS,3R)-3-amino-N-(4-bromophenyl)-4-cyclohexyl-2-hydroxybutanamide

The product of example 23A and 4-bromoaniline were processed as in example 101 to provide the title compound.
MS (APCI) m/e 356 (M+H)+

¹H NMR (300 MHz, MeOH-d₄) δ7.62 (d, 2H), 7.47 (d, 2H), 4.30 (d, 1H), 3.73 (m, 1H), 0.92–1.85 (m, 13H).

Example 156

(2RS,3R)-3-amino-N-(4-tert-butyl)benzyl-4-cyclohexyl-2-hydroxybutanamide

The product of example 23A and 4-tertbutylbenzylamine were processed as in example 101 to provide the title compound.

MS (APCI) m/e 347 (M+H)⁺

¹H NMR (300 MHz, MeOH-d₄) δ7.35 (d, 2H), 7.24 (d, 2H), 4.39 (q, 2H), 4.16 (d, 1H), 3.58 (m, 1H), 1.39 (s, 9H), 0.87–1.80 (m, 13H).

Example 157

(2RS,3R)-3-amino-4-cyclohexyl-2-hydroxy-N-(3-trifluoromethyl)benzyl)butanamide

The product of example 23A and 3-(trifluoromethyl)benzylamine were processed as in example 101 to provide the title compound.

MS (APCI) m/e 359 (M+H)⁺

¹H NMR (300 MHz, MeOH-d₄) δ7.64 (s, 1H), 7.57 (m, 3H), 4.50 (q, 2H), 4.20 (d, 1H), 3.58 (m, 1H), 0.82–1.80 (m, 13H).

Example 158

(2RS,3R)-3-amino-4-cyclohexyl-2-hydroxy-N-(4-(trifluoromethyl)benzyl)butanamide

The product of example 23A and 4-(trifluoromethyl)benzylamine were processed as in example 101 to provide the title compound.

MS (APCI) m/e 359 (M+H)⁺

¹H NMR (300 MHz, MeOH-d₄) δ7.63 (d, 2H), 7.51 (d, 2H), 4.50 (q, 2H), 4.20 (d, 1H), 3.62 (m, 1H), 0.86–1.80 (m, 13H).

Example 159

(2RS,3R)-3-amino-N-(2-chlorobenzyl)-4-cyclohexyl-2-hydroxybutanamide

The product of example 23A and 3-chlorobenzylamine were processed as in example 101 to provide the title compound.

MS (APCI) m/e 325 (M+H)⁺

¹H NMR (300 MHz, MeOH-d₄) δ 7.40 (M, 2H), 7.27 (m, 2H), 4.55 (q, 2H), 4.22 (d, 1H), 3.61 (m, 1H), 0.88–1.81 (m, 13H).

Example 160

(2RS,3R)-3-amino-4-cyclohexyl-2-hydroxy-N-(2-methoxy-5-nitrophenyl)butanamide hydrochloride The product of example 23A and 2-methoxy-5nitroaniline were processed as in example 101 to provide the title compound.

MS (APCI) m/e 352 (M+H)+;

¹H NMR (300 MHz, MeOH-d₄) δ 9.30 (d, 0.5H), 8.10 (m, 1H), 7.25 (d, 1H), 4.40 (d, 1H), 4.08 (s, 3H), 3.82 (m, 1H), 3.75 (m, 1H), 3.65 (m, 1), 3.58 (m, 1H), 1.75 (m, 5H), 1.40 (m, 6H), 1.05 (m, 2H).

Example 161

(2RS,3R)-3-amino-4-cyclohexyl-N-(3,5-dimethoxyphenyl)-2-hydroxybutanamide hydrochloride The product of example 23A and 3.5-dimethoxyaniline were processed as in example 101 to provide the title compound.

MS (APCI) m/e 337 (M+H)+;

¹H NMR (300 MHz, MeOH-d₄) δ 6.92 (d, 2H), 6.60 (t, 1H), 4.28 (d, 1H), 3.78 (s, 6H), 3.73 (m, 1H), 3.65 (m, 1H), 3.58 (m, 1H), 1.75 (m, 5H), 1.40 (m, 6H), 1.00 (m, 2H).

Example 162

(2RS,3R)-3-amino-4-cyclohexyl-2-hydroxy-N-(3-phenoxyphenyl)butanamide hydrochloride The product of example 23A and 3-phenoxyaniline were processed as in example 101 to provide the title compound.

MS (APCI) m/e 369 (M+H)+;

¹H NMR (300 MHz, MeOH-d₄) δ 7.40 (m, 5H), 7.10 (m, 4H), 6.75 (m, 1H), 4.28 (d, 1H), 3.72 (m, 1H), 3.66 (m, 2H), 3.58 (m, 1H), 1.75 (m, 5H), 1.50 (m, 2H), 1.30 (m, 4H), 1.00 (m, 2H).

Example 163

(((2RS,3R)-3-amino-4cyclohexyl-2-hydroxybutanoyl)amino)(2,5-dimethoxybenzyl)chloronium hydrochloride The product of example 23A and 2,5-dimethoxyaniline were processed as in example 101 to provide the title compound.

MS (APCI) m/e 365 (M+H)+;

¹H NMR (300 MHz, MeOH-d₄) δ 6.42 (d, 2H), 6.35 (t, 1H), 4.11 (d, 1H), 3.75 (s, 6H), 3.65 (m, 1H), 3.55 (m, 2H), 3.40 (m, 1H), 2.78 (t,2H), 1.75 (m, 5H), 1.40 (m, 6H), 0.90 (m, 2H).

Example 164

(2RS,3R)-3-amino-4-cyclohexyl-N-(2,4-dichlorophenethyl)-2-hydroxybutanamide hydrochloride The product of example 23A and 2,4-dichloro phenethylamine were processed as in example 101 to provide the title compound.

MS (APCI) m/e 373 (M+H)+;

¹H NMR (300 MHz, MeOH-d₄) δ 7.45 (d, 1H), 7.30 (m, 2H), 4.00 (d, 1H), 3.60 (m, 2H), 3.45 (m, 2H), 3.00 (m, 2H), 1.70 (m, 5H), 1.40 (m, 6H), 0.90 (m, 2H).

Example 165

(2RS,3R)-3-amino-4-cyclohexyl-N-(2,6-dichlorophenethyl)-2-hydroxybutanamide hydrochloride The product of example 23A and 2,6-dichloroaniline were processed as in example 101 to provide the title compound.

MS (APCI) m/e 373 (M+H)+;

¹H NMR (300 MHz, MeOH-d₄) δ 7.38 (d, 2H), 7.20 (t, 1H), 4.10 (d, 1H), 3.60 (m, 3H), 3.40 (m, 1H), 3.25 (m, 2H), 1.75 (m, 7H), 1.45 (m, 2H), 1.30 (m, 2H), 1.00 (m, 2H).

Example 166

(2RS,3R)-3-amino-4-cyclohexyl-N-(3-fluorophenethyl)-2-hydroxybutanamide hydrochloride The product of example 23A and 3-fluorophenethylamine were processed as in example 101 to provide the title compound.

MS (APCI) m/e 323 (M+H)+;

$^1$H NMR (300 MHz, MeOH-d$_4$) δ 7.30 (m, 1H), 7.00 (m, 3H), 4.10 (d, 1H), 3.65 (m, 1H), 3.58 (m, 2H), 3.40 (m, 1H), 2.85 (t, 2H), 1.75 (m, 5H), 1.60 (m, 2H), 1.45 (m, 2H), 1.28 (m, 2H), 0.95 (m, 2H).

Example 167

(2RS,3R)-3-amino-N-(3,4-bis(benzyloxy)phenethyl)-4-cyclohexyl-2-hydroxybutanamide hydrochloride The product of example 23A and 3,4-dibenzyloxy phenethylamine were processed as in example 101 to provide the title compound.

MS (APCI) m/e 517 (M+H)+;

$^1$H NMR (300 MHz, MeOH-d$_4$) δ 7.45 (t, 5H), 7.35 (m, 5H), 6.95 (m, 2H), 8.78 (d, 1H), 5.10 (d, 4H), 4.10 (d, 1H), 3.65 (m, 1H), 3.55 (m, 2H), 3.40 (m, 1H), 2.75 (m, 2H), 1.75 (m, 5H), 1.60 (m, 2H), 1.40 (m, 4H), 0.90 (m, 2H).

Example 168

(2RS,3R)-3-amino-4-cyclohexyl-2-hydroxy-N-(4-phenoxyphenethyl)butanamide hydrochloride The product of example 23A and 4-phenoxy phenethylamine were processed as in example 101 to provide the title compound.

MS (APCI) m/e 397 (M+H)+; $^1$H NMR (300 MHz, MeOH-d$_4$) δ 7.35 (t, 2H), 7.25 (d, 2H), 7.08 (t, 1H), 6.95 (t, 4H), 4.12 (d, 1H), 3.65 (m, 4H), 2.85 (m, 2H), 1.75 (m, 5H), 1.50 (m, 6H), 0.95 (m, 2H).

Example 169

(2RS,3R)-3-amino-4-cyclohexyl-2-hydroxy-N-(2-(trifluoromethoxy)phenyl)butanamide hydrochlordie The product of example 23A and 2-(trifluoromethoxy) aniline were processed as in example 101 to provide the title compound.

MS (APCI) m/e 361 (M+H)+

$^1$H NMR (300 MHz, MeOH-d$_4$) δ 8.34 (dd, 1H), 7.38 (dt, 2h), 7.26 (dt, 1H), 4.39 (d, 1H), 3.78 (m, 1H), 0.94–1.86 (m, 13H).

Example 170

(2RS,3R)-3-amino-4-cyclohexyl-2-hydroxy-N-(3-(trifluoromethoxy)phenyl)butanamide hydrochloride The product of example 23A and 3-(trifluoromethoxy) aniline were processed as in example 101 to provide the title compound.

MS (APCI) m/e 361 (M+H)+

$^1$H NMR (300 MHz, MeOH-d$_4$) δ 7.85 (s, 1H), 7.57 (qd, 1H), 7.43 (t, 1H), 7.05 (td, 1H), 4.33 (d, 1H), 3.76 (m, 1H), 0.91–1.87 (m, 13H).

Example 171

(2RS,3R)-3-amino-4-cyclohexyl-2-hydroxy-N-(2-methylphenyl)butanamide hydrochloride The product of example 23A and o-anisidine were processed as in example 101 to provide the title compound.

MS (APCI) m/e 291 (M+H)+

$^1$H NMR (300 MHz, MeOH-d$_4$) δ 7.68 (dd, 1H), 7.22 (dq, 2H), 7.13 (dq, 1H), 4.37 (d, 1H), 3.74 (m, 1H), 2.30 (s, 3H), 0.94–1.88 (m, 13H).

Example 172

(2RS,3R)-3-amino-4-cyclohexyl-N-(2,6-dimethylphenyl)-2-hydroxybutanamide hydrochloride The product of example 23A and 2,6-dimethylaniline were processed as in example 101 to provide the title compound.

MS (APCI) m/e 305 (M+H)+

$^1$H NMR (300 MHz, MeOH-d$_4$) δ 7.14 (s, 3H), 4.38 (d, 1H) 3.61 (m, 1H), 2.24 (s, 6H), 0.89–1.89 (m, 13H).

Example 173

(2RS,3R)-3-amino-4-cyclohexyl-2hydroxy-N-(4-iodo-2-methylphenyl)butanamide hydrochloride The product of example 23A and 2-methyl-4-iodoaniline were processed as in example 101 to provide the title compound.

MS (APCI) m/e 416 (M)+

$^1$H NMR (300 MHz, MeOH-d$_4$) δ 8.16 (d, 1H), 7.47 (dd, 1H), 7.30 (d, 1H), 4.38 (d, 1H), 3.74 (m, 1H), 2.25 (s, 3H), 1.91–1.86 (m, 13 H).

Example 174

(2RS,3R)-3-amino-N-(4-anilino-2-methoxyphenyl)-4-cyclohexyl-2-hydroxybutanamide hydrochloride The product of example 23A and 1-amino-2-methoxy-4-(N-phenylamino)benzene were processed as in example 101 to provide the title compound.

MS (APCI) m/e 398 (M+H)+

$^1$H NMR (300 MHz, MeOH-d$_4$) δ 8.05 (d, 1H), 7.24 (t, 2H), 7.10 (d, 2H), 6.88 (m, 1H), 6.78 (d, 1H), 6.70 (dd, 1H), 4.32 (d, 1H), 3.76 (s, 3H), 3.74 (m, 1H), 0.85–1.89 (m, 13H).

Example 175

(2RS,3R)-3-amino-4-cyclohexyl-N-(2-ethoxyphenyl)-2-hydroxybutanamide hydrochloride The product of example 23A and 2-ethyoxyaniline were processed as in example 101 to provide the title compound.

MS (APCI) m/e 321 (M+H)+

$^1$H NMR (300 MHz, MeOH-d$_4$) δ 8.30 (dd, 1H), 7.09 (dt, 1H), 7.03 (t, 1H), 6.93 (dt, 1H), 4.34 (d, 1H), 4.14 (q, 2H), 3.79 (m, 1H), 1.45 (t, 3H), 0.92–1.88 (m, 13H).

Example 176

(2RS,3R)-3-amino-N-(4-chloro-2-methoxy-5-methylphenyl)-4-cyclohexyl-2-hydroxybutanamide hydrochloride The product of example 23A and 2-methoxy-4-chloro-5-toluidine were processed as in example 101 to provide the title compound.

MS (APCI) m/e 355 (M+H)+

$^1$H NMR (300 MHz, MeOH-d$_4$) δ 8.24 (s, 1H), 7.05 (s, 1H), 4.34 (d, 1H), 3.89 (s, 3H), 3.78 (m, 1H), 2.30 (s, 3H) 0.94–189 (m, 13H).

Example 177

(2RS,3R)-3-amino-4cyclohexyl-N-(2,5-dimethoxyphenyl)-2-hydroxybutanamide hydrochloride The product of example 23A and 2,5-dimethoxyaniline were processed as in example 101 to provide the title compound.

MS (APCI) m/e 337 (M+H)+

$^1$H NMR (300 MHz, MeOh-d$_4$) δ 8.00 (d, 1H), 6.95 (d, 1H), 6.67 (dd, 1H), 4.34 (d, 1H), 3.86 (s, 3H), 3.79 (m, 1H), 3.75 (s, 3H), 0.94–1.86 (m, 13H)

Example 178

(2RS,3R)-N-(5-(acetylamino)-2-methoxyphenyl)-3-amino-4-cyclohexyl-2-hydroxybutanamide hydrochloride The product of example 23A and 1-amino-2-methoxy-4-(N-acetylamino)benzene were processed as in example 101 to provide the title compound.

$^1$H NMR (300 MHz, MeOH-d$_4$) δ 8.00 (d, 1H), 7.54 (d, 1H), 7.44 (dt, 1H), 7.42 (td, 1H), 4.48 (d, 1H), 4.41 (d, 1H), 4.06 (s, 3H), 3.83 (m, 1H), 3.15 (s, 3H), 0.89–1.88 (m, 13H).

Example 179

(2RS,3R)-3-amino-4-cyclohexyl-2-hydroxy-N-(2-methoxydibenzo(b,d)furan-3-yl)butanamide hydrochloride The product of example 23A and 3-amino-2-methoxydibenzofuran were processed as in example 101 to provide the title compound.

MS (APCI) m/e 397 (M+H)+

$^1$H NMR (300 MHz, MeOH-d$_4$) δ 8.67 (s, 1H), 7.98 (qd, 1H), 7.69 (s, 1H), 7.54 (q, 1H) 7.43 (qd, 1H), 7.43 (dt, 1H), 4.41 (d, 1H), 4.06 (s, 3H), 3.84 (m, 1H), 0.98–1.90 (m, 13H).

Example 180

(2RS,3R)-3-amino-N-(5-chloro-2,4-dimethoxyphenyl)-4-cyclohexyl-2-hydroxybutanamide hydrochloride The product of example 23A and 2,4-dimethoxy-5-chloraniline were processed as in example 101 to provide the title compound.

MS (APCI) m/e 371 (M+H)+

$^1$H NMR (300 MHz, MeOH-d$_4$) δ 8.29 (s, 1H), 6.80 (s, 1H), 4.33 (d, 1H), 3.95 (s, 3H), 3.90 (s, 3H), 3.74 (m, 1H), 0.82–1.88 (m, 13H).

Example 181

(2RS,3R)-3-amino-4-cyclohexyl-N-(2,5-diethoxyphenyl)-2-hydroxybutanamide hydrochloride The product of example 23A and 2,5-diethoxyaniline were processed as in example 101 to provide the title compound.

MS (APCI) m/e 365 (M+H)+

$^{H\,NMR}$ (300 MHz, MeOH-d$_4$) δ 8.00 (d, 1H), 6.92 (d, 1H), 6.63 (dd, 1H), 4.34 (d, 1H), 4.09 (q, 2H), 4.01 (q, 2H), 3.81 (m, 1H), 1.42 (t, 3H), 1.36 (t, 3H), 0.93–1.89 (m, 13H).

Example 182

(2RS,3R)-3-amino-N-(5-(tert-butyl)-2-methoxyphenyl)-4-cyclohexyl-2-hydroxybutanamide hydrochloride The product of example 23A and 32-methoxy-5-tert-butylaniline were processed as in example 101 to provide the title compound.

MS (APCI) m/e 363 (M+H)+

$^1$H NMR (300 MHz, MeOH-d$_4$) δ 8.42 (d, 1H), 7.15 (dd, 1H), 6.95 (d, 1H), 4.34 (d, 1H), 3.89 (s, 3H), 3.76 (m, 1H), 1.30 (s, 9H), 0.93–1.89 (m, 13H).

Example 183

(2RS,3R)-3-amino-4-cyclohexyl-2-hydroxy-N-(2-phenoxyphenyl)butanamide hydrochloride The product of example 23A and 2-phenoxyaniline were processed as in example 101 to provide the title compound.

MS (APCI) m/e 369 (M+H)+

$^1$H NMR (300 MHz, MeOH-d$_4$) δ 8.35 (dd, 1H), 7.37 (m, 2H), 7.14 (m, 3H), 7.02 (m, 2H), 6.92 (d, 1H), 4.31 (d, 1H), 3.71 (m, 1H), 0.89–1.81 (m, 13H).

Example 184

(2RS,3R)-3-amino-4-cyclohexyl-2-hydroxy-N-(2-methyl-5-nitrophenyl)butanamide hydrochloride The product of example 23A and 2-methyl-5-nitroaniline were processed as in example 101 to provide the title compound.

MS (APCI) m/e 336 (M+H)+

$^1$H NMR (300 MHz, MeOH-d$_4$) δ 8.77 (d, 1H), 8.00 (dd, 1H), 7.50 (d, 1H), 4.44 (d, 1H), 3.79 (m, 1H), 3.19 (d, 1H), 3.06 (d, 1H), 2.42 (s, 3H), 0.82–188 (m, 13H).

Example 185

(2RS,3R)-3-amino-4-cyclohexyl-2-hydroxy-N-(4-phenoxyphenyl)butanamide hydrochloride The product of example 23A and 4-phenoxyaniline were processed as in example 101 to provide the title compound.

MS (APCI) m/e 3.69 (M+H)+

$^1$H NMR (300 MHz, MeOH-d$_4$) δ 7.63 (d, 2H), 7.34 (t, 2H), 7.09 (t, 1H), 6.96 (d, 3H), 4.20 (d, 1H), 3.58 (m, 1H), 0.93–191 (m, 13H).

Example 186

(2RS,3R)-3-amino-4-cyclohexyl-2-hydroxy-N-(4-methoxybenzyl)butanamide hydrochloride The product of example 23A and 4-methoxybenzylamine were processed as in example 101 to provide the title compound.

MS (APCI) m/e 321 (M+H)+

$^1$ H NMR (300 MHz, MeOH-d$_4$) δ 7.25 (d, 2H), 6.87 (d, 2H), 4.35 (q, 2H), 4.15 (d, 1H), 3.77 (s, 3H), 3.57 (m, 1H), 0.85–1.78 (m, 13H).

Example 187

(2RS,3R)-3-amino-4-cyclohexyl-2-hydroxy-N-(4-methylbenzyl)butanamide hydrochloride The product of example 23A and 4-methylbenzylamine were processed as in example 101 to provide the title compound.

MS (APCI) m/e 305 (M+H)+

$^1$H NMR (300 MHz, MeOH-d$_4$) δ 7.20 (d, 2H), 7.12 (d, 2H), 4.38 (q, 2H), 4.11 (d, 1H), 3.53 (m, 1H), 2.30 (s, 3H), 0.86–1.80 (m, 13H).

Example 188

(2RS,3R)-3-amino-N-(3-chlorobenzyl)-4-cyclohexyl-2-hydroxybutanamide hydrochloride The product of example 23A and 3-chlorobenzylamine were processed as in example 101 to provide the title compound.

MS (APCI) m/e 325 (M+H)+

¹H NMR (300 MHz, MeOH-d₄) δ 7.34 (s, 1H), 7.26 (m, 3H), 4.41 (q, 2H), 4.17 (d, 1H), 3.55 (m, 1H), 0.87–1.80 (m, 13H).

Example 189

(2RS,3R)-3-amino-4-cyclohexyl-2-hydroxy-N-(3-methoxybenzyl)butanamide hydrochloride The product of example 23A and 3-methoxybenzylamine were processed as in example 101 to provide the title compound.

MS (APCI) m/e 321 (M+H)+

¹H NMR (300 MHz, MeOH-d₄) δ 7.22 (t, 1H), 6.88 (m, 2H), 6.80 (m, 1H), 4.38 (q, 2H), 3.99 (d, 1H), 3.77 (s, 3H), 0.82–1.80 (m, 13H).

Example 190

(2RS,3R)-3-amino-N-(4-bromobenzyl)-4-cyclohexyl-2-hydroxybutanamide hydrochloride The product of example 23A and 4-bromo benzylamine were processed as in example 101 to provide the title compound.

MS (APCI) m/e 371 (M+H)+;

¹H NMR (300 MHz, MeOH-d₄) δ 7.40 (d, 2H), 7.25 (d, 2H), 4.45 (d, 1H), 4.37 (d, 1H), 4.02 (d, 1H), 3.35 (m, 2H), 1.70 (m, 5H), 1.40 (m, 6H), 0.90 (m, 2H).

Example 191

(2RS,3R)-3-amino-4-cyclohexyl-2hydroxy-N-(3-methylbenzyl)butanamide hydrochloride The product of example 23A and 3-methyl benzylamine were processed as in example 101 to provide the title compound.

MS (APCI) m/e 305 (M+H)+;

¹H NMR (300 MHz, MeOH-d₄) δ 7.25 (m, 4H), 4.90 (d, 1H), 4.30 (d, 1H), 4.12 (d, 1H), 3.55 (m, 2H), 2.35 (s, 3H), 1.70 (m, 5H), 1.40 (m, 6H), 0.90 (m, 2H).

Example 192

(2RS,3R)-3-amino-4-cyclohexyl-2-hydroxy-N-phenethylbutanamide hydrochloride

The product of example 23A and phenethylamine were processed as in example 101 to provide the title compound.

MS (APCI) m/e 305 (M+H)+;

¹H NMR (300 MHz, MeOH-d₄) δ 7.25 (m, 5H), 4.00 (d, 1H), 3.50 (m, 4H), 2.85 (t, 2H), 1.70 (m, 5H), 1.40 (m, 6H), 0.90 (m, 2H).

Example 193

(2RS,3R)-3-amino-N-(4-chlorobenzyl)-4-cyclohexyl-2-hydroxybutanamide hydrochloride The product of example 23A and 4-chlorobenzylamine were processed as in example 101 to provide the title compound.

MS (APCI) m/e 325 (M+H)+

¹H NMR (300 MHz, MeOH-d₄) δ 7.32 (s, 4H), 4.40 (q, 2H), 4.18 (d, 1H), 3.59 (m, 1H), 0.87–1.80 (m, 13H).

Example 194

(2RS,3R)-3-amino-4-cyclohexyl-2-hydroxy-N-(4-methylphenethyl)butanamide hydrochloride The product of example 23A and 3-methyl phenethylamine were processed as in example 101 to provide the title compound.

MS (APCI) m/e 319 (M+H)+;

¹H NMR (300 MHz, MeOH-d₄) δ 7.10 (s, 4H), 4.05 (d, 1H), 3.50 (m, 4H), 2.80 (t, 2H), 2.30 (s, 3H), 1.70 (m, 5H), 1.40 (m, 6H), 0.90 (m, 2H).

Example 195

(2RS,3R)-3-amino-4-cyclohexyl-2-hydroxy-N-(4-methoxyphenethyl)butanamide hydrochloride The product of example 23A and 4-methoxy phenethylamine were processed as in example 101 to provide the title compound.

MS (APCI) m/e 335 (M+H), 669 (2M+H)+;

¹H NMR (300 MHz, MeOH-d₄) δ 7.15 (d, 2H), 6.80 (d, 2H), 4.05 (d, 1H), 3.75 (s, 3H), 3.50 (m, 2H), 3.40 (m, 2H), 2.78 (t, 2H), 1.70 (m, 5H), 1.40 (m, 6H), 0.90 (m, 2H).

Example 196

(2RS,3R)-3-amino-4-cyclohexyl-2-hydroxy-N-(3-methoxyphenethyl)butanamide hydrochloride The product of example 23A and 3-methoxy phenethylamine were processed as in example 101 to provide the title compound.

MS (APCI) m/e 335 (M+H)+;

¹H NMR (300 MHz, MeOH-d₄) δ 7.15 (d, 2H), 6.85 (d, 2H), 4.05 (d, 1H), 3.75 (d, 3H), 3.45 (m, 4H), 2.78 (t, 2H), 1.70 (m, 5H), 1.40 (m, 6H), 0.90 (m, 2H).

Example 197

(2RS,3R)-3-amino-4-cyclohexyl-2-hydroxy-N-(2-methoxyphenethyl)butanamide hydrochloride The product of example 23A and 2-methoxy phenethylamine were processed as in example 101 to provide the title compound.

MS (APCI) m/e 335 (M+H)+;

¹H NMR (300 MHz, MeOH-d₄) δ 7.19 (m, 2H), 6.90 (m, 2H), 4.05 (d, 1H), 3.85 (s, 3H), 3.45 (m, 4H), 2.85 (t, 2H), 1.70 (m, 5H), 1.40 (m, 6H), 0.90 (m, 2H).

Example 198

(2RS,3R)-3-amino-N-(4-chlorophenethyl)-4-cyclohexyl-2-hydroxybutanamide hydrochloride The product of example 23A and 4-chloro phenethylamine were processed as in example 101 to provide the title compound.

MS (APCI) m/e 339 (M+H)+;

¹H NMR (300 MHz, MeOH-d₄) δ 7.25 (m, 4H), 3.92 (d, 1H), 3.48 (m, 4H), 2.82 (t, 2H), 1.71 (m, 5H), 1.40 (m, 6H), 0.90 (m, 2H).

Example 199

(2RS,3R)-3-amino-N-(3-chlorophenethyl)-4-cyclohexyl-2-hydroxybutanamide hydrochloride The product of example 23A and 3-chloro phenethylamine were processed as in example 101 to provide the title compound.

MS (APCI) m/e 339 (M+H)+;

¹H NMR (300 MHz, MeOH-d₄) δ 7.25 (m, 4H), 4.05 (d, 1H), 3.55 (m, 2H), 3.45 (m, 2H), 2.85 (t, 2H), 1.70 (m, 5H), 1.40 (m, 6H), 0.90 (m, 2H).

Example 200

(2RS,3R)-3-amino-4-cyclohexyl-2-hydroxy-N-(3-(trifluoromethyl)phenethyl)butanamide Hydrochloride The product of example 23A and 3-trifluoromethyl phenethylamine were processed as in example 101 to provide the title compound.

MS (APCI) m/e 373 (M+H)+;
$^1$H NMR (300 MHz, MeOH-$d_4$) δ7.55 (m, 4H), 4.05 (d, 1H), 3.6 (m, 2H), 3.45 (m, 2H), 2.95 (t, 2H), 1.70 (m, 5H), 1.40 (m, 6H), 0.90 (m, 2H).

Example 201

(2RS,3R)-3-amino-N-(4-bromophenethyl)-4-cyclohexyl-2-hydroxybutanamide Hydrochloride The product of example 23A and 4-bromo phenethylamine were processed as in example 101 to provide the title compound.

MS (APCI) m/e 385 (M+H)+;
$^1$H NMR (300 MHz, MeOH-$d_4$) δ7.41 (d, 2H), 7.16 (d, 2H), 3.90 (d, 1H), 3.50 (m, 4H), 2.80 (t, 2H), 1.70 (m, 5H), 1.40 (m, 6H), 0.90 (m, 2H).

Example 202

(2RS,3R)-N-(1-adamantyl)-3-amino-4-cyclohexyl-2-hydroxybutanamide Hydrochloride

The product of example 23A and 1-adamantanamine were processed as in example 101 to provide the title compound.

MS (APCI) m/e 335 (M+H)+;
$^1$H NMR (300 MHz, MeOH-$d_4$) δ3.95 (d, 1H), 3.45 (m, 2H), 2.09 (s, 10H), 1.75 (s, 10H), 1.40 (m, 6H), 0.90 (m, 2H).

Example 203

(2RS,3R)-N-(2-adamantyl)-3-amino-4-cyclohexyl-2-hydroxybutanamide Hydrochloride

The product of example 23A and 2-adamantamine were processed as in example 101 to provide the title compound.

MS (APCI) m/e 335 (M+H)+;
$^1$H NMR (300 MHz, MeOH-$d_4$) δ4.15 (d, 1H), 4.00 (s, 1H), 3.55 (m, 2H), 1.80 (m, 19H), 1.40 (m, 6H), 0.90 (m, 2H).

Example 204

(2RS,3R)-3-amino-N-cycloheptyl-4-cyclohexyl-2-hydroxybutanamide Hydrochloride

The product of example 23A and cycloheptylamine were processed as in example 101 to provide the title compound.

MS (APCI) m/e 297 (M+H)+;
$^1$H NMR (300 MHz, MeOH-$d_4$) δ4.00 (d, 1H), 3.90 (m, 1H), 3.41 (m, 2H), 1.50 (m, 23H), 0.90 (m, 2H).

Example 205

(2RS,3R)-3-amino-4-cyclohexyl-N-(cyclohexylmethyl)-2-hydroxybutanamide Hydrochloride The product of example 23A and cyclohexylmethylamine were processed as in example 101 to provide the title compound.

MS (APCI) m/e 297 (M+H)+;
$^1$H NMR (300 MHz, MeOH-$d_4$) δ4.02 (d, 1H), 3.40 (m, 2H), 3.15 (m, 1H), 3.00 (m, 1H), 1.50 (m, 24H).

Example 206

(2RS,3R)-3-amino-N,4-dicyclohexyl-2-hydroxybutanamide Hydrochloride

The product of example 23A and cyclohexylamine were processed as in example 101 to provide the title compound.

MS (APCI) m/e 283 (M+H)+;
$^1$H NMR (300 MHz, MeOH-$d_4$) δ4.05 (d, 1H), 3.70 (m, 1H), 3.45 (m, 2H), 1.50 (m, 21H), 0.90 (m, 2H).

Example 207

(2RS,3R)-3-amino-4-cyclohexyl-N-cyclopentyl-2-hydroxybutanamide Hydrochloride

The product of example 23A and cyclopentylamine were processed as in example 101 to provide the title compound.

MS (APCI) m/e 269 (M+H)+;
$^1$H NMR (300 MHz, MeOH-$d_4$) δ4.15 (m, 1H), 3.95 (d, 1H), 3.35 (m, 2H), 1.50 (m, 19H), 0.90 (m, 2H).

Example 208

(2RS,3R)-3-amino-N-cyclobutyl-4-cyclohexyl-2-hydroxybutanamide Hydrochloride the product of example 23A and cyclobutylamine were processed as in example 101 to provide the title compound.

MS (APCI) m/e 255 (M+H)+;
$^1$H NMR (300 MHz, MeOH-$d_4$) δ4.35 (m, 1H), 4.00 (d, 1H), 3.45 (m, 1H), 2.30 (m, 2H), 2.05 (m, 2H), 1.75 (m, 7H), 1.40 (m, 6H), 0.90 (m, 2H).

Example 209

(2RS,3R)-3-amino-4-cyclohexyl-2-hydroxy-N-(1-methyl-3-phenylpropyl)butanamide Hydrochloride The product of example 23A and 4-phenyl-2-aminopropane were processed as in example 101 to provide the title compound.

MS (ESI) m/e 333 (M+H)+;
$^1$H NMR (300 MHz, MeOH-$d_4$) δ7.40 (m, 5H), 4.10 (d, 1H), 3.90 (m, 1H), 3.75 (m, 1H), 3.68 (m, 1H), 3.55 (m, 2H), 2.65 (m, 2H), 1.75 (m, 7H), 1.45 (m, 2H), 1.20 (m, 5H), 0.90 (m, 2H).

Example 210

(2RS,3R)-3-amino-4-cyclohexyl-2-hydroxy-N-(1-methyl-2-(3-(trifluoromethyl)phenyl)ethyl)butanamide Hydrochloride The product of example 23A and 3(3-trifluoromethylphenyl)-2-aminopropane were processed as in example 101 to provide the title compound.

MS (APCI) m/e 387 (M+H)+;
$^1$H NMR (300 MHz, MeOH-$d_4$) δ7.50 (m, 4H), 4.25 (m, 2H), 4.10 (d, 1H), 4.00 (d, 1H), 3.50 (m, 2H), 3.00 (m, 1H), 2.90 (m, 2H), 1.75 (m, 5H), 1.30 (m, 9H), 0.90 (m, 2H).

Example 211

(2RS,3R)-3-amino-4-cyclohexyl-N-(1.5-dimethylhexyl)-2-hydroxybutanamide Hydrochloride The product of example 23A and 1,5-dimethylhexylamine were processed as in example 101 to provide the title compound.

MS (ESI) m/e 313 (M+H)+;

$^1$H NMR (300 MHz, MeOH-d$_4$) δ4.10 (m, 1H), 3.95 (m, 1H), 3.55 (m, 2H), 1.75 (m, 7H), 1.25 (m, 7H), 1.00 (m, 2H), 0.80 (m, 6H).

Example 212

(2RS,3R)-3-amino-4-cyclohexyl-2-hydroxy-N-(1-methylhexyl)butanamide Hydrochloride The product of example 23A and 1-methylhexylamine were processed as in example 101 to provide the title compound.

MS (ES) m/e 299 (M+H)+;

$^1$H NMR (300 MHz, MeOH-d$_4$) δ4.10 (d, 1H), 3.95 (m, 1H), 3.55 (m, 2H), 1.75 (m, 8H), 1.45 (m, 2H), 1.35 (m, 8H), 1.15 (m, 4H), 0.80 (m, 5H).

Example 213

(2RS,3R)-3-amino-4-cyclohexyl-2-hydroxy-N-(3-isopropoxypropyl)butanamide Hydrochloride The product of example 23A and 3-isopropoxypropylamine were processed as in example 101 to provide the title compound.

MS (ESI) m/e 301 (M+H)+;

$^1$H NMR (300 MHz, MeOH-d$_4$) δ4.15 (d, 1H), 3.60 (m, 2H), 3.55 (m, 4H), 1.75 (m, 6H), 1.40 (m, 8H), 1.15 (d, 6H), 1.00 (m, 2H).

Example 214

(2RS,3R)-3-amino-4-cyclohexyl-2-hydroxy-N-(3-isobutoxypropyl)butanamide Hydrochloride The product of example 23A and 3-isobutoxypropylamine were processed as in example 101 to provide the title compound.

MS (ESI) m/e 315 (M+H)+;

$^1$H NMR (300 MHz, MeOH-d$_4$) δ4.15 (d, 1H), 3.62 (m, 1H), 3.50 (t, 2H), 3.40 (m, 1H), 3.20 (d, 2H), 1.80 (m, 9H), 1.45 (m, 2H), 1.30 (m, 3H), 0.90 (m, 10H).

Example 215

(2RS,3R)-3-amino-4-cyclohexyl-2-hydroxy-N-(4-(4-morpholinyl)phenyl)butanamide Hydrochloride The product of example 23A and 4-morpholinoaniline were processed as in example 101 to provide the title compound.

MS (APCI) m/e 362 (M+H)+;

$^1$H NMR (300 MHz, MeOH-d$_4$) δ7.85 (d, 2H), 7.60 (d, 2H), 4.32 (d, 1H), 4.05 (t, 4H), 3.75 (m, 2H), 3.65 (m, 2H), 3.58 (m, 4H), 1.50 (m, 11H), 1.00 (m, 2H).

Example 216

(2RS,3R)-3-amino-4-cyclohexyl-N-(3,3-diphenylpropyl)-2-hydroxybutanamide Hydrochloride The product of example 23A and 3,3-diphenylpropylamine were processed as in example 101 to provide the title compound.

MS (APCI) m/e 395 (M+H)+;

$^1$H NMR (300 MHz, MeOH-d$_4$) δ7.30 (m, 8H), 7.15 (m, 2H), 4.10 (d, 1H), 4.00 (t, 1H), 3.55 (m, 2H), 3.25 (m, 1H), 3.15 (m, 1H), 2.30 (q, 2H), 1.75 (m, 7H), 1.45 (m, 2H), 1.25 (m, 2H), 0.90 (m, 2H).

Example 217

(2RS,3R)-3-amino-4-cyclohexyl-N-(1,4-dimethylpentyl)-2-hydroxybutanamide Hydrochloride The product of example 23A and 1,4-dimethylpentylamine were processed as in example 101 to provide the title compound.

MS (ESI) m/e 299 (M+H)+;

$^1$H NMR (300 MHz, MeOH-d$_4$) δ4.10 (m, 1H), 3.80 (m, 1H), 3.55 (m, 1H), 1.75 (m, 6H), 1.50 (m, 5H), 1.20 (m, 8H), 0.90 (m, 8H).

Example 218

(2RS,3R)-3-amino-4-cyclohexyl-2-hydroxy-N-methyl-N-(1-naphthylmethyl)butanamide Hydrochloride The product of example 23A and N-methyl-N-(1-naphthyl)methyl amine were processed as in example 24 to provide the title compound.

MS (ESI) m/e 355 (M+H)$^{30}$;

$^1$H NMR (300 MHz, DMSO-d$_6$) δ7.90 (m, 3H), 7.68 (d, 1H), 7.52 (m, 3H), 6.51 (m, 1H), 5.08 (dd, 1.2H), 4.96 (dd, 0.8H), 4.45 (m, 0.6H), 4.20 (m, 0.4H), 3.03 (s, 1.8H), 2.98 (s, 1.2H), 1.80 (m, 1H), 1.63 (m, 3H), 1.43 (m, 2H), 1.31 (m, 2H), 1.17 (m, 4H), 0.81 (m, 2H);

Anal. calcd for $C_{22}H_{30}N_2O_2S \cdot HCl \cdot 0.5C_2H_8O$: C, 66.27; H, 8.11; N, 6.44. Found: C, 65.96; H, 7.82; N, 6.31.

Example 219

(2RS,3R)-3-amino-4-cyclohexyl-2-hydroxy-N-methyl-N-((1S)-1-(1-naphthyl)ethyl)butanamide Hydrochloride The product of example 23A and (S)-N-methyl-N-1-(1-naphthyl)ethyl amine were processed as in example 24 to provide the title compound.

MS (ESI) m/e 369 (M+H)$^+$;

$^1$H NMR (300 MHz, DMSO-d$_6$) δ7.90 (m, 3H), 7.68 (d, 1H), 7.52 (m, 3H), 6.43 (m, 1H), 4.20 (t, 1H), 2.59 (s, 3H), 1.80 (m, 1H), 1.63 (m, 3H), 1.53 (d, 3H), 1.43 (m, 2H), 1.31 (m, 2H), 1.17 (m, 4H), 0.81 (m, 2H);

Anal. calcd for $C_{23}H_{32}N_2O_2S \cdot HCl \cdot 0.75H_2O$: C, 66.01; H, 8.31; N, 6.69. Found: C, 66.25; H, 8.09; N, 6.31.

Example 220

(2RS,3R)-3-amino-4-cyclohexyl-2-hydroxy-N-(2-methoxy-5-(trifluoromethyl)phenyl)butanamide Hydrochloride The product of example 23A and 2-methoxy-5-(trifluoromethoxy)aniline were processed as in example 101 to provide the title compound.

MS (APCI) m/e 375 (M+H)$^+$ $^1$H NMR (300 MHz, MeOH-d$_4$) δ8.70 (d, 1H), 7.44 (dd, 1H), 7.20 (d, 1H), 4.35 (d, 1H), 4.00 (s, 3H), 3.72 (m, 1H), 0.92–1.86 (m, 13H).

Example 221

(2RS,3R)-3-amino-4-cyclohexyl-2-hydroxy-N-(4-methoxy(1,1'-biphenyl)-3-yl)butanamide Hydrochloride The product of example 23A and 2-methoxy-5-phenylaniline were processed as in example 101 to provide the title compound.

MS (APCI) m/e 383 (M+H)+;

¹H NMR (300 MHz, MeOH-d₄) δ7.60 (d, 2H), 7.40 (t, 4H), 7.15 (m, 1H), 7.05 (d, 1H), 4.25 (d, 1H), 3.95 (s, 3H), 3.55 (m, 2H), 1.75 (m, 5H), 1.40 (m, 6H), 0.90 (m, 2H).

Example 222

(2RS,3R)-3-amino-4-cyclohexyl-N-(2,3-dihydro-1, 4-benzodioxin-6-yl)-2-hydroxybutanamide Hydrochloride The product of example 23A and 3,4-ethylenedioxyaniline were processed as in example 101 to provide the title compound.

MS (APCI) m/e 335 (M+H)+;

¹H NMR (300 MHz, MeOH-d₄) δ7.25 (s, 1H), 7.00 (d, 1H), 6.80 (d, 1H), 4.25 (m, 5H), 3.70 (m, 2H), 1.75 (m, 5H), 1.40 (m, 6H), 1.00 (m, 2H).

Example 223

(2RS,3R)-3-amino-N-(3-(benzyloxy)phenyl)-4-cyclohexyl-2-hydroxybutanamide Hydrochloride The product of example 23A and 3-benzyloxyaniline were processed as in example 101 to provide the title compound.

MS (APCI) m/e 383 (M+H)+;

¹H NMR (300 MHz, MeOH-d₄) δ7.20 (m, 6H), 6.90 (d, 1H), 6.40 (m, 2H), 5.05 (d, 2H), 4.30 (d, 1H), 3.70 (m, 2H), 1.75 (m, 5H), 1.40 (m, 6H), 1.00 (m, 2H).

Example 224

(2RS,3R)-3-amino-4-cyclohexyl-N-(3-ethoxyphenyl)-2-hydroxybutanamide Hydrochloride The product of example 23A and 3-ethoxyaniline were processed as in example 101 to provide the title compound.

MS (APCI) m/e 321 (M+H)+;

¹H NMR (300 MHz, MeOH-d₄) δ7.40 (d, 1H), 7.20 (m, 2H), 6.70 (d, 1H), 4.25 (d, 1H), 4.00 (q, 2H), 3.70 (m, 2H), 1.75 (m, 5H), 1.40 (m, 6H), 1.05 (m, 2H).

Example 225

(2RS,3R)-3-amino-4-cyclohexyl-2-hydroxy-N-(3,4,5-trimethoxyphenyl)butanamide Hydrochloride The product of example 23A and 3,4,5-trimethoxyaniline were processed as in example 101 to provide the title compound.

MS (APCI) m/e 367 (M+H)+;

¹H NMR (300 MHz, MeOH-d₄) δ7.10 (s, 2H), 4.30 (d, 1H), 3.80 (m, 11H), 1.80 (m, 5H), 1.50 (m, 2H), 1.30 (m, 4H), 1.00 (m, 2H).

Example 226

(2RS,3R)-3-amino-4-cyclohexyl-N-(2-(2-fluorophenyl)-1-methylethyl)-2-hydroxybutanamide Hydrochloride The product of example 23A and 3(2-fluorophenyl)-2-aminopropane were processed as in example 101 to provide the title compound.

MS (APCI) m/e 337 (M+H)+;

¹H NMR (300 MHz, DMSO) δ7.60 (m, 1H), 7.30 (m, 2H), 7.10 (m, 1H), 4.10 (m, 1H), 2.80 (m, 2H), 1.80 (m, 6H), 1.40 (m, 1H), 1.10 (m, 8H), 0.80 (m, 2H).

Example 227

(2RS,3R)-3-amino-4-cyclohexyl-N-(2-(4-fluorophenyl)-1,1-dimethylethyl)-2-hydroxybutanamide Hydrochloride The product of example 23A and 2-(4-fluorophenyl)-1,1-dimethylethylamine were processed as in example 101 to provide the title compound.

MS (APCI) m/e 351 (M+H)+;

¹H NMR (300 MHz, DMSO) δ7.20 (m, 2H), 7.05 (m, 2H), 3.60 (d, 1H), 3.00 (s, 2H), 1.65 (m, 5H), 1.40 (m, 2H), 1.20 (m, 10H), 0.80 (m, 2H).

Example 228

(2RS,3R)-3-amino-4-cyclohexyl-N-(2,3-dihydro-1H-inden-1-yl)-2-hydroxybutanamide Hydrochloride The product of example 23A and 1-aminoindane were processed as in example 101 to provide the title compound.

MS (APCI) m/e 317 (M+H)+;

¹H NMR (300 MHz, DMSO) δ7.95 (m, 1H), 7.20 (m, 3H), 5.30 (m, 1H), 3.75 (d, 1H), 3.00 (m, 2H), 2.80 (m, 2H), 2.38 (m, 1H), 1.95 (m, 1H), 1.70 (m, 5H), 1.20 (m, 6H), 0.90 (m, 2H).

Example 229

(2RS,3R)-3-amino-4-cyclohexyl-2-hydroxy-N-((1S,2R)-2-phenylcyclopropyl)butanamide Hydrochloride The product of example 23A and trans-2-phenylcyclopropylamine were processed as in example 101 to provide the title compound.

MS (APCI) m/e 317 (M+H)+;

¹H NMR (300 MHz, MeOH-d₄) δ7.25 (t, 2H), 7.15 (m, 3H), 4.12 (d, 1H), 3.55 (m, 2H), 2.95 (m, 1H), 2.15 (m, 1H), 1.75 (m, 7H), 1.45 (m, 2H), 1.25 (m, 4H), 1.00 (m, 2H).

Example 230

(2RS,3R)-3-amino-4-cyclohexyl-2-hydroxy-N-(1,1,3,3-tetramethylbutyl)butanamide Hydrochloride The product of example 23A and tert-octylamine were processed as in example 101 to provide the title compound.

MS (APCI) m/e 313 (M+H)+;

¹H NMR (300 MHz, DMSO) δ3.60 (d, 1H), 2.95 (m, 1H), 1.75 (m, 7H), 1.35 (s, 6H), 1.20 (m, 6H), 0.98 (s, 9H), 0.80 (m, 2H).

Example 231

(2RS,3R)-3-amino-4-cyclohexyl-N-(1,3-dimethylbutyl)-2-hydroxybutanamide Hydrochloride The product of example 23A and 1,3-dimethylbutylamine were processed as in example 101 to provide the title compound.

MS (APCI) m/e 285 (M+H)+;

¹H NMR (300 MHz, DMSO) δ3.70 (m, 1H), 2.95 (m, 1H), 1.80 (m, 8H), 1.40 (m, 2H), 1.20 (m, 4H), 1.05 (d, 3H), 0.85 (m, 8H).

Example 232

Methyl 4-(((2RS,3R)-3-amino-4-cyclohexyl-2-hydroxybutanoyl)amino)-3-thiophenecarboxylate Hydrochloride The product of example 23A and methyl 3-aminothiophene-4-carboxylate were processed as in example 101 to provide the title compound.

MS (APCI) m/e 341 (M+H)+;

$^1$H NMR (300 MHz, MeOH-d$_4$) δ8.40 (s, 1H), 8.10 (s, 1H), 3.95 (d, 1H), 3.80 (s, 3H), 3.10 (m, 1H), 1.70 (m, 5H), 1.20 (m, 6H), 0.90 (m, 2H).

Example 233

(2RS,3R)-N-(1-(1-adamantyl)ethyl)-3-amino-4-cyclohexyl-2-hydroxybutanamide Hydrochloride The product of example 23A and 1-(1-adamantyl) ethylamine were processed as in example 101 to provide the title compound.

MS (APCI) m/e 363 (M+H)+;

$^1$H NMR (300 MHz, DMSO) δ3.75 (d, 1H), 3.50 (m, 2H), 2.90 (m, 2H), 1.95 (s, 2H), 1.65 (m, 10H), 1.45 (m, 8H), 1.20 (m, 5H), 0.95 (d, 3H), 0.80 (m, 2H).

Example 234

(2RS,3R)-3-amino-2-hydroxy-4-ethylthio)butanoyl-((S)-(−)-(1-naphthyl)ethyl)amide the product of example 12A and (S)-(−)-(1-naphtyl) ethylamine were processed as in examples 1E and 1F to yield the title compound.

MS (ESI+Q1MS) m/e 347 (M+H)$^+$, 693 (2M+H)$^+$;

$^1$H NMR (300 MHz, DMSO-d$_6$) δ8.75–7.47 (m, 7H), 6.55 (br., 1H), 4.82–4.75 (m, 1H), 4.15 (d, 1H), 3.60–3.33 (br.m, 3H), 2.68–2.34 (m, 3.6H), 2.18 (q, 0.4H), 1.87–1.68 (m, 2H), 1.58–1.53 (m, 3H), 1.13 (t, 0.6H), 0.98 (t, 0.4H).

Example 235

(2RS,3R)-3-amino-4-cyclohexyl-2-hydroxy-N-(1-napthylmethyl)butanamide Hydrochloride The product of example 23A and 1-naphthylmethylamine were processed as in example 101 to provide the title compound.

MS (APCI) m/e 341 (M+H)+;

$^1$H NMR (300 MHz, MeOH-d$_4$) δ8.15 (d, 1H), 7.85 (q, 2H), 7.50 (m, 4H), 4.90 (m, 2H), 4.15 (d, 1H), 3.50 (m, 2H), 1.70 (m, 5H), 1.40 (m, 6H), 0.90 (m, 2H).

Example 236

(2RS,3R)-3-amino-4-cyclohexyl-2-hydroxy-N-(3-(trifluoromethoxy)benzyl)butanamide Hydrochloride The product of example 23A and 3-trifluoromethoxy benzylamine were processed as in example 101 to provide the title compound.

MS (APCI) m/e 375 (M+H)+;

$^1$H NMR (300 MHz, MeOH-d$_4$) δ7.40 (t, 1H), 7.30 (d, 1H), 7.22 (s, 1H), 7.19 (d, 1H), 4.55 (d, 1H), 4.40 (d, 1H), 4.15 (d, 1H), 3.50 (m, 2H), 1.75 (m, 5H), 1.40 (m, 6H), 0.95 (m, 2H).

Example 237

(2RS,3R)-3-amino-N-(3,5-bis(trifluoromethyl)benzyl)-4-cyclohexyl-2-hydroxybutanamide Hydrochloride The product of example 23A and 3-methylbenzylamine were processed as in example 101 to provide the title compound.

MS (APCI) m/e 427 (M+H)+;

$^1$H NMR (300 MHz, MeOH-d$_4$) δ7.95 (s, 2H), 7.85 (s, 1H), 4.65 (d, 1H), 4.50 (d, 1H), 4.10 (d, 1H), 3.40 (m, 2H), 1.75 (m, 5H), 1.40 (m, 6H), 0.90 (m, 2H).

Example 238

(2RS,3R)-3-amino-4-cyclohexyl-2-hydroxy-N-(2-(trifluoromethyl)benzyl)butanamide

The product of example 23A and 2-trifluoromethyl benzylamine were processed as in example 101 to provide the title compound.

MS (APCI) m/e 359 (M+H)+;

$^1$H NMR (300 MHz, MeOH-d$_4$) δ7.70 (d, 1H), 7.58 (m, 2H), 7.45 (t, 1H), 4.75 (d, 1H), 4.55 (d, 1H), 4.19 (d, 1H), 3.55 (m, 2H), 1.75 (m, 5H), 1.40 (m, 6H), 0.95 (m, 2H).

Example 239

(2RS,3R)-3-amino-4-cyclohexyl-2-hydroxy-N-(4-(trifluoromethoxy)benzyl)butanamide Hydrochloride The product of example 23A and 2-trifluoromethoxy benzylamine were processed as in example 101 to provide the title compound.

MS (APCI) m/e 375 (M+H)+;

$^1$H NMR (300 MHz, MeOH-d$_4$) δ 7.45 (d, 2H), 7.22 (d, 2H), 4.50 (d, 1H), 4.38 (d, 1H), 4.10 (d, 1H), 3.45 (m, 2H), 1.75 (m, 5H), 1.40 (m, 6H), 0.95 (m, 2H).

Example 240

(2RS,3R)-3-amino-N-(6-chloro-3-pyridinyl)-4-cyclohexyl-2-hydroxybutanamide hydrochloride The product of example 23A and 3-amino-6-chloropyridine were processed as in example 101 to provide the title compound.

MS (APCI) m/e 312 (M+H)+;

$^1$H NMR (300 MHz, MeOH-d$_4$) δ 8.70 (s, 1H), 8.20 (d, 1H), 7.40 (d, 1H), 4.30 (d, 1H), 3.80 (m, 2H), 1.80 (m, 6H), 1.50 (m, 2H), 1.30 (m, 3H), 1.00 (m, 2H).

Example 241

(2RS,3R)-3-amino-4-cyclohexyl-2-hydroxy-N-(6-methyl-2-pyridinyl)butanamide hydrochloride The product of example 23A and 2-amino-6-methylpyridine were processed as in example 101 to provide the title compound.

MS (APCI) m/e 292 (M+H)+;

$^1$H NMR (300 MHz, MeOH-d$_4$) δ 8.05 (d, 2H), 7.30 (m, 1H), 4.45 (d, 1H), 3.70 (m, 2H), 2.60 (s, 3H), 1.80 (m, 5H), 1.40 (m, 6H), 1.00 (m, 2H).

Example 242

(2RS,3R)-3-amino-N-(5-chloro-2-methoxyphenyl)-4-cyclohexyl-2-hydroxybutanamide hydrochloride The product of example 23A and 2-methoxy-5-chloroaniline were processed as in example 101 to provide the title compound.

MS (APCI) m/e 341 (M+H)$^+$ $^1$H NMR (300 MHz, MeOH-d$_4$) δ 8.39 (d, 1H), 7.11 (dd, 1H), 7.02 (d, 1H), 4.36 (d, 1H), 3.82 (s, 3H), 3.79 (m, 1H), 0.98–1.88 (m, 13H).

Example 243

(2RS,3R)-3-amino-4-cyclohexyl-2-hydroxy-N-(2-methoxy-5-methylphenyl)butanamide hydrochloride The product of example 23A and 2-methoxy-5-methylaniline were processed as in example 101 to provide the title compound.

MS (APCI) m/e 321 (M+H)$^+$ $^1$H NMR (300 MHz, MeOH-d$_4$) δ 8.13 (s, 1H), 6.92 (s, 2H), 4.33 (d, 1H), 3.89 (s, 3H), 3.78 (m, 1H), 2.28 (s, 3H), 0.92–1.88 (m, 13H).

Example 244

(2RS,3R)-3-amino-N-(4-chloro-2,5-dimethoxyphenyl)-4-cyclohexyl-2-hydroxybutanamide hydrochloride The product of example 23A and 2,5-dimethoxy-4-chloroaniline were processed as in example 101 to provide the title compound.

MS (APCI) m/e 370 (M)$^+$ $^1$H NMR (300 MHz, MeOH-d$_4$) δ 8.23 (s, 1H), 7.09 (s, 1H), 4.36 (d, 1H), 3.88 (s, 3H), 3.85 (s, 3H), 3.79 (m, 1H), 0.97–1.88 (m, 13H).

Example 245

(2RS,3R)-3-amino-4-cyclohexyl-N-(2,3-dimethoxyphenyl)-2-hydroxybutanamide hydrochloride The product of example 23A and 2,3-dimethoxyaniline were processed as in example 101 to provide the title compound.

MS (APCI) m/e 337 (M+H)$^+$ $^1$H NMR (300 MHz, MeOH-d$_4$) δ 7.93 (d, 1H), 7.04 (t, 1H), 6.83 (d, 1H), 4.35 (d, 1H), 3.88 (m, 6H), 3.79 (m, 1H), 0.94–1.88 (m, 13H).

Example 246

(2RS,3R)-3-amino-4-cyclohexyl-N-(3,4-dimethoxyphenyl)-2-hydroxybutanamide hydrochloride The product of example 23A and 3,4-dimethoxyaniline were processed as in example 101 to provide the title compound.

MS (APCI) m/e 337 (M+H)$^+$ $^1$H NMR (300 MHz, MeOH-d$_4$) δ 7.39 (d, 1H), 7.14 (dd, 1H), 6.91 (d, 1H), 4.27 (d, 1H), 3.83 (s, 3H), 3.81 (s, 3H), 3.72 (m, 1H), 0.95–1.86 (m, 13H).

Example 247

(2RS,3R)-3-amino-4-cyclohexyl-2-hydroxy-N-(3-methoxy-4-methylphenyl)butanamide hydrochloride The product of example 23A and 3-methoxy-4-methylaniline were processed as in example 101 to provide the title compound.

MS (APCI) m/e 321 (M+H)$^+$ $^1$H NMR (300 MHz, MeOH-d$_4$) δ 7.35 (s, 1H), 7.06 (d, 2H), 4.28 (d, 1H), 3.82 (s, 3H), 3.72 (m, 1H), 2.14 (s, 3H), 0.91–1.86 (m, 13H).

Example 248

(2RS,3R)-3-amino-4-cyclohexyl-2-hydroxy-N-(4-methoxy-2-naphthyl)butanamide hydrochloride The product of example 23A and 4-methoxy-2-naphthylamine were processed as in example 101 to provide the title compound.

MS (APCI) m/e 357 (M+H)$^+$ $^1$H NMR (300 MHz, MeOH-d$_4$) δ 8.13 (dd, 1H), 7.82 (d, 1H), 7.73 (d, 1H), 7.47 (m, 1H), 7.38 (m, 1H), 7.24 (d, 1H), 4.35 (d, 1H), 4.02 (s, 3H), 3.77 (M, 1H), 0.95–1.88 (m, 13H).

Example 249

(2RS,3R)-3-amino-4-cyclohexyl-2-hydroxy-N-(2-thienylmethyl)butanamide hydrochloride The product of example 23A and 2-aminomethyl)thiophene were processed as in example 101 to provide the title compound.

MS (APCI) m/e 297 (M+H)$^+$ $^1$H NMR (300 MHz, MeOH-d$_4$) δ 7.29 (dd, 1H), 7.02 (dd, 1H), 6.95 (dd, 1H), 4.59 (q, 2H), 4.15 (d, 1H), 3.58 (m, 1H), 0.82–1.80 (m, 13H).

Example 250

(2RS,3R)-3-amino-N-butyl-4-cyclohexyl-2-hydroxy-N-methylbutanamide

The product of example 23A (2.4 g, 8.64 mmole) was dissolved in anhydrous dichloromethane to give 24 ml (solution A). 1-Hydroxybenzotriazole hydrate (HOBT-0.96 g, 7.78 mmole) and 4-(dimethylamino)-pyridine (DMAP-0.096 g, catalytic) were dissolved in 2:1 dichloromethane:N,N-dimethylformamide to make 48 ml (solution B). 1-[3-(dimethylamino)propyl]-3-ethylcarbodiimide hydrochloride (EDCI-2.30 g, 12.96 mmole) was dissolved in anhydrous dichloromethane to give 48 ml (solution C). Solution A was distributed equally into 48 individual reactors. Solution B and solution C were added respectively to these same reactors in equal portions. The reactors were shaken 15 min at room temperature. To one of these reactors, N-methylbutylamine (0.022 ml, 0.27 mmol) was added and the mixture was shaken ca. 20 h. Dichloromethane (2.5 ml) was added to the reaction and shaken. The reactor placed on a liquid phase extractor to wash twice with 1 M sodium bisulfate, once with water, and finally, twice with 2 N sodium bicarbonate. Any residual water was removed and the solvent was concentrated to dryness. The residue was dissolved in 4 M hydrochloric acid in dioxane (1 ml) to cleave the protecting group. After one hour, the solvent was concentrated to dryness. 48 amines were processed at one time in batch mode. Based on HPLC purity, the material was either submitted as is, or sent for preparative HPLC purification prior to submission.

MS (APCI) m/e 271 (M+H)$^+$;

$^1$H NMR (300 MHz, MeOH-d$_4$) δ 4.45 (t, 1H), 3.45 (m, 3H), 3.14 (s, 2H), 2.95 (s, 1H), 1.7 (m, 5H), 1.4 (m, 4H), 0.95 (m, 6H).

Example 251

(2RS,3R)-3-amino-4-cyclohexyl-1-(2,6-dimethyl-4-morpholinyl)-2-hydroxy-1-butanone The product of example 23A and 2,6-dimethylmorpholine were processed as in example 250 to provide the title compound.

MS (APCI) m/e 299 (M+H)$^+$;

$^1$H NMR (300 MHz, MeOH-d$_4$) δ 4.4 (m, 2H), 3.95 (m, 1H), 3.55 (m, 3H), 2.85 (m, 1H), 2.4 (m, 1H), 1.7 (m, 5H), 1.5 (m, 3), 1.2 (m, 9H), 0.95 (m, 2H).

Example 252

(2RS,3R)-3-amino-4-cyclohexyl-2-hydroxy-N,N-bis(methoxymethyl)butanamide

The product of example 23A and bis(2-methoxyethyl)amine were processed as in example 250 to provide the title compound.

MS (APCI) m/e 317 (M+H)⁺;
¹H NMR (300 MHz, MeOH-d₄) δ 4.65 (d, 1H), 3.9 (m, 1H), 3.55 (m, 9H), 3.35 (m, 6H), 1.7 (m, 5H), 1.4 (m, 6H), 0.95 (m, 2H).

Example 253

(2RS,3R)-3-amino-4-cyclohexyl-1-[3,4-dihydro-2 (1H)-isoquinolinyl]-2-hydroxy-1-butanone The product of example 23A and 1,2,3,4-tetrahydroisoquinoline were processed as in example 250 to provide the title compound.

MS (APCI) m/e 317 (M+H)⁺;
¹H NMR (300 MHz, MeOH-d₄) δ 7.2 (m, 4H), 4.7 (m, 2H), 4.55 (d, 1H), 3.8 (m, 2H), 3.5 (m, 1H), 2.95 (m, 2H), 1.7 (m, 5H), 1.4 (m, 6H), 0.95 (m, 2H).

Example 254

(2RS,3R)-3-amino-1-(1-azepanyl)-4-cyclohexyl-2-hydroxy-1-butanone

The product of example 23A and hexamethyleneimine were processed as in example 250 to provide the title compound.

MS (APCI) m/e 283 (M+H)⁺;
¹H NMR (300 MHz, MeOH-d₄) δ 4.45 (d, 1H), 3.65 (m, 2H), 3.55 (m, 3H), 1.6–1.8 (m, 13H), 0.95–1.5 (m, 8H).

Example 255

(2RS,3R)-3-amino-4-cyclohexyl-2-hydroxy-1-[4-phenyl-3,6-dihydro-1(2H)-pyridinyl]-2-butanone The product of example 23A and 4-phenyl-1,2,3,6-tetrahydropyridine hydrochloride were processed as in example 250 to provide the title compound.

MS (APCI) m/e 343 (M+H)⁺;
¹H NMR (300 MHz, MeOH-d₄) δ 7.35 (m, 5H), 6.15 (m, 1H), 4.45 (dd, 1H), 4.25 (m, 2H), 3.85 (m, 2H), 3.55 (m, 1H), 2.6 (m, 2H), 1.7 (m, 5H), 0.95–1.5 (m, 8H).

Example 256

(2RS,3R)-3-amino-N-benzyl-N-butyl-4-cyclohexyl-2-hydroxybutanamide

The product of example 23A and n-butylbenzylamine were processed as in example 250 to provide the title compound.

MS (APCI) m/e 347 (M+H)⁺;
¹H NMR (300 MHz, MeOH-d₄) δ 7.4 (m, 5H), 4.7 (m, 2H), 4.4 (dd, 1H), 3.5 (m, 2H), 3.25 (m, 1H), 2.1–1.7 (m, 15H), 0.92 (m, 5H).

Example 257

(2RS,3R)-3-amino-4-cyclohexyl-1-[(2R,6S)-2,6-dimethylmorpholinyl]-2-hydroxy-1-butanone The product of example 23A and cis-2,6-dimethylmorpholine were processed as in example 250 to provide the title compound.

MS (APCI) m/e 299 (M+H)⁺;
¹H NMR (300 MHz, MeOH-d₄) δ 4.5 (dd, 1H), 4.35 (m, 1H), 3.95 (m, 1H), 3.55 (m, 1H), 2.9 (m, 1H), 2.4 (m, 1H), 1.5–1.7 (m, 8H), 0.95–1.3 (m, 11H).

Example 258

(2RS,3R)-3-amino-N-[(2-chloro-2,3,5-cyclohexatrien-1-yl)methyl]-4-cyclohexyl-2-hydroxy-N-methylbutanamide The product of example 23A and 2-chloro-N-methylbenzylamine were processed as in example 250 to provide the title compound.

MS (APCI) m/e 339 (M+H)⁺;
¹H NMR (300 MHz, MeOH-d₄) δ 7.35 (m, 4H), 4.75 (m, 2H), 4.4–4.55 (dd, 1H), 3.5 (m, 1H), 3.14 (s, 2H), 2.99 (s, 1H), 1.7 (m, 5H), 0.95–1.5 (m, 8H).

Example 259

(2RS,3R)-3-amino-N-(1,3-benzodioxol-5ylmethyl)-4-cyclohexyl-2-hydroxy-N-methylbutanamide The product of example 23A and N-ethyl-3,4 (methylenedioxy)aniline were processed as in example 250 to provide the title compound.

MS (APCI) m/e 349 (M+H)⁺;
¹H NMR (300 MHz, MeOH-d₄) δ 6.9 (d, 1H), 6.83 (d, 1H), 6.78 (dd, 1H), 6.04 (d, 2H), 4.19 (d, 1H), 3.9 m, 1H), 3.5 (m, 1H), 3.25 (m, 1H), 1.65 (m, 5H), 1.4 (m, 2H), 1.0–1.25 (m, 7H), 0.8 (m, 2H).

Example 260

(2RS,3R)-3-amino-4-cyclohexyl-N-(2,4-dichlorobenzyl)-N-ethyl-2-hydroxybutanamide The product of example 23A and 2,4-dichloro-N-ethylbenzylamine were processed as in example 250 to provide the title compound.

MS (APCI) m/e 387 (M+H)⁺;
¹H NMR (300 MHz, MeOH-d₄) δ 7.29–7.52 (m, 3H), 4.65 (m, 2H), 4.35–4.5 (dd, 1H), 3.55 (m, 2H), 3.45 (m, 1H), 1.7 (m, 5H), 1.5 (m, 2H), 1.1–1.4 (m, 7H), 0.95 (m, 2H).

Example 261 ethyl3-[[(2RS,3R)-3-amino-4-cyclohexyl-2-hydroxybutanoyl](benzyl)amino]propanoate The product of example 23A and N-benzyl-3-aminopropionic acid ethyl ester were processed as in example 250 to provide the title compound.

MS (APCI) m/e 391 (M+H)⁺;
¹H NMR (300 MHz, MeOH-d₄) δ 7.3 (m, 5H), 4.7 (m, 3H), 4.1 (m, 2H), 3.4 (m, 1H), 2.6 (m, 2H), 1.7 (m, 5H), 1.15–1.5 (m, 9H), 0.95 (m, 2H).

Example 262

(2RS,3R)-3-amino-4-cyclohexyl-2-hydroxy-1-(1-piperidinyl)-1-butanone

The product of example 23A and piperidine were processed as in example 250 to provide the title compound.

MS (APCI) m/e 387 (M+H)⁺;
¹H NMR (300 MHz, MeOH-d₄) δ 4.45 (d, 1H), 3.7 (m, 2H), 3.5 (m, 3H), 1.7 (m, 9H), 1.5 (m, 4H), 1.3 (m, 4H), 1.0 (m, 2H).

Example 263

(2RS,3R,5'S)-N-[4-(N-phenylhydantoyl)butyl]-3-amino-2-hydroxy-5-(ethylthio)pentananamide hydrochloride Step (a)
Potassium tert-butoxide (112 mg) is added to a solution of N(epsilon)(tert-butoxycarbonyl)-L-lysine methyl ester hydrochloride (300 mg) and phenyl isocyanate (110 mL) in 5 ml of tetrahydrofuran. The resulting mixture is stirred at room temperature for one day. After a similar amount of potassium tert-butoxide is added, the resulting mixture is heated at 65–70° C. for 1 hour. The solvent is removed and ethyl acetate is added to the residue, which is washed with successive portions of brine, 10% KHSO$_4$, brine, 10% NaHCO$_3$, and brine, and dried over anhydrous magnesium sulfate. After removal of the solvents under vacuum, the product residue is treated with 4 N hydrogen chloride in dioxane for 1 hour, and again evaporated to dryness.

Step (b)

The product of Step (a) of Example 12 is reacted with the product of Step (a) of this Example using the method as described in Example 2 to provide the title compound.

Example 264

(2RS,3R,5'R)-N-[4-(N-phenylhydantoyl)-butyl]-3-amino-2-hydroxy-5-(ethylthio)pentananamide hydrochloride Using N(epsilon)(tert-butoxycarbonyl)-D-lysine methyl ester hydrochloride and phenyl isocyanate, the procedure of Example 263 is used to produce the steroisomer shown above.

Example 265

(2RS,3R,4'R)-N-[4-(N-(2,4-dimethoxyphenyl) hydantoyl)propyl]-3-amino-2-hydroxy-4-(ethylthio) pentananamide hydrochloride Using N(epsilon)(tert-butoxycarbonyl)-L-ornithine methyl ester hydrochloride and 2,4-dimethoxyphenyl isocyanate, the procedure of Example 263 is used to produce the compound shown above.

Example 266

(2RS,3R,5'S)-N-[4-(N-(4-triflouromethoxyphenyl) hydantoyl)butyl]3-amino-2-hydroxy-5-(ethylthio) pentananamide hydrochloride Using N(epsilon)(tert-butoxycarbonyl)-L-lysine methyl ester hydrochloride and 4-trifluoromethoxyphenylphenyl isocyanate, the procedure of Example 28 is used to produce the compound shown above.

Example 267

(2RS,3R,5'S,8'S)-N-[4-(3-Methyl-2,5-dioxopiperazin-2-yl)butyl]-3-amino-2-hydroxy-5-(ethylthio)pentananamide hydrochloride Step (a)

L-alanyl-N'-benzyloxycarbonyllysine methyl ester hydrochloride is synthesized by standard peptide synthesis methods well know in the art. The resulting dipeptide ester (250 mg) is dissolved in toluene (20 mL), triethylamine is added, and the mixture is sealed in a tube and heated to 140° C. for 12 hours. The solvent is removed, and the product is dissolved in ethyl acetate (30 ml) and washed with successive portions of brine, 10% KHSO$_4$, and brine, and dried over anhydrous magnesium sulfate. The solvent is removed under vacuum, and the resulting product is deprotected by standard techniques known in the art.

Step (b)

The product of Step (a) of Example 12 and the product of Step (a) above are processed as described in Example 2 to yield the title compound.

Utilizing the procedure of Example 32, and employing amino acids with widely differing side-chains, a number of substituted diketopiperazines can be synthesized and incorporated into compounds of the present invention by the methods detailed in the Examples above.

Example 268

(2RS,3R)-N-[4-(Phthalimido)butyl]-3-amino-2-hydroxy-5-(ethylthio)pentananamide hydrochloride Step (a)

Mono-N-(tert)-butoxycarbonyl-1,4-diaminobutane (190 mg) and phthalic anhydride (150 mg) are dissolved in 5 ml of toluene and gently refluxed in an oil bath (117°–120° C. until all of the starting material is consumed. The reaction mixture is diluted with 15 mL of ethyl acetate, and the organic layer is washed with successive portions of brine, 10% KHSO$_4$, brine, 10% NaHCO$_3$, and brine and dried over anhydrous magnesium sulfate. The solvent is evaporated to yield the crude product which is treated with 4N hydrogen chloride in dioxane for 1 hour. The solvent is removed, taken up in diethyl ether, twice with evaporations to remove the HCl, and dried.

Step (b)

The product of Step (a) of Example 3 and the product of Step (a) above are processed as described in example 2 to provide the title compound.

Utilizing the method detailed in Step (a) of Example 268, a number of N-(aminoalkyl)phthalimides can be synthesized and incorporated into compounds of the present invention. Examples of such N-(aminoalkyl)phthalimides include compounds where q can range from one to six, inclusive, and A can be hydrogen, halogen, lower alkyl, lower alkoxy, nitro, or carboxy.

Example 269

(2RS,3R)-N-(2-thien-2-ylethyl)-3-amino-2-hydroxy-5-(ethylthio)pentanamide hydrochloride The product of Step (a) of Example 12 and 2-(2-aminoethyl)thiophene are processed as described above in Example 2 to provide the title compound.

Example 270

(2RS,3R)-(N-methyl-N-propyl)-3-amino-2-hydroxy-5-(ethylthio)pentanamide hydrochloride The product of Step (a) of Example 12 and N-methyl n-propylamine are processed as described in Example 2 to provide the title compound.

In the same manner, alkylamines and dialkylamines in which the two alkyl groups are the same or are different can be converted to compounds of the present invention by the method detailed in Example 35.

Example 271

(2RS,3R)-N-[2-(g-Aminobutyrolactamyl)ethyl]-3-amino-2-hydroxy-5-(ethylthio)pentanamide The product of Step (a) of Example 12 and 1-amino-2-[g-aminobutyrolactamyl]ethane are processed as described in Example 2 to provide the title compound.

In a similar manner, aminoalkyl lactams can be incorporated into compounds of the present invention my the methods detailed in the Examples given above.

Example 272

(2RS,3S,1'S)N-[(1-carboxyl)ethyl]3-amino-2-thio-5-(methylthio)pentanamide hydrochloride Example 1E (0.40 g, 1.1 mmole) in 3 mL of methylene chloride containing 50% molar excess of triethylamine at 0° C. is treated with methanesulfonyl chloride (0.1 mL, 1.31 mmole). After the reaction is completed, the mixture is washed with brine, 10% KHSO4, dried over MgSO4. To a solution mesylate (0.45 mmole) in 5 mL of THF is added a solution of p-methoxybenzyl mercaptan (0.104 g, 0.675 mmole) in the presence of 1N-NaOH at 0° C. under nitrogen atmosphere. After an additional 30 minutes at room temperature with stirring, the product is purified by silica gel column chromatography, eluting with 10% ethyl acetate in toluene.

Obtained p-methoxybenzyl mercapto derivative (0.4 mmole) is dissolved in 3 mL of methanol. 2N-NaOH is added to adjust pH at around 12. The reaction is worked up according to the general procedure and the product is treated with 4N-HCl in dioxane for 1.5 hours to obtain the title compound.

Example 273

(2RS,3S,1'S)N-[(1-ethoxycarbonyl)ethyl]3-amino-2-oxo-5-(methylthio)pentanamide hydrochloride Example 1E (0.4 g, 1.1 mmole) is oxidized by pyridinium chlorochromate (710 mg, 3.3 mmole) in 5 mL of methylene chloride until the starting material is consumed. The obtained diketone is purified on silica gel column chromatography. The resulting product is processed as described in step (f) in example 1 to yield the title compound.

What is claimed is:

1. A compound having the formula (I):

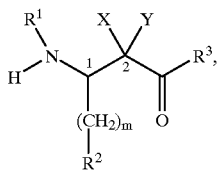

I or a pharmaceutically acceptable salt thereof, wherein the small numerals denote chrial centers in the compound;

m is 1–3;

$R^1$ is selected from the group consisting of
  (1) hydrogen,
  (2) alkyl,
  (3) carboxaldehyde,
  (4) alkanoyl, where the alkanoyl can be optionally substituted with hydroxyl,
  and
  (5) —$(CH_2)_nCO_2R^4$, where n is 0–6, and $R^4$ is selected from the group consisting of
    (a) hydrogen,
    (b) alkyl,
    (c) cycloalkyl,
    (d) (cycloalkyl)alkyl,
    (e) aryl,
    and
    (f) arylalkyl,
  where (c) and (d) can be optionally substituted with 1, 2, or 3 substituents independently selected from the group consisting of
    (i) alkyl,
    (ii) alkoxy,
    and
    (iii) aryl,
    and
  where (e) and (f) can be optionally substituted with 1, 2, or 3 substituents independently selected from the group consisting of
    (i) alkyl,
    (ii) alkanoyl,
    (iii) alkoxy,
    (iv) —$CO_2R^{4'}$, where $R^{4'}$ is selected from the group consisting of,
      (a) hydrogen,
      (b) alkyl,
      (c) cycloalkyl,
      (d) (cycloalkyl)alkyl,
      (e) eryl,
      and
      (f) arylalkyl,
    (v) alkanoyloxy,
    (vi) carboxaldehyde,
    (vii) cycloalkyl,
    (viii) cycloalkenyl,
    (ix) halo,
    (x) nitro,
    (xi) perfluoroalkyl,
    (xii) perfluoroalkoxy,
    (xiii) arylsulfonylalkyl,
    (xiv) aryloylalkyloxycarbonylalkyl,
    (xv) —$NR^6R^{6'}$, where $R^6$ and $R^{6'}$ are independently selected from the group consisting of
      (1) hydrogen,
      (2) alkyl optionally substituted with alkoxy,
      (3) aryl,
      (4) arylalkyl,
      and
      (5') a nitrogen-protecting group,
    (xvi) —$SO_2NR^6R^{6'}$, where $R^6$ and $R^{6'}$ are defined above,
    and
    (xvii) —$C(O)NR^6R^{6'}$, where $R^6$ and $R^{6'}$ are defined above;

$R^2$ is selected from the group consisting of
  (1) alkyl,
  (2) cycloalkyl,
  (3) (cycloalkyl)alkyl,
  (4) —$C(H)(SR^{15})(SR^{15'})$, where $R^{15}$ and $R^{15'}$ are alkyl, or $R^{15}$ and $R^{15'}$, together with the sulfurs to which they are attached, are a 1,3-dithiolane ring of a 1,3-dithiane ring,
  (5) aryl,
  (6) arylalkyl,
  and
  (7) —$SR^5$, where $R^5$ is selected from the group consisting of
    (a) alkyl,
    (b) cycloalkyl,
    (c) (cycloalkyl)alkyl,
    and
    (d) benzyl, where the benzyl can be optionally substituted with 1, 2, or 3 substituents independently selected from the group consisting of (i) alkyl,
(ii) alkanoyl,
(iii) alkoxy,
(iv) —CO$_2$R$^4$, where R$^4$ is defined above,
(v) alkanoyloxy,
(vi) carboxaldehyde,
(vii) cycloalkyl,
(viii) cycloalkenyl,
(ix) halo,
(x) nitro,
(xi) perfluoroalkyl,
(xii) perfluoroalkoxy,
(xiii) —NR$^6$R$^{6'}$, where R$^6$ and R$^{6'}$ are defined above,
(xiv) —SO$_2$NR$^6$R$^{6'}$, where R$^6$ and R$^{6'}$ are defined above, and
(xv) —C(O)NR$^6$R$^{6'}$, where R$^6$ and R$^{6'}$ are defined above;

R$^3$ is selected from the group consisting of
(1) and aminoacyl group optionally capped with a carboxyl protecting group,
(2) —N(R$^6$)(CH$_2$)$_p$R$^7$, where p is 0–6, R$^6$ is defined above, and R$^7$ is selected from the group consisting of
  (a) hydrogen,
  (b) alkyl, where the alkyl can be optionally substituted with 1, 2, 3, or 4 substituents independently selected from the group consisting of
    (i) oxo,
    (ii) thioxo,
    (iii) alkoxy,
    (iv) —CO$_2$R$^4$, where R$^4$ is defined above,
    (v) alkanoyloxy,
    (vi) carboxaldehyde,
    (vii) cycloalkyl,
    (viii) cycloalkenyl,
    (ix) halo,
    (x) nitro,
    (xi) perfluoroalkyl,
    (xii) perfluoroalkoxy,
    (xiii) —NR$^6$R$^{6'}$, where R$^6$ and R$^{6'}$ are defined above,
    (xiv) —SO$_2$NR$^6$R$^{6'}$, where R$^6$ and R$^{6'}$ are defined above,
    (xv) —C(O)NR$^6$R$^{6'}$, where R$^6$ and R$^{6'}$ are defined above,
    (xvi) aryl, and
    (xvii) hydroxy,
  (c) cycloalkyl, where the cycloalkyl can be optionally substituted with 1, 2, or 3 substituents indepdently selected from the group consisting of
    (i) alkyl,
    (ii) halo,
    (iii) oxo, and
    (iv) aryl,
  (d) aryl, where the aryl can be optionally substituted with 1, 2, or 3 substituents independently selected from the group consisting of
    (i) alkyl,
    (ii) alkanoyl,
    (iii) alkoxy,
    (iv) —CO$_2$R$^4$, where R$^4$ is defined above,
    (v) alkanoyloxy,
    (vi) carboxyaldehyde,
    (vii) cycloalkyl,
    (viii) cycloalkenyl,
    (ix) halo,
    (x) nitro,
    (xi) perfluoroalkyl,
    (xii) perfluoroalkoxy,
    (xiii) —NR$^6$R$^{6'}$, where R$^6$ and R$^{6'}$ are defined above,
    (xiv) —SO$_2$NR$^6$R$^{6'}$, where R$^6$ and R$^{6'}$ are defined above,
    (xv) —C(O)NR$^6$R$^{6'}$, where R$^6$ and R$^{6'}$ are defined above,
    (xvi) aryloxy,
    (xvii) arylalkoxy,
    (xvi) aryl, and
    (xvii) hydroxy,
(e) —CO$_2$R$^4$, where R$^4$ is defined above,
(f) —CONR$^6$R$^8$, where R$^6$ is defined above, and R$^8$ is selected from the group consisting of
  (i) hydrogen
  (ii) alkyl, and
  (iii) aryl,
  where (ii) and (iii) can be optionally substituted with one, two, or three groups independently selected from the group consisting of
    (1') alkyl,
    (2') alkanoyl,
    (3') alkoxy,
    (4') —CO$_2$R$^4$, where R$^4$ is defined above,
    (5') alkanoyloxy,
    (6') carboxyaldehyde,
    (7') cycloalkyl,
    (8') cycloalkenyl,
    (9') halo,
    (10') nitro,
    (11') perfluoroalkyl,
    (12') perfluoroalkoxy,
    (13') —NR$^6$R$^{6'}$, where R$^6$ and R$^{6'}$ are defined above,
    (14') —SO$_2$NR$^6$N$^{6'}$, where R$^6$ and R$^{6'}$ are defined above,
    (15') —C(O)NR$^6$R$^{6'}$, where R$^6$ and R$^{6'}$ are defined above,
    (16') aryloxy,
    (17') arylalkoxy,
    (18') aryl, and
    (19') hydroxy,
(g) —NR$^6$R$^8$, where R$^6$ and R$^8$ are defined above, and
(h) —N(R$^6$)SO$_2$R$^{12}$, where R$^6$ is defined previously, and R$^{12}$ is selected from the group consisting of
  (i) alkyl,
  (ii) aryl, and
  (iii) arylalkyl,
  where (ii) and (iii) can be optionally substituted with 1, 2, or 3 groups independently selected from the group consisting of
    (1') alkyl,
    (2') alkanoyl,
    (3') alkoxy,
    (4') —CO$_2$R$^4$, where R$^4$ is defined above,
    (5') alkanoyloxy,
    (6') carboxaldehyde,
    (7') cycloalkyl,
    (8') cycloalkenyl,
    (9') halo,
    (10') nitro,
    (11') perfluoroalkyl,
    (12') perfluoroalkoxy,
    (13') —NR$^6$R$^{6'}$, where R$^6$ and R$^{6'}$ are defined above,
    (14') —SO$_2$NR$^6$R$^{6'}$, where R$^6$ and R$^{6'}$ are defined above,
    (15') —C(O)NR$^6$R$^{6'}$, where R$^6$ and R$^{6'}$ are defined above, (16') aryloxy,
(17') arylalkoxy,
(18') aryl, and
(19') hydroxy, and (3) —O(CH$_2$)$_p$R$^7$ are defined above;

with the proviso that at least one of R$^1$, R$^2$, or R$^3$ has contained therein an aryl or cycloalkyl group;

X is hydroxyl or sulfhydryl;

and

Y is hydrogen;

or

X and Y, taken together with the carbon atom to which they are attached, form a carbonyl or thiocarbonyl;

with the proviso that when X is hydroxyl; Y is hydrogen; R$^3$ is —N(R$^6$)(CH$_2$)$_p$R$^7$ wherein is hydrogen, p is 0–6, and R$^7$ is alkyl, alkoxycarbonyl, carboxyl, or phenyl; and R$^2$ is phenyl, m is not 1;

and with the proviso that when X and Y, together with the carbon atom to which they are attached, are carbonyl; R$^3$ is —N(R$^6$)(CH$_2$)$_p$R$^7$ wherein R$^6$ is hydrogen, p is 0–6, and R$^7$ is alkyl, alkoxycarbonyl, carboxyl, or phenyl; and R$^2$ is phenyl, m is not 1.

2. A compound in accordance with claim 1, or a pharmaceutically acceptable salt thereof, wherein Y is hydrogen and X is hydroxy.

3. A compound in accordance with claim 2, or a pharmaceutically acceptable salt thereof, wherein the stereochemistry at the chiral center designated "2" is of the S configuration.

4. A compound in accordance with claim 2, or a pharmaceutically acceptable salt thereof, wherein the stereochemistry at the chiral center designated "1" is of the R configuration.

5. A compound in accordance with claim 4, or a pharmaceutically acceptable salt thereof, wherein R$^2$ is —SR$^5$.

6. A compound in accordance with claim 5, or a pharmaceutically acceptable salt thereof, selected from the group consisting of (2RS,3R)-N-((2-phenylethyl)-3-amino-2-hydroxy-5-(methylthio)pentanamide,
(2RS,3R)-N-((3-phenylpropyl)-3-amino-2-hydroxy-5-(methylthio)pentanamide,
(2RS,3R)-N-(4-phenylbutyl)-3-amino-2-hydroxy-5-(methylthio)pentanamide,
(2RS,3R)-N-(2-(4-methoxyphenyl)ethyl)-3-amino-2-hydroxy-5-(methylthio)pentanamide,
(2RS,3R)-N-(2-(4-sulfonamidophenyl)ethyl)-3-amino-2-hydroxy-5-(methylthio)pentanamide,
(2RS,3R)-N-(2-(4-phenoxyphenyl)ethyl)-3-amino-2-hydroxy-5-(methylthio)pentanamide,
(2RS,3R)-N-(4-phenyl)butyl)-3-amino-2-hydroxy-5-(ethylthio)pentanamide,
(2RS,3R)-N-(3-(carbobenzyloxy)ethyl)-3-amino-2-hydroxy-5-(ethylthio)pentanamide,
(2RS,3R)-3-amino-2-hydroxy-N-(4-methoxyphenethyl)-5-(methylthio)pentanamide,
(2RS,3R)-N-((2-phenylbutyl)-3-tert-butoxycarbonylamino-2-hydroxy-5-(ethylthio)pentanamide,
(2RS,3R)-N-((2-phenylbutyl)-3-acetylamino-2-hydroxy-5-(ethylthio)pentanamide,
(2RS,3R)-N-((phenylbutyryl)-3-methoxycarbonylamino-2-hydroxy-4-ethylthio)pentanamide,
(2RS,3R)-3-amino-2-hydroxy-N-methyl-5-(methylthio)-N-penethylpentanamide,
(2RS,3R)-N-((phenylbutylryl)-3-tert-butoxycarbonylamino-2-hydroxy-4-ethylthio)pentanamide,
(2RS,3R)-N-((phenylbutyryl)-3-formylamino-2-hydroxy-4-ethylthio)pentanamide,
(2RS,3R)-N-((phenylbutyryl)-3-hydroxymethylcarbonylamino-2-hydroxy-4-ethylthio)pentanamide,
(2RS,3R)-N-((phenylbutyryl)-3-methoxycarbonylmethylamino-2-hydroxy-4-ethylthio)pentanamide,
(2RS,3R,1'S)-N-((1-ethoxycarbonylethyl)-3-amino-2-hydroxy-4-benzylthio)butanamide,
(2RS,3R)-N-(monodansylcadaverenyl)-3-amino-2-hydroxy-5-ethylthio)pentanamide,
and
(2RS,3R)-3-amino-2-hdyroxy-4-ethylthio)butanoyl-((S)-(–)-(1-naphthyl)ethyl)amide.

7. A compound in accordance with claim 4, or a pharmaceutically acceptable salt thereof, wherein R$^2$ is aryl.

8. A compound in accordance with claim 4, or a pharmaceutically acceptable salt thereof, wherein R$^2$ is cycloalkyl.

9. A compound in accordance with claim 8, or a pharmaceutically acceptable salt thereof, selected from the group consisting of (2RS,3R,1'S)-N-((1-ethoxycarbonyl)ethyl)-3-amino-2-hydroxy-4-cyclohexylbutanamide,
(2RS,3R)-N-(2-(carboethoxy)ethyl)-3-amino-2-hydroxy-4-cyclohexylbutanamide,
(2RS,3R)-N-(3-(carboethoxy)propyl)-3-amino-2-hydroxy-4-cyclohexylbutanamide,
(2RS,3R)-N-((phenylbutyryl)-3-amino-2-hydroxy-4-cyclohexyl)butanamide,
(2RS,3R,1'R)-N-((1-ethoxycarbonylethyl)-3-amino-2-hydroxy-4-cyclohexyl)butanamide,
(2RS,3R)-N-((1-methyl-1-ethoxycarbonylethyl)-3-amino-2-hydroxy-4-cyclohexyl)butanamide,
(2RS,3R,1'S)-N-((2-hydroxy-1-ethoxycarbonylethyl)-3-amino-2-hydroxy-4-cyclohexyl)butanamide,
(2RS,3R,1'S)-N-((2-acetoxypropyl)-3-amino-2-hydroxy-4-cyclohexyl)butanamide,
(2RS,3R,2'S)-N-((2-propionyloxypropyl)-3-amino-2-hydroxy-4-cyclohexyl)butanamide,
(2RS,3R,2'S)-N-((2-benzoyloxypropyl)-3-amino-2-hydroxy-4-cyclohexyl)butanamide,
(2RS,3R,2'R)-N-((2-benzoyloxypropyl)-3-amino-2-hydroxy-4-cyclohexyl)butanamide,
(2RS,3R,2'R)-N-((2-propionyloxypropyl)-3-amino-2-hydroxy-4-cyclohexyl)butanamide,
(2RS,3R,2'R)-N-((2-acetoxypropyl)-3-amino-2-hydroxy-4-cyclohexyl)butanamide,
(2RS,3R,1'S)-N-((1-benzyloxycarbonylethyl)-3-amino-2-hydroxy-4-cyclohexyl)butanamide,
(2RS,3R)-N-(monodansylcadavernyl)-3-amino-2-hydroxy-4-cyclohexyl)butanamide,
(2RS,3R)-N-(3-O-methyl-dopaminyl)3-amino-2-hydroxy-4-cyclohexyl)butanamide,
((2RS,3R)-3-amino-2-hydroxy-4-cyclohexyl)butanoyl-L-alanyl-(3-O-methoxydopamine)amide,
(2RS,3R)-3-amino-2-hydroxy-4-cyclohexyl)butanoyl-L-alanyl-(2-hydroxy-5nitrophen-1-yl)amide,
((2RS,3R)-3-amino-2-hydroxy-4-cyclohexyl)butanoyl-L-alanyl-(4-nitro-2-hydroxyphen-1-yl)amide,
ethyl (2RS,3R,2'S)-2-((-3-(acetylamino)-4-cyclohexyl-2-hydroxybutanoyl)amino)propanoate,
(2RS,3R)-3-amino-2-hydroxy-4-cyclohexyl)butanoyl-(4-benzyloxycarbonylamino)butylamide, (2RS,3R)-3-amino-2-hydroxy-4-cyclohexyl)butanoyl-beta-alamine benzyl ester,
(2RS,3R)-3-amino-2-hydroxy-4-cyclohexyl)butanoyl-(4-(4-toluenesulfonyl)aminobutyl)amide,
(2RS,3R)-3-amino-2-hydroxy-4-cyclohexyl)butanoyl-(2-4-toluenesulfonylaminoethyl)amide,
(2RS,3R)-3-amino-2-hydroxy-4-cyclohexyl)butanoyl-(4-aminobutyl)amide,
(2RS,3R)-3-amino-2-hydroxy-4-cyclohexyl)butanoyl-(2-aminoethyl)amide,
(2RS,3R)-3-amino-4-cyclohexyl-2-hydroxy-N-(4-(((3-(trifluoromethyl)phenyl)sulfonyl)amino)butyl)butanamide,
(2RS,3R)-3-amino-4-cyclohexyl-N-(4-(((3,4-dimethoxyphenyl)sulfonyl)amino)butyl)-2-hydroxybutanamide,
(2RS,3R)-N-(4-(((4-(acetylamino)phenyl)sulfonyl)amino)butyl)-3-amino-4-cyclohexyl-2-hydroxybutanamide,
(2RS,3R)-3-amino-4-cyclohexyl-2-hydroxy-N-(4-((2-naphthylsulfonyl)amino)butyl)butanamide,
(2-RS,3R)-3-amino-2-hydroxy-4-cyclohexyl)butanoyl-L-alanine-4-sulfonamide benzyl ester,
(2RS,3R)-3-amino-2-hydroxy-4-cyclohexyl)butanoyl-L-alanine benzyl ester,
(2RS,3R)-3-amino-2-hydroxy-4-cyclohexyl)butanoyl-L-alanine cyclohexyl ester,
(2RS,3R)-3-amino-2-hydroxy-4-cyclohexyl)butanoyl-L-alanine 2-((phenylsulfonyl)methyl)benzyl ester,
(2RS,3R)-3-amino-2-hydroxy-4-cyclohexyl)butanoyl-L-alanine cyclopropyl ester,
(2RS,3R)-3-amino-2-hydroxy-4-cyclohexyl)butanoyl-L-alanine 4-tert-butylbenzyl ester,
(2RS,3R)-3-amino-2-hydroxy-4-cyclohexyl)butanoyl-L-alanine 4-methoxycarbonylbenzyl ester,
(2RS,3R)-3-amino-2-hydroxy-4-cyclohexyl)butanoyl-L-alanine 4-trifluoromethylbenzyl ester,
(2RS,3R)-3-amino-2-hydroxy-4-cyclohexyl)butanoyl-L-alanine-(4-(methyl)phenyl acetic acid phenacyl ester),
(2RS,3R)-3-amino-4-cyclohexyl-N-(2,4-dichlorobenzyl)-2-hydroxybutanamide,
(2RS,3R)-3-amino-4-cyclohexyl-2-hydroxy-N-(3-methoxyphenyl)butanamide,
methyl (2RS,3R,2'R)-2-((3-amino-4-cyclohexyl-2-hydroxybutanoyl)amino)-4-methylpentanoate,
(2RS,3R,1'RS)-3-amino-4cyclohexyl-2-hydroxy-N-(1-(1-naphthyl)ethyl)butanamide,
(2RS,3R)-3-amino-4-cyclohexyl-N-(1,2-dimethylpropyl)-2-hydroxybutanamide,
(2RS,3R)-3-amino-2-hydroxy-4-cyclohexyl)butanoyl-L-alanine,
(2RS,3R)-3-amino-4-cyclohexyl-2-hydroxy-N-phenylbutanamide,
(2RS,3R)-3-amino-N-(2-chlorophenethyl)-4-cyclohexyl-2-hydroxybutanamide,
(2RS,3R)-3-amino-4-cyclohexyl-2-hydroxy-N-(3-phenylpropyl)butanamide,
(2RS,3R)-3-amino-4-cyclohexyl-2-hydroxy-N-(1,2,3,4-tetrahydro-1-naphthalenyl)butanamide,
(2RS,3R)-3-amino-N-(4-(tert-butyl)cyclohexyl)-4-cyclohexyl-2-hydroxybutanamide,
(2RS,3R)-3-amino-4-cyclohexyl-N-(3,5-dichlorophenyl)-2-hydroxybutanamide,
(2RS,3R)-3-amino-4-cyclohexyl-N-(2-ethylhexyl)-2-hydroxybutanamide,
butyl (2RS,3R)-2-((3-amino-4-cyclohexyl-2-hydroxybutanoyl)amino)acetate,
(2RS,3R)-3-amino-4-cyclohexyl-N-(2,4-dimethoxyphenyl)-2-hydroxybutanamide,
(2RS,3R)-3-amino-4-cyclohexyl-2-hydroxy-N-(3-methoxy-5-(trifluoromethyl)phenyl)butanamide,
(2RS,3R)-3-amino-4-cyclohexyl-N-decyl-2-hydroxybutanamide,
(2RS,3R)-3-amino-N-((1R,4S)bicyclo(2.2.1)hept-2-yl)-4-cyclohexyl-2-hydroxybutanamide,
(2RS,3R)-3-amino-4-cyclohexyl-N-(2-fluorobenzyl)-2-hydroxybutanamide,
(2RS,3R)-3-amino-4-cyclohexyl-N-(4-fluoro-3-(trifluoromethyl)benzyl)-2-hydroxybutanamide,
(2RS,3R)-3-amino-4-cyclohexyl-N-(1-(4-fluorophenyl)ethyl)-2-hydroxybutanamide,
tert-butyl (2RS,3R)-2-((3-amino-4-cyclohexyl-2-hydroxybutanoyl)amino)acetate,
methyl (2RS,3R)-2-((3-amino-4-cyclohexyl-2-hydroxybutanoyl)amino-3-phenylpropanoate,
methyl (2RS,3R,2'S)-2-((3-amino-4-cyclohexyl-2-hydroxybutanoyl)amino)-3-methylpentanoate,
methyl (2RS,3R,2'S)-2-((3-amino-4-cyclohexyl-2-hydroxybutanoyl)amino)hexanoate,
methyl (2RS,3R)-2-((3-amino-4-cyclohexyl-2-hydroxybutanoyl)amino)-3-methylbutanoate,
(2RS,3R)-3-amino-4-cyclohexyl-2-hydroxy-N-((1S)-1-(2-naphthyl)ethyl)butanamide,
(2RS,3R)-3-amino-4-cyclohexyl-2-hydroxy-N-((1R)-1-(2-naphthyl)ethyl)butanamide,
(2RS,3R)-3-amino-4-cyclohexyl-2-hydroxy-N-((1S)-1-(1-naphthyl)ethyl)butanamide,
(2RS,3R)-3-amino-4-cyclohexyl-2-hydroxy-N-((1R)-1-(1-naphthyl)ethyl)butanamide,
ethyl (2RS,3R,2'R)-2-((3-amino-4-cyclohexyl-2-hydroxybutanoyl)amino)-3-fluoropropanoate,
(2RS,3R)-3-amino-4-cyclohexyl-2-hydroxy-N-(2-hydroxy-1-(hydroxymethyl)ethyl)butanamide,
4-(tert-butyl)benzyl (2RS,3R,2'R)-2-((3-amino-4-cyclohexyl-2-hydroxybutanoyl)amino)-3-hydroxypropanoate,
4-nitrobenzyl (2RS,3R,2'S)-2-((3-amino-4-cyclohexyl-2-hydroxybutanoyl)amino)-3-hydroxypropanoate,
3-nitrobenzyl (2RS,3R,2'S)-2-((3-amino-4-cyclohexyl-2-hydroxybutanoyl)amino)-3-hydroxypropanoate,
4-(trifluoromethyl)benzyl (2RS,3R,2'S)-2-((3-amino-4-cyclohexyl-2-hydroxybutanoyl)amino)-3-hydroxypropanoate,
3-(trifluoromethyl)benzyl (2RS,3R,2'S)-2-((3-amino-4-cyclohexyl-2-hydroxybutanoyl)amino)-3-hydroxypropanoate,
(2RS,3R)-3-amino-4-cyclohexyl-N-(4-fluorophenethyl)-2-hydroxybutanamide,
(2RS,3R)-3-amino-4-cyclohexyl-2-hydroxy-N-(4-methylphenyl)butanamide,
(2RS,3R)-3-amino-4-cyclohexyl-N-(4-fluorophenyl)-2-hydroxybutanamide,
(2RS,3R)-3-amino-4-cyclohexyl-2-hydroxy-N-(4-methoxyphenyl)butanamide,
(2RS,3R)-3-amino-4-cyclohexyl-2-hydroxy-N-(2-methoxyphenyl)butanamide,
(2RS,3R)-3-amino-N-(4-chlorophenyl)-4-cyclohexyl-2-hydroxybutanamide,
(2RS,3R)-3-amino-N-(3-chlorophenyl)-4-cyclohexyl-2-hydroxybutanamide,
(2RS,3R)-3-amino-N-(2-chlorophenyl)-4-cyclohexyl-2-hydroxybutanamide,
(2RS,3R)-3-amino-N-(4-(tert-butyl)phenyl)-4-cyclohexyl-2-hydroxybutanamide,
(2RS,3R)-3-amino-4-cyclohexyl-2-hydroxy-N-(3-(trifluoromethyl)phenyl)butanamide, (2RS,3R)-3-amino-4-cyclohexyl-2-hydroxy-N-(4-(trifluoromethyl)phenyl)butanamide,
(2RS,3R)-3-amino-4-cyclohexyl-N-(3,4-dichlorophenyl)-2-hydroxybutanamide,
(2RS,3R)-3-amino-4-cyclohexyl-N-(2,4-dichlorophenyl)-2-hydroxybutanamide,
(2RS,3R)-3-amino-N-(4-bromophenyl)-4-cyclohexyl-2-hydroxybutanamide,
(2RS,3R)-3-amino-N-(4-(tert-butyl)benzyl)-4-cyclohexyl-2-hydroxybutanamide,
(2RS,3R)-3-amino-4-cyclohexyl-2-hydroxy-N-(3-trifluoromethyl)benzyl)butanamide,
(2RS,3R)-3-amino-4-cyclohexyl-2-hydroxy-N-(4-(trifluoromethyl)benzyl)butanamide,
(2RS,3R)-3-amino-N-(2-chlorobenzyl)-4-cyclohexyl-2-hydroxybutanamide,
(2RS,3R)-3-amino-4-cyclohexyl-2-hydroxy-N-(2-methoxy-5-nitrophenyl)butanamide,
(2RS,3R)-3-amino-4-cyclohexyl-N-(3,5-dimethoxyphenyl)-2-hydroxybutanamide,
(2RS,3R)-3-amino-4-cyclohexyl-2-hydroxy-N-(3-phenoxyphenyl)butanamide,
(((2RS,3R)-3-amino-4-cyclohexyl-2-hydroxybutanoyl)amino)(2,5-dimethoxybenzyl)chloronium,
(2RS,3R)-3-amino-4-cyclohexyl-N-(2,4-dichlorophenethyl)-2-hydroxybutanamide,
(2RS,3R)-3-amino-4-cyclohexyl-N-(2,6-dichlorophenethyl)-2-hydroxybutanamide,
(2RS,3R)-3-amino-4-cyclohexyl-N-(3-fluorophenethyl)-2-hydroxybutanamide,
(2RS,3R)-3-amino-N-(3,4-bis(benzyloxy)phenethyl)-4-cyclohexyl-2-hydroxybutanamide,
(2RS,3R)-3-amino-4-cyclohexyl-2-hydroxy-N-(4-phenoxyphenethyl)butanamide,
(2RS,3R)-3-amino-4-cyclohexyl-2-hydroxy-N-(2-(trifluoromethoxy)phenyl)butanamide,
(2RS,3R)-3-amino-4-cyclohexyl-2-hydroxy-N-(3-(trifluoromethoxy)phenyl)butanamide,
(2RS,3R)-3-amino-4-cyclohexyl-2-hydroxy-N-(2-methylphenyl)butanamide,
(2RS,3R)-3-amino-4-cyclohexyl-N-(2,6-dimethylphenyl)-2-hydroxybutanamide,
(2RS,3R)-3-amino-4-cyclohexyl-2-hydroxy-N-(4-iodo-2-methylphenyl)butanamide,
(2RS,3R)-3-amino-N-(4-anilino-2-methoxyphenyl)-4-cyclohexyl-2-hydroxybutanamide,
(2RS,3R)-3-amino-4-cyclohexyl-N-(2-ethoxyphenyl)-2-hydroxybutanamide,
(2RS,3R)-3-amino-N-(4-chloro-2-methoxy-5-methylphenyl)-4-cyclohexyl-2-hydroxybutanamide,
(2RS,3R)-3-amino-4-cyclohexyl-N-(2,5-dimethoxyphenyl)-2-hydroxybutanamide,
(2RS,3R)-N-(5-(acetylamino)-2-methoxyphenyl)-3-amino-4-cyclohexyl-2-hydroxybutanamide,
(2RS,3R)-3-amino-N-(5-chloro-2,4-dimethoxyphenyl)-4-cyclohexyl-2-hydroxybutanamide,
(2RS,3R)-3-amino-4-cyclohexyl-N-(2,5-diethoxyphenyl)-2-hydroxybutanamide,
(2RS,3R)-3-amino-N-(5-(tert-butyl)-2-methoxyphenyl)-4-cyclohexyl-2-hydroxybutanamide,
(2RS,3R)-3-amino-4-cyclohexyl-2-hydroxy-N-(2-phenoxyphenyl)butanamide,
(2RS,3R)-3-amino-4-cyclohexyl-2-hydroxy-N-(2-methyl-5-nitrophenyl)butanamide,
(2RS,3R)-3-amino-4-cyclohexyl-2-hydroxy-N-(4-phenoxyphenyl)butanamide,
(2RS,3R)-3-amino-4-cyclohexyl-2-hydroxy-N-(4-methoxybenzyl)butanamide,
(2RS,3R)-3-amino-4-cyclohexyl-2-hydroxy-N-(4-methylbenzyl)butanamide,
(2RS,3R)-3-amino-N-(3-chlorobenzyl)-4-cyclohexyl-2-hydroxybutanamide,
(2RS,3R)-3-amino-4-cyclohexyl-2-hydroxy-N-(3-methoxybenzyl)butanamide,
(2RS,3R)-3-amino-N-(4-bromobenzyl)-4cyclohexyl-2-hydroxybutanamide,
(2RS,3R)-3-amino-4-cyclohexyl-4-2-hydroxy-N-(3-methylbenzyl)butanamide,
(2RS,3R)-3-amino-4-cyclohexyl-2-hydroxy-N-phenethylbutanamide,
(2RS,3R)-3-amino-N-(4-chlorobenzyl)-4-cyclohexyl-2-hydroxybutanamide,
(2RS,3R)-3-amino-4-cyclohexyl-2-hydroxy-N-(4-methylphenethyl)butanamide,
(2RS,3R)-3-amino-4-cyclohexyl-2-hydroxy-N-(4-methoxyphenethyl)butanamide,
(2RS,3R)-3-amino-4-cyclohexyl-2-hydroxy-N-(3-methoxyphenethyl)butanamide,
(2RS,3R)-3-amino-4-cyclohexyl-2-hydroxy-N-(2-methoxyphenethyl)butanamide,
(2RS,3R)-3-amino-N-(4-chlorophenethyl)-4-cyclohexyl-2-hydroxybutanamide,
(2RS,3R)-3-amino-N-(3-chlorophenethyl)-4-cyclohexyl-2-hydroxybutanamide,
(2RS,3R)-3-amino-4-cyclohexyl-2-hydroxy-N-(3-(trifluoromethyl)phenethyl)butanamide,
(2RS,3R)-3-amino-N-(4-bromophenethyl)-4-cyclohexyl-2-hydroxybutanamide,
(2RS,3R)-N-(1-adamantyl)-3-amino-4-cyclohexyl-2-hydroxybutanamide,
(2RS,3R)-N-(2-adamantyl)-3-amino-4-cyclohexyl-2-hydroxybutanamide,
(2RS,3R)-3-amino-N-cycloheptyl-4-cyclohexyl-2-hydroxybutanamide,
(2RS,3R)-3-amino-4-cyclohexyl-N-(cyclohexylmethyl)-2-hydroxybutanamide,
(2RS,3R)-3-amino-N,4-dicyclohexyl-2-hydroxybutanamide,
(2RS,3R)-3-amino-4-cyclohexyl-N-cyclopentyl-2-hydroxybutanamide,
(2RS,3R)-3-amino-N-cyclobutyl-4-cyclohexyl-2-hydroxybutanamide,
(2RS,3R)-3-amino-4-cyclohexyl-2-hydroxy-N-(1-methyl-3-phenylpropyl)butanamide,
(2RS,3R)-3-amino-4-cyclohexyl-2-hydroxy-N-(1-methyl-2-(3-(trifluoromethyl)phenyl)ethyl)butanamide,
(2RS,3R)-3-amino-4-cyclohexyl-N-(1,5-dimethylhexyl)-2-hydroxybutanamide,
(2RS,3R)-3-amino-4-cyclohexyl-2-hydroxy-N-(1-methylhexyl)butanamide,
(2RS,3R)-3-amino-4-cyclohexyl-2-hydroxy-N-(3-isopropoxypropyl)butanamide,
(2RS,3R)-3-amino-4-cyclohexyl-2-hydroxy-N-(3-isobutoxypropyl)butanamide,
(2RS,3R)-3-amino-4-cyclohexyl-N-(3,3-diphenylpropyl)-2-hydroxybutanamide,
(2RS,3R)-3-amino-4-cyclohexyl-N-(1,4-dimethylpentyl)-2-hydroxybutanamide,
(2RS,3R)-3-amino-4-cyclohexyl-2-hydroxy-N-methyl-N-(1-naphthylmethyl)butanamide,
(2RS,3R)-3-amino-4-cyclohexyl-2-hydroxy-N-methyl-N-((1S)-1-(1-naphthyl)ethyl)butanamide,
(2RS,3R)-3-amino-4-cyclohexyl-2-hydroxy-N-(2-methoxy-5-(trifluoromethyl)phenyl)butanamide,
(2RS,3R)-3-amino-4-cyclohexyl-2-hydroxy-N-(4-methoxy (1,1'-biphenyl)-3-yl)butanamide, (2RS,3R)-3-amino-N-(3-(benzyloxy)phenyl)-4-cyclohexyl-2-hydroxybutanamide,
(2RS,3R)-3-amino-4-cyclohexyl-N-(3-ethoxyphenyl)-2-hydroxybutanamide,
(2RS,3R)-3-amino-4-cyclohexyl-2-hydroxy-N-(3,4,5-trimethoxyphenyl)butanamide,
(2RS,3R)-3-amino-4-cyclohexyl-N-(2-(2-fluorophenyl)-1-methylethyl)-2-hydroxybutanamide,
(2RS,3R)-3-amino-4-cyclohexyl-N-(2-(4-fluorophenyl)-1,1-dimethylethyl)-2-hydroxybutanamide,
(2RS,3R)-3-amino-4-cyclohexyl-N-(2,3-dihydro-1H-inden-1-yl)-2-hydroxybutanamide,
(2RS,3R)-3-amino-4-cyclohexyl-2-hydroxy-N-((1S,2R)-2-phenylcyclopropyl)butanamide,
(2RS,3R)-3-amino-4-cyclohexyl-2-hydroxy-N-(1,1,3,3-tetramethylbutyl)butanamide,
(2RS,3R)-3-amino-4-cyclohexyl-N-(1,3-dimethylbutyl)-2-hydroxybutanamide,
(2RS,3R)-N-(1-(1-adamantyl)ethyl)-3-amino-4-cyclohexyl-2-hydroxybutanamide,
(2RS,3R)-3-amino-4-cyclohexyl-2-hydroxy-N-(1-naphthylmethyl)butanamide,
(2RS,3R)-3-amino-4-cyclohexyl-2-hydroxy-N-(3-(trifluoromethoxy)benzyl)butanamide,
(2RS,3R)-3-amino-N-(3,5-bis(trifluoromethyl)benzyl)-4-cyclohexyl-2-hydroxybutanamide,
(2RS,3R)-3-amino-4-cyclohexyl-2-hydroxy-N-(2-(trifluoromethyl)benzyl)butanamide,
(2RS,3R)-3-amino-4-cyclohexyl-2-hydroxy-N-(4-(trifluoromethoxy)benzyl)butanamide,
(2RS,3R)-3-amino-N-(5-chloro-2-methoxyphenyl)-4-cyclohexyl-2-hydroxybutanamide,
(2RS,3R)-3-amino-4-cyclohexyl-2-hydroxy-N-(2-methoxy-5-methylphenyl)butanamide,
(2RS,3R)-3-amino-N-(4-chloro-2,5-dimethoxyphenyl)-4-cyclohexyl-2-hydroxybutanamide,
(2RS,3R)-3-amino-4-cyclohexyl-N-(2,3-dimethoxyphenyl)-2-hydroxybutanamide,
(2RS,3R)-3-amino-4-cyclohexyl-N-(3,4-dimethoxyphenyl)-2-hydroxybutanamide,
(2RS,3R)-3-amino-4-cyclohexyl-2-hydroxy-N-(3-methoxy-4-methylphenyl)butanamide,
(2RS,3R)-3-amino-4-cyclohexyl-2-hydroxy-N-(4-methoxy-2-naphthyl)butanamide,
(2RS,3R)-3-amino-N-butyl-4-cyclohexyl-2-hydroxy-N-methylbutanamide,
(2RS,3R)-3-amino-4-cyclohexyl-2-hydroxy-N,N-bix(methoxymethyl)butanamide,
(2RS,3R)-3-amino-N-benzyl-N-butyl-4-cyclohexyl-2-hydroxybutanamide,
(2RS,3R)-3-amino-N-4-cyclohexyl-2-hydroxy-N-methylbutanamide,
(2RS,3R)-3-amino-4-cyclohexyl-N-(2,4-dichlorobenzyl)-N-ethyl-2-hydroxybutanamide, and
ethyl 3-propanoate.

10. A compound in accordance with claim 4, or a pharmaceutically acceptable salt thereof, wherein $R^2$ is alkyl.

11. A compound in accordance with claim 2, or a pharmaceutically acceptable salt thereof, wherein the stereochemistry at the chiral center designated "1" is of the S configuration.

12. A compound in accordance with claim 11, or a pharmaceutically acceptable salt thereof, wherein $R^2$ is —$SR^5$.

13. A pharmaceutical composition comprising a compound in accordance with claim 1 or a pharmaceutically acceptable salt thereof, in combination with a pharmaceutically acceptable carrier.

14. A method of inhibiting angiogenesis in a mammal comprising adminstering to the mammal a therapeutically effective amount of a compound of claim 1.

15. A compound or a pharmaceutically acceptable salt thereof, selected from the group consisting of (2RS,3R)-N-((2-phenylethyl)-3-amino-2-hydroxy-5-(methylthio)pentanamide,
(2RS,3R)-N-((3-phenylpropyl)-3-amino-2-hydroxy-5-(methylthio)pentanamide,
(2RS,3R)-N-(4-phenylbutyl)-3-amino-2-hydroxy-5-(methylthio)pentanamide,
(2RS,3R)N-(2-(4-methoxyphenyl)ethyl)-3-amino-2-hydroxy-5-(methylthio)pentanamide,
(2RS,3R)-N-(2-(4-sulfonamidophenyl)ethyl)-3-amino-2-hydroxy-5-(methylthio)pentanamide,
(2RS,3R)-N-(2-(4-phenoxyphenyl)ethyl)-3-amino-2-hydroxy-5-(methylthio)pentanamide,
(2RS,3R)-N-(4-phenyl)butyl)-3-amino-2-hydroxy-5-(ethylthio)pentanamide,
(2RS,3R)-N-(3-(carbobenzyloxy)ethyl)-3-amino-2-hydroxy-5-(ethylthio)pentanamide,
(2RS,3R)-N-(2-(carboethoxy)ethyl)-3-amino-2-hydroxy-4-butanamide,
(2RS,3R)-N-(3-carboethoxy)propyl)-3-amino-2-hydroxy-4-phenyl-butanamide,
(2RS,3R)-N-(4-phenylbutyl)-3-amino-2-hydroxy-4-phenyl-butanamide,
(2RS,3R,1'S)-N-((1-ethoxycarbonyl)ethyl)-3-amino-2-hydroxy-4-cyclohexylbutanamide,
(2RS,3R)-N-(2-carboethoxy)ethyl)-3-amino-2-hydroxy-4-cyclohexylbutanamide,
(2RS,3R)-N-(3-(carboethoxy)propyl)-3-amino-2-hydroxy-4-cyclohexylbutanamide,
(2RS,3R,1'S)-N-((1-ethoxycarbonyl)ethyl)-3-amino-2-hydroxy-4-phenylbutanamide,
(2RS,3R)-3-amino-2-hydroxy-N-(4-methoxyphenethyl)-5-(methylthio)pentanamide,
(2RS,3R)-N-((2-phenylbutyl)-3-tert-butoxycarbonylamino-2-hydroxy-5-(ethylthio)pentanamide,
(2RS,3R)-N-((2-phenylbutyl)-3-acetylamino-2-hydroxy-5-(ethylthio)pentanamide,
(2RS,3R)-N-((phenylbutyryl)-3-amino-2-hydroxy-4-cyclohexyl)butanamide,
(2RS,3R)-N-((phenylbutyryl)-3-methoxycarbonylamino-2-hydroxy-4-ethylthio)pentanamide,
(2RS,3R)-3-amino-2-hydroxy-N-methyl-5-(methylthio)-N-phenethylpentanamide,
(2RS,3R)-N-((phenylbutyryl)-3-tert-butoxycarbonylamino-2-hydroxy-4-ethylthio)pentanamide,
(2RS,3R)-N-((phenylbutyryl)-3-formylamino-2-hydroxy-4-ethylthio)pentanamide,
(2RS,3R)-N-((phenylbutyryl)-3-hydroxymethylcarbonylamino-2-hydroxy-4-ethylthio)pentanamide,
(2RS,3R,1'R)-N-((1-ethoxycarbonylethyl)-3-amino-2-hydroxy-4-cyclohexyl)butanamide,
(2RS,3R)-N-((1-methyl-1-ethoxycarbonylethyl)-3-amino-2-hydroxy-4-cyclohexyl)butanamide,
(2RS,3R)-N-((phenylbutyryl)-3-methoxycarbonylmethylamino-2-hydroxy-4-ethylthio)pentanamide,
(2RS,3R1'S)-N-((1-ethoxycarbonylethyl)-3-amino-2-hydroxy-4-benzylthio)butanamide,
(2RS,3R,1'S)-N-((2-hydroxy-1-ethoxycarbonylethyl)-3-amino-2-hydroxy-4-cyclohexyl)butanamide, (2RS,3R,1'S)-N-((2-acetoxypropyl)-3-amino-2-hydroxy-4-cyclohexyl)butanamide,
(2RS,3R,2'S)-N-((2-propionyloxypropyl)-3-amino-2-hydroxy-4-cyclohexyl)butanamide,
(2RS,3R,2'S)-N-((2benzoyloxypropyl)-3-amino-2-hydroxy-4-cyclohexyl)butanamide,
(2RS,3R,2'R)-N-((2-benzoyloxypropyl)-3-amino-2-hydroxy-4-cyclohexyl)butanamide,
(2RS,3R,2'R)-N-((2-propionyloxypropyl)-3-amino-2-hydroxy-4-cyclohexyl)butanamide,
(2RS,3R,2'R)-N-((2-acetoxypropyl)-3-amino-2-hydroxy-4-cyclohexyl)butanamide,
(2RS,3R,1'S)-N-((1-benzyloxycarbonylethyl)-3-amino-2-hydroxy-4-cyclohexyl)butanamide,
(2RS,3R)-N-(monodansylcadaverenyl)-3-amino-2-hydroxy-4-cyclohexyl)butanamide,
(2RS,3R)-N-(3-O-methyl-dopaminyl)-3-amino-2-hydroxy-4-cyclohexyl)butanamide,
((2RS,3R)-3-amino-2-hydroxy-4-cyclohexyl)butanoyl-L-alanyl-(3-O-methoxydopamine)amide,
((2RS,3R)-3-amino-2-hydroxy-4-cyclohexyl)butanoyl-L-alanyl-(2-hydroxy-5-nitrophen-1-yl)amide,
((2RS,3R)-3-amino-2-hydroxy-4-cyclohexyl)butanoyl-L-alanyl-(4-nitro-2-hydroxyphen-1-yl)amide,
ethyl(2RS,3R,2'S)-2-((-3-(acetylamino)-4-cyclohexyl-2-hydroxybutanoyl)amino)propanoate,
(2RS,3R)-3-amino-2-hydroxy-4-cyclohexyl)butanoyl-(4-benzyloxycarbonylamino)butylamide,
(2RS,3R)-3-amino-2-hydroxy-4-cyclohexyl)butanoyl-beta-alaninebenzylester,
(2RS,3R)-N-(monodansylcadaverenyl)-3-amino-2-hydroxy-5-ethylthio)pentanamide,
(2RS,3R)-3-amino-2-hydroxy-4-cyclohexyl)butanoyl-(4-(4-toluenesulfonyl)aminobutyl)amide,
(2RS,3R)-3-amino-2-hydroxy-4-cyclohexyl)butanoyl-(2-4-toluenesulfonylaminoethyl)amide,
(2RS,3R)-3-amino-2-hydroxy-4-cyclohexyl)butanoyl-(4-aminobutyl)amide,
(2RS,3R)-3-amino-2-hydroxy-4-cyclohexyl)butanoyl-(2-aminoethyl)amide,
(2RS,3R)-3-amino-4-cyclohexyl-2-hydroxy-N-(4-(((3-(trifluoromethyl)phenyl)sulfonyl)amino)butyl)butanamide,
(2RS,3R)-3-amino-4-cyclohexyl-N-(4-(((3,4-dimethoxyphenyl)sulfonyl)amino)butyl)-2-hydroxybutanamide,
(2RS,3R)-N-(4-(((4-acetylamino)phenyl)sulfonyl)amino)butyl)-3-amino-4-cyclohexyl-2-hydroxybutanamide,
(2RS,3R)-3-amino-4-cyclohexyl-2-hydroxy-N-(4-((2-naphthylsulfonyl)amino)butyl)butanamide,
(2RS,3R)-3-amino-2-hydroxy-4-cyclohexyl)butanoyl-L-alanine-4-sulfonamidebenzylester,
(2RS,3R)-3-amino-2-hydroxy-4-cyclohexyl)butanoyl-L-alaninebenzylester,
(2RS,3R)-3-amino-2-hydroxy-4-cyclohexyl)butanoyl-L-alaninecyclohexylester,
(2RS,3R)-3-amino-2-hydroxy-4-cyclohexyl)butanoyl-L-alanine-2-((phenylsulfonyl)methyl)benzylester,
(2RS,3R)-3-amino-2-hydroxy-4-cyclohexyl)butanoyl-L-alaninecyclopropylester,
(2RS,3R)-3-amino-2-hydroxy-4-cyclohexyl)butanoyl-L-alanine-4-tert-butylbenzylester,
(2RS,3R)-3-amino-2-hydroxy-4-cyclohexyl)butanoyl-L-alanine-4-methoxycarbonylbenzylester,
(2RS,3R)-3-amino-2-hydroxy-4-cyclohexyl)butanoyl-L-alanine-4-trifluoromethylbenzylester,
(2RS,3R)-3-amino-2-hydroxy-4-cyclohexyl)butanoyl-L-alanine-(4-(methyl)phenylaceticacidphenacylester),
(2RS,3R)-3-amino-4-cyclohexyl-N-(2,4-dichlorobenzyl)-2-hydroxybutanamide,
(2RS,3R)-3-amino-4-cyclohexyl-2-hydroxy-N--(3-methoxyphenyl)butanamide,
methyl(2RS,3R,2'R)-2-((3-amino-4-cyclohexyl-2-hydroxybutanoyl)amino)-4-methylpentanoate,
(2RS,3R,1'RS)-3-amino-4-cyclohexyl-2-hydroxy-N-(1-(1-naphthyl)ethyl)butanamide,
(2RS,3R)-3-amino-4-cyclohexyl-N-(1,2-dimethylpropyl)-2-hydroxybutanamide,
(2RS,3R)-3-amino-2-hydroxy-4-cyclohexyl)butanoyl-L-alanine,
(2RS,3R)-3-amino-4-cyclohexyl-2-hydroxy-N-phenylbutanamide,
(2RS,3R)-3-amino-N-(2-chlorophenethyl)-4-cyclohexyl-2-hydroxybutanamide,
(2RS,3R)-3-amino-4-cyclohexyl-2-hydroxy-N-(3-phenylpropyl)butanamide,
(2RS,3R)-3-amino-4-cyclohexyl-2-hydroxy-N-(1,2,3,4-tetrahydro-1-naphthalenyl)butanamide,
(2RS,3R)-3-amino-N-(4-(tert-butyl)cyclohexyl)-4-cyclohexyl-2-hydroxybutanamide,
(2RS,3R)-3-amino-4-cyclohexyl-N-(3,5-dichlorophenyl)-2-hydroxybutanamide,
(2RS,3R)-3-amino-4-cyclohexyl-N-(2-ethylhexyl)-2-hydroxybutanamide,
butyl(2RS,3R)-2-((3-amino-4-cyclohexyl-2-hydroxybutanoyl)amino)acetate,
(2RS,3R)-3-amino-4-cyclohexyl-N-(2,4-dimethoxyphenyl)-2-hydroxybutanamide,
(2RS,3R)-3-amino-4-cyclohexyl-2-hydroxy-N-(3-methoxy-5-(trifluoromethyl)phenyl)butanamide,
(2RS,3R)-3-amino-4-cyclohexyl-N-decyl-2-hydroxybutanamide,
(2RS,3R)-3-amino-N-((1R,4S)bicyclo(2.2.1)hept-2-yl)-4-cyclohexyl-2-hydroxybutanamide,
(2RS,3R)-3-amino-4-cyclohexyl-N-(2-fluorobenzyl)-2-hydroxybutanamide,
(2RS,3R)-3-amino-4-cyclohexyl-N-(4-fluoro-3-(trifluoromethyl)benzyl)-2-hydroxybutanamide,
(2RS,3R)-3-amino-4-cyclohexyl-N-(1-(4-fluorophenyl)ethyl)-2-hydroxybutanamide,
tert-butyl(2RS,3R)-2-((3-amino-4-cyclohexyl-2-hydroxybutanoyl)amino)acetate,
methyl(2RS,3R)-2-((3-amino-4-cyclohexyl-2-hydroxybutanoyl)amino)-3-phenylpropopanoate,
methyl(2RS,3R,2'S)-2-((3-amino-4-cyclohexyl-2-hydroxybutanoyl)amino)-3-methylpentanoate,
methyl(2RS,3R,2'S)-2-((3-amino-4-cyclohexyl-2-hydroxybutanoyl)amino)hexanoate,
methyl(2RS,3R)-2-((3-amino-4-cyclohexyl-2-hydroxybutanoyl)amino-3-methylbutanoate,
(2RS,3R)-3-amino-4-cyclohexyl-2-hydroxy-N-((1S)-1-(2-naphthyl)ethyl)butanamide,
(2RS,3R)-3-amino-4-cyclohexyl-2-hydroxy-N-((1R)-1-(2-naphthyl)ethyl)butanamide,
(2RS,3R)-3-amino-4-cyclohexyl-2-hydroxy-N-((1S)-1-(1-naphthyl)ethyl)butanamide,
(2RS,3R)-3-amino-4-cyclohexyl-2-hydroxy-N-((1R)-1-(1-naphthyl)ethyl)butanamide,
ethyl(2RS,3R,2'R)-2-((3-amino-4-cyclohexyl-2-hydroxybutanoyl)amino)-3-fluoropropanoate,
(2RS,3R)-3-amino-4-cyclohexyl-2-hydroxy-N-(2-hydroxy-1-(hydroxymethyl)ethyl)butanamide,
4-(tert-butyl)benzyl(2RS,3R,2'R)-2-((3-amino-4-cyclohexyl-2-hydroxybutanoyl)amino)-3-hydroxypropanoate, 4-nitrobenzyl(2RS,3R,2'S)-2-((3-amino-4-cyclohexyl-2-hydroxybutanoyl)amino)-3-hydroxypropanoate,
3-nitrobenzyl(2RS,3R,2'S)-2-((3-amino-4-cyclohexyl-2-hydroxybutanoyl)amino)-3-hydroxypropanoate,
4-(trifluoromethyl)benzyl(2RS,3R,2'S)-2-((3-amino-4-cyclohexyl-2-hydroxybutanoyl)amino)-3-hydroxypropanoate,
3-(trifluoromethoxy)benzyl(2RS,3R,2'S)-2-((3-amino-4-cyclohexyl-2-hydroxybutanoyl)amino)-3-hydroxypropanoate,
(2RS,3R)-3-amino-4-cyclohexyl-N-(4-fluorophenethyl)-2-hydroxybutanamide,
(2RS,3R)-3amino-4-cyclohexyl-2-hydroxy-N-(4-methylphenyl)butanamide,
(2RS,3R)-3-amino-4-cyclohexyl-N-(4-fluorophenyl)-2-hydroxybutanamide,
(2RS,3R)-3-amino-4-cyclohexyl-2-hydroxy-N-(4-methoxyphenyl)butanamide,
(2RS,3R)-3-amino-4-cyclohexyl-2-hydroxy-N-(2-methoxyphenyl)butanamide,
(2RS,3R)-3-amino-N-(4-chlorophenyl)-4-cyclohexyl-2-hydroxybutanamide,
(2RS,3R)-3-amino-N-(3-chlorophenyl)-4-cyclohexyl-2-hydroxybutanamide,
(2RS,3R)-3-amino-N-(2-chlorophenyl)-4-cyclohexyl-2-hydroxybutanamide,
(2RS,3R)-3-amino-N-(4-(tert-butyl)phenyl)-4-cyclohexyl-2-hydroxybutanamide,
(2RS,3R)-3-amino-4-cyclohexyl-2-hydroxy-N-(3-(trifluoromethyl)phenyl)butanamide,
(2RS,3R)-3-amino-4-cyclohexyl-2-hydroxy-N-(4-(trifluoromethyl)phenyl)butanamide,
(2RS,3R)-3-amino-4-cyclohexyl-N-(3,4-dichlorophenyl)-2-hydroxybutanamide,
(2RS,3R)-3-amino-4-cyclohexyl-N-(2,4-dichlorophenyl)-2-hydroxybutanamide,
(2RS,3R)-3-amino-N-(4-bromophenyl)-4-cyclohexyl-2-hydroxybutanamide,
(2RS,3R)-3-amino-N-(4-(tert-butyl)benzyl)-4-cyclohexyl-2-hydroxybutanamide,
(2RS,3R)-3-amino-4-cyclohexyl-2-hydroxy-N-(3-(trifluoromethyl)benzyl)butanamide,
(2RS,3R)-3-amino-4-cyclohexyl-2-hydroxy-N-(4-(trifluoromethyl)benzyl)butanamide,
(2RS,3R)-3-amino-N-(2-chlorobenzyl)-4-cyclohexyl-2-hydroxybutanamide,
(2RS,3R)-3-amino-4-cyclohexyl-2-hydroxy-N-(2-methoxy-5-nitrophenyl)butanamide,
(2RS,3R)-3-amino-4-cyclohexyl-N-(3,5-dimethoxyphenyl)-2-hydroxybutanamide,
(2RS,3R)-3-amino-4-cyclohexyl-2-hydroxy-N-(3-phenoxyphenyl)butanamide,
(((2RS,3R)-3-amino-4-cyclohexyl-2-hydroxybutanoyl)amino)(2,5-dimethoxybenzyl)chloronium,
(2RS,3R)-3-amino-4-cyclohexyl-N-(2,4-dichlorophenethyl)-2-hydroxybutanamide,
(2RS,3R)-3-amino-4-cyclohexyl-N-(2,6-dichlorophenethyl)-2-hydroxybutanamide,
(2RS,3R)-3-amino-4-cyclohexyl-N-(3-fluorophenethyl)-2-hydroxybutanamide,
(2RS,3R)-3amino-N-(3,4-bis(benzyloxy)phenethyl)-4-cyclohexyl-2-hydroxybutanamide,
(2RS,3R)-3-amino-4-cyclohexyl-2-hydroxy-N-(4-phenoxyphenethyl)butanamide,
(2RS,3R)-3-amino-4-cyclohexyl-2-hydroxy-N-(2-(trifluoromethoxy)phenyl)butanamide,
(2RS,3R)-3-amino-4-cyclohexyl-2-hydroxy-N-(3-(trifluoromethoxy)phenyl)butanamide,
(2RS,3R)-3-amino-4-cyclohexyl-2-hydroxy-N-(2-methylphenyl)butanamide,
(2RS,3R)-3-amino-4-cyclohexyl-N-(2,6-dimethylphenyl)-2-hydroxybutanamide,
(2RS,3R)-3-amino-4-cyclohexyl-2-hydroxy-N-(4-iodo-2-methylphenyl)butanamide,
(2RS,3R)-3-amino-N-(4-anilino-2-methoxyphenyl)-4-cyclohexyl-2-hydroxybutanamide,
(2RS,3R)-3-amino-4-cyclohexyl-N-(2-ethoxyphenyl)-2-hydroxybutanamide,
(2RS,3R)-3-amino-N-(4-chloro-2-methoxy-5-methylphenyl)-4-cyclohexyl-2-hydroxybutanamide,
(2RS,3R)-3-amino-4-cyclohexyl-N-(2,5-dimethoxyphenyl)-2-hydroxybutanamide,
(2RS,3R)-N-(5-(acetylamino)-2-methoxyphenyl)-3-amino-4-cyclohexyl-2-hydroxybutanamide,
(2RS,3R)-3-amino-N-(5-chloro-2,4-dimethoxyphenyl)-4-cyclohexyl-2-hydroxybutanamide,
(2RS,3R)-3-amino-4-cyclohexyl-N-(2,5-diethoxyphenyl)-2-hydroxybutanamide,
(2RS,3R)-3-amino-N-(5-(tert-butyl)-2-methoxyphenyl)-4-cyclohexyl-2-hydroxybutanamide,
(2RS,3R)-3-amino-4-cyclohexyl-2-hydroxy-N-(2-phenoxyphenyl)butanamide,
(2RS,3R)-3-amino-4-cyclohexyl-2-hydroxy-N-(2-methyl-5-nitrophenyl)butanamide,
(2RS,3R)-3-amino-4-cyclohexyl-2-hydroxy-N-(4-phenoxyphenyl)butanamide,
(2RS,3R)-3-amino-4-cyclohexyl-2-hydroxy-N-(4-methoxybenzyl)butanamide,
(2RS,3R)-3-amino-4-cyclohexyl-2-hydroxy-N-(4-methylbenzyl)butanamide,
(2RS,3R)-3-amino-N-(3-chlorobenzyl)-4-cyclohexyl-2-hydroxybutanamide,
(2RS,3R)-3-amino-4-cyclohexyl-2-hydroxy-N-(3-methoxybenzyl)butanamide,
(2RS,3R)-3-amino-N-(4-bromobenzyl)-4-cyclohexyl-2-hydroxybutanamide,
(2RS,3R)-3-amino-4-cyclohexyl-2-hydroxy-N-(3-methylbenzyl)butanamide,
(2RS,3R)-3-amino-4-cyclohexyl-2-hydroxy-N-phenethylbutanamide,
(2RS,3R)-3-amino-N-(4-chlorobenzyl)-4-cyclohexyl-2-hydroxybutanamide,
(2RS,3R)-3-amino-4-cyclohexyl-2-hydroxy-N-(4-methylphenethyl)butanamide,
(2RS,3R)-3-amino-4-cyclohexyl-2-hydroxy-N-(4-methoxyphenethyl)butanamide,
(2RS,3R)-3-amino-4-cyclohexyl-2-hydroxy-N-(3-methoxyphenethyl)butanamide,
(2RS,3R)-3-amino-4-cyclohexyl-2-hydroxy-N-(2-methoxyphenethyl)butanamide,
(2RS,3R)-3-amino-N-(4-chlorophenethyl)-4-cyclohexyl-2-hydroxybutanamide,
(2RS,3R)-3-amino-N-(3-chlorophenethyl)-4-cyclohexyl-2-hydroxybutanamide,
(2RS,3R)-3-amino-4-cyclohexyl-2-hydroxy-N-(3-(trifluoromethyl)phenethyl)butanamide,
(2RS,3R)-3-amino-N-(4-bromophenethyl)-4-cyclohexyl-2-hydroxybutanamide,
(2RS,3R)-N-(1-adamantyl)-3-amino-4-cyclohexyl-2-hydroxybutanamide,
(2RS,3R)-N-(2-adamantyl)-3-amino-4-cyclohexyl-2-hydroxybutanamide,
(2R,3R)-3-amino-N-cycloheptyl-4-cyclohexyl-2-hydroxybutanamide,
(2RS,3R)-3-amino-4-cyclohexyl-N-(cyclohexylmethyl)-2-hydroxybutanamide, (2RS,3R)-3-amino-N-4-dicyclohexyl-2-hydroxybutanamide,
(2RS,3R)-3-amino-4-cyclohexyl-N-cyclopentyl-2-hydroxybutanamide,
(2RS,3R)-3-amino-N-cyclobutyl-4-cyclohexyl-2-hydroxybutanamide,
(2RS,3R)-3-amino-4-cyclohexyl-2-hydroxy-N-(1-methyl-3-phenylpropyl)butanamide,
(2RS,3R)-3-amino-4-cyclohexyl-2-hydroxy-N-(1-methyl-2-(3-(trifluoromethyl)phenyl)ethyl)butanamide,
(2RS,3R)-3-amino-4-cyclohexyl-N-(1,5-dimethylhexyl)-2-hydroxybutanamide,
(2RS,3R)-3-amino-4-cyclohexyl-2-hydroxy-N-(1-methylhexyl)butanamide,
(2RS,3R)-3-amino-4-cyclohexyl-2-hydroxy-N-(3-isopropoxypropyl)butanamide,
(2RS,3R)-3-amino-4-cyclohexyl-2-hydroxy-N-(3-isobutoxypropyl)butanamide,
(2RS,3R)-3-amino-4-cyclohexyl-N-(3,3-diphenylpropyl)-2-hydroxybutanamide,
(2RS,3R)-3-amino-4-cyclohexyl-N-(1,4-dimethylpentyl)-2-hydroxybutanamide,
(2RS,3R)-3-amino-4-cyclohexyl-2-hydroxy-N-methyl-N-(1-naphthylmethyl)butanamide,
(2RS,3R)-3-amino-4-cyclohexyl-2-hydroxy-N-methyl-N-((1S)-1-(1-naphthyl)ethyl)butanamide,
(2RS,3R)-3-amino-4-cyclohexyl-2-hydroxy-N-(2-methoxy-5-(trifluoromethyl)phenyl)butanamide,
(2RS,3R)-3-amino-4-cyclohexyl-2-hydroxy-N-(4-methoxy(1,1'-biphenyl)-3-yl)butanamide,
(2RS,3R)-3-amino-N-(3-(benzyloxy)phenyl)-4-cyclohexyl-2-hydroxybutanamide,
(2RS,3R)-3-amino-4-cyclohexyl-N-(3-ethoxyphenyl)-2-hydroxybutanamide,
(2RS,3R)-3-amino-4-cyclohexyl-2-hydroxy-N-(3,4,5-trimethoxyphenyl)butanamide,
(2RS,3R)-3-amino-4-cyclohexyl-N-(2-(2-fluorophenyl)-1-methylethyl)-2-hydroxybutanamide,
(2RS,3R)-3-amino-4-cyclohexyl-N-(2-(4-fluorophenyl)-1,1-dimethylethyl)-2-hydroxybutanamide,
(2RS,3R)-3-amino-4-cyclohexyl-N-(2,3-dihydro-1H-inden-1-yl)-2-hydroxybutanamide,
(2RS,3R)-3-amino-4-cyclohexyl-2-hydroxy-N-((1S,2R)-2-phenylcyclopropyl)butanamide,
(2RS,3R)-3-amino-4-cyclohexyl-2-hydroxy-N-(1,1,3,3-tetramethylbutyl)butanamide,
(2RS,3R)-3-amino-4-cyclohexyl-N-(1,3-dimethylbutyl)-2-hydroxybutanamide,
(2RS,3R)-N-(1-(1-adamantyl)ethyl)-3-amino-4-cyclohexyl-2-hydroxybutanamide,
(2RS,3R)-3-amino-2-hydroxy-4-ethylthio)butanoyl-((S)-(−)-(1-naphthyl)ethyl)amide,
(2RS,3R)-3-amino-4-cyclohexyl-2-hydroxy-N-(1-naphthylmethyl)butanamide,
(2RS,3R)-3-amino-4-cyclohexyl-2-hydroxy-N-(3-(trifluoromethoxy)benzyl)butanamide,
(2RS,3R)-3-amino-N-(3,5-bis(trifluoromethyl)benzyl)-4-cyclohexyl-2-hydroxybutanamide,
(2RS,3R)-3-amino-4-cyclohexyl-2-hydroxy-N-(2-(trifluoromethyl)benzyl)butanamide,
(2RS,3R)-3-amino-4-cyclohexyl-2-hydroxy-N-(4-(trifluoromethoxy)benzyl)butanamide,
(2RS,3R)-3-amino-N-(5-chloro-2-methoxyphenyl)-4-cyclohexyl-2-hydroxybutanamide,
(2RS,3R)-3-amino-4-cyclohexyl-2-hydroxy-N-(2-methoxy-5-methylphenyl)butanamide,
(2RS,3R)-3-amino-N-(4-chloro-2,5-dimethoxyphenyl)-4-cyclohexyl-2-hydroxybutanamide,
(2RS,3R)-3-amino-4-cyclohexyl-N-(2,3-dimethoxyphenyl)-2-hydroxybutanamide,
(2RS,3R)-3-amino-4-cyclohexyl-N-(3,4-dimethoxyphenyl)-2-hydroxybutanamide,
(2RS,3R)-3-amino-4-cyclohexyl-2-hydroxy-N-(3-methoxy-4-methylphenyl)butanamide,
(2RS,3R)-3-amino-4-cyclohexyl-2-hydroxy-N-(4-methoxy-2-naphthyl)butanamide,
(2RS,3R)-3-amino-N-butyl-4-cyclohexyl-2-hydroxy-N-methylbutanamide,
(2RS,3R)-3-amino-4-cyclohexyl-2-hydroxy-N,N-bis(methoxymethyl)butanamide,
(2RS,3R)-3-amino-N-benzyl-N-butyl-4-cyclohexyl-2-hydroxybutanamide,
(2RS,3R)-3-amino-N-4-cyclohexyl-2-hydroxy-N-methylbutanamide,
(2RS,3R)-3-amino-4-cyclohexyl-N-(2,4-dichlorobenzyl)-N-ethyl-2-hydroxybutanamide, and
ethyl 3-propanoate.

\* \* \* \* \*

UNITED STATES PATENT AND TRADEMARK OFFICE
CERTIFICATE OF CORRECTION

PATENT NO. : 6,242,494 B1
DATED : June 5, 2001
INVENTOR(S) : Richard A. Craig et al.

It is certified that error appears in the above-identified patent and that said Letters Patent is hereby corrected as shown below:

Column 7,
Line 54, replace "the" with -- The --

Column 8,
Line 7, replace "arylyloxyalkylcarbonyl" with -- aryloxyalkylcarbonyl --

Column 89,
Line 16, replace "wherein is hydrogen" with -- wherein $R^6$ is hydrogen --

Column 91,
Line 2, replace "alamine" with -- alanine --

Column 95,
Line 47, replace "bix" with -- bis --
Line 51, replace 51-52 with -- (2RS, 3R)-3-amino-N-[(2-chloro-2,3,5-cyclohexatrien-1-yl)methyl]-4-cyclohexyl-2-hydroxy-N-methylbutanimide --
Line 55, replace "ethyl 3-propanoate" with -- ethyl 3-[[(2RS,3R)-3-amino-4-cyclohexyl-2-hydroxybutanoyl](benzyl amino]propanoate --

Column 96,
Line 24, replace "4-butanamide" with -- 4-phenyl-butanamide --

Column 98,
Line 3, replace "N--3" with -- N-(-3 --

Column 100,
Line 64, replace "(2R, 3R)" with -- (2RS, 3R) --

UNITED STATES PATENT AND TRADEMARK OFFICE
CERTIFICATE OF CORRECTION

PATENT NO. : 6,242,494 B1
DATED : June 5, 2001
INVENTOR(S) : Richard A. Craig et al.

It is certified that error appears in the above-identified patent and that said Letters Patent is hereby corrected as shown below:

Column 102,
Line 38, replace "(2RS,3R)-3-amino-N-4-cyclohexyl-2-hydroxy-N-methylbutanamide," with -- (2RS, 3R)-3-amino-N-[(2-chloro-2,3,5-cyclohexatrien-1-yl)methyl]-4-cyclohexyl-2-hydroxy-N-methylbutanimide --
Line 43, replace "ethyl 3-propanoate" with -- ethyl 3-[[(2RS,3R)-3-amino-4-cyclohexyl-2-hydroxybutanoyl](benzyl) amino]propanoate --

Signed and Sealed this

Tenth Day of September, 2002

Attest:

JAMES E. ROGAN
Attesting Officer
Director of the United States Patent and Trademark Office